(12) United States Patent
Oh et al.

(10) Patent No.: US 11,844,269 B2
(45) Date of Patent: *Dec. 12, 2023

(54) ORGANIC ELECTROLUMINESCENT COMPOUND AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Hong-Se Oh, Gyeonggi-do (KR); Tae-Jin Lee, Gyeonggi-do (KR); Young-Kwang Kim, Gyeonggi-do (KR); Doo-Hyeon Moon, Gyeonggi-do (KR); Young-Mook Lim, Gyeonggi-do (KR); Jin-Ri Hong, Gyeonggi-do (KR)

(73) Assignee: Rohm and Haas Electronic Materials Korea Ltd.

( * ) Notice: Subject to any disclaimer, the term of this patent is extended or adjusted under 35 U.S.C. 154(b) by 295 days.

This patent is subject to a terminal disclaimer.

(21) Appl. No.: 16/621,451

(22) PCT Filed: May 9, 2018

(86) PCT No.: PCT/KR2018/005292
§ 371 (c)(1),
(2) Date: Dec. 11, 2019

(87) PCT Pub. No.: WO2019/004587
PCT Pub. Date: Jan. 3, 2019

(65) Prior Publication Data
US 2020/0119275 A1    Apr. 16, 2020

(30) Foreign Application Priority Data

Jun. 30, 2017 (KR) .................. 10-2017-0083233
Apr. 24, 2018 (KR) .................. 10-2018-0047294

(51) Int. Cl.
*H10K 85/60* (2023.01)
*H10K 50/15* (2023.01)

(52) U.S. Cl.
CPC ......... *H10K 85/633* (2023.02); *H10K 85/622* (2023.02); *H10K 85/654* (2023.02); *H10K 85/6572* (2023.02); *H10K 85/6574* (2023.02); *H10K 85/6576* (2023.02); *H10K 50/15* (2023.02)

(58) Field of Classification Search
CPC .. H10K 85/633; H10K 85/622; H10K 85/654; H10K 85/6572; H10K 85/657; H10K 85/6576; H10K 50/15; H10K 50/156; H10K 85/636; H10K 85/615; C09K 11/06; C09K 2211/1011; C09K 2211/1014; C07C 211/61; C07D 209/88; C07D 307/91; C07D 333/76; H01L 51/0054; H01L 51/006; H01L 51/0061; H01L 51/0067; H01L 51/0071; H01L 51/0072; H01L 51/0073; H01L 51/0074; H01L 51/5056; H01L 51/5064

See application file for complete search history.

(56) References Cited

U.S. PATENT DOCUMENTS

| | | | | |
|---|---|---|---|---|
| 2009/0184312 A1* | 7/2009 | Nishiyama | ............. | C09K 11/06 257/E51.001 |
| 2012/0146014 A1* | 6/2012 | Kato | ................... | C07D 307/91 548/440 |
| 2015/0329772 A1* | 11/2015 | Heil | ..................... | C07D 409/12 564/426 |
| 2019/0296238 A1* | 9/2019 | Cha | ......................... | H01L 51/50 |
| 2019/0322927 A1* | 10/2019 | Matsuura | ............. | C07D 401/14 |
| 2020/0207713 A1 | 7/2020 | Lee et al. | | |
| 2021/0328152 A1 | 10/2021 | Lee et al. | | |

FOREIGN PATENT DOCUMENTS

| | | | | |
|---|---|---|---|---|
| JP | 3065125 | B2 | 7/2000 | |
| KR | 2015-0006722 | A | 1/2015 | |
| KR | 2016-0052136 | A | 5/2016 | |
| KR | 2016-0054855 | A | 5/2016 | |
| KR | 2017-0088601 | A | 8/2017 | |
| KR | 2017111802 | A * | 10/2017 | |
| WO | 2015/084114 | A1 | 6/2015 | |
| WO | 2017086629 | A1 | 5/2017 | |
| WO | WO-2018182221 | A1 * | 10/2018 | ............. C09K 11/06 |

OTHER PUBLICATIONS

Kim et al., Bulletin of the Korean Chemical Society, 30(3), 647-652. (Year: 2009).*
Jeong, H., Shin, H., Lee, J., Kim, B., Park, Y.I., Yook, K.S., An, B.K. and Park, J., 2015. Recent progress in the use of fluorescent and phosphorescent organic compounds for organic light-emitting diode lighting. Journal of Photonics for Energy, 5(1), pp. 057608-057608. (Year: 2015).*
Shen, J.Y., Lee, C.Y., Huang, T.H., Lin, J.T., Tao, Y.T., Chien, C.H. and Tsai, C., 2005. High T g blue emitting materials for electroluminescent devices. Journal of Materials Chemistry, 15(25), pp. 2455-2463. (Year: 2005).*
Supplementary European Search Report for European patent application No. 18825429.6; dated May 9, 2018.
Cited reference from JPO for Japanese application No. 2019-572535; dated May 9, 2018.

* cited by examiner

*Primary Examiner* — Dawn L Garrett
(74) *Attorney, Agent, or Firm* — G. Creston Campbell

(57) ABSTRACT

The present disclosure relates to an organic electroluminescent compound and an organic electroluminescent device comprising the same. By using the organic electroluminescent compound of the present disclosure, an organic electroluminescent device having low driving voltage, high luminous efficiency, and/or long lifespan properties can be provided.

8 Claims, 1 Drawing Sheet

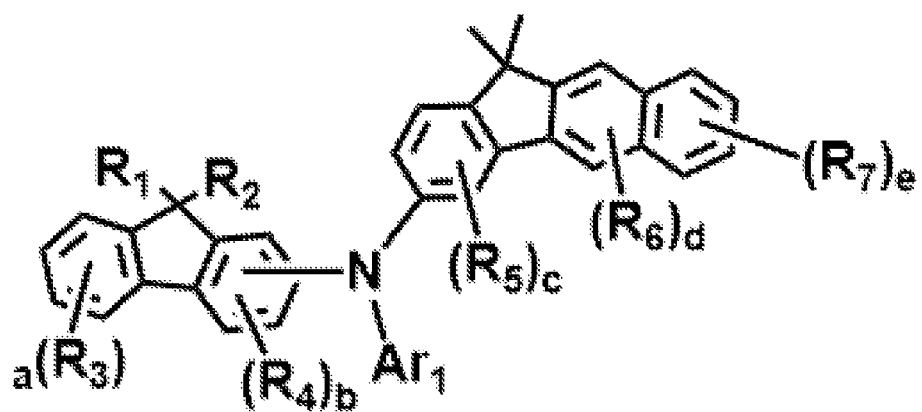

ORGANIC ELECTROLUMINESCENT COMPOUND AND ORGANIC ELECTROLUMINESCENT DEVICE COMPRISING THE SAME

TECHNICAL FIELD

The present disclosure relates to an organic electroluminescent compound and an organic electroluminescent device comprising the same.

BACKGROUND ART

A small molecular green organic electroluminescent device (OLED) was first developed by Tang, et al., of Eastman Kodak in 1987 by using TPD/Alq3 bi-layer consisting of a light-emitting layer and a charge transport layer. Thereafter, the development of OLEDs was rapidly effected and OLEDs have been commercialized. An OLED changes electric energy into light by applying electricity to an organic light-emitting material, and commonly comprises an anode, a cathode, and an organic layer between the two electrodes. In order to enhance the efficiency and stability of an OLED, it has a multilayer structure comprising a hole transport zone, a light-emitting layer, an electron transport zone, etc.

In the OLED, copper phthalocyanine (CuPc), 4,4'-bis[N-(1-naphthyl)-N-phenylamino]biphenyl (NPB), N,N'-diphenyl-N,N'-bis(3-methylphenyl)-(1,1'-biphenyl)-4,4'-diamine (TPD), 4,4',4''-tris(3-methylphenylphenylamino)triphenylamine (MTDATA), etc., were used as a compound contained in the hole transport zone. However, an OLED using these materials is problematic in deteriorating quantum efficiency and lifespan. It is because, when an OLED is driven under high current, thermal stress occurs between an anode and a hole injection layer, and the thermal stress significantly reduces the lifespan of the device. Further, since the organic material used in the hole transport zone has very high hole mobility, the hole-electron charge balance may be broken and quantum efficiency (cd/A) may decrease.

Korean Patent Appln. Laid-Open No. 2015-0066202 published on Jun. 16, 2015 and Japanese Patent Publication No. 3065125 published on May 12, 2000 disclose an OLED in which a fluorene-arylamine derivative compound is used as a hole transport material. However, a compound for improving the performance of an OLED still needs to be developed.

DISCLOSURE OF THE INVENTION

Problems to be Solved

The objective of the present disclosure is to provide an organic electroluminescent compound which can be effectively used to produce an organic electroluminescent device having low driving voltage, high luminous efficiency, and/or long lifespan properties.

Solution to Problems

The present inventors found that by comprising a specific compound having a structure, in which fluorenylamine is bonded to the 3-position of benzofluorene, in a hole transport zone, an organic electroluminescent device can exhibit low driving voltage, high luminous efficiency, and/or long lifespan properties. Specifically, the above objective can be achieved by an organic electroluminescent compound represented by the following formula 1:

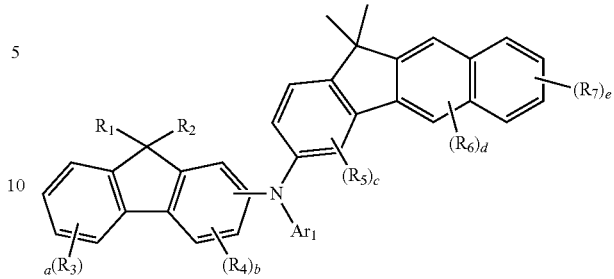

(1)

wherein

Ar$_1$ represents a substituted or unsubstituted (C1-C30) alkyl, a substituted or unsubstituted (C6-C30)aryl, or a substituted or unsubstituted 5- to 30-membered heteroaryl;

R$_1$ and R$_2$ each independently represent hydrogen, deuterium, a halogen, a substituted or unsubstituted (C1-C30)alkyl, a substituted or unsubstituted (C6-C30)aryl, or a substituted or unsubstituted (C3-C30)cycloalkyl; or are linked to an adjacent substituent(s) to form a substituted or unsubstituted, mono- or polycyclic, 3- to 30-membered alicyclic or aromatic ring, or a combination thereof;

R$_3$ to R$_7$ each independently represent hydrogen, deuterium, a halogen, a substituted or unsubstituted (C1-C30)alkyl, a substituted or unsubstituted (C6-C30)aryl, a substituted or unsubstituted 5- to 30-membered heteroaryl, a substituted or unsubstituted (C3-C30)cycloalkyl, a substituted or unsubstituted (C6-C30)aryl (C1-C30)alkyl, —N(R$_{11}$)(R$_{12}$), —Si(R$_{13}$)(R$_{14}$)(R$_{15}$), —S(R$_{16}$), —O(R$_{17}$), a cyano, a nitro, or a hydroxyl;

R$_{11}$ to R$_{17}$ each independently represent hydrogen, deuterium, a halogen, a substituted or unsubstituted (C1-C30)alkyl, a substituted or unsubstituted (C6-C30)aryl, a substituted or unsubstituted 5- to 30-membered heteroaryl, a substituted or unsubstituted 3- to 7-membered heterocycloalkyl, or a substituted or unsubstituted (C3-C30)cycloalkyl; or are linked to an adjacent substituent(s) to form a substituted or unsubstituted, mono- or polycyclic, 3- to 30-membered alicyclic or aromatic ring, or a combination thereof; and a and e each independently represent an integer of 1 to 4, b and c each independently represent an integer of 1 to 3, and d represents an integer of 1 or 2, in which if each of a to e is an integer of 2 or more, each of R$_3$ to R$_7$ may be the same or different.

Effects of the Invention

By using the organic electroluminescent compound of the present disclosure, an organic electroluminescent device having low driving voltage, high luminous efficiency, and/or long lifespan properties can be produced.

BRIEF DESCRIPTION OF THE FIGURE

The FIGURE is the representative formula of the organic electroluminescent compound of the present disclosure.

EMBODIMENTS OF THE INVENTION

Hereinafter, the present disclosure will be described in detail. However, the following description is intended to explain the disclosure, and is not meant in any way to restrict the scope of the disclosure.

An organic electroluminescent device of the present disclosure comprises a first electrode; a second electrode facing the first electrode; a light-emitting layer between the first electrode and the second electrode; a hole transport zone between the first electrode and the light-emitting layer; and an electron transport zone between the light-emitting layer and the second electrode. One of the first and second electrodes may be an anode, and the other may be a cathode.

The term "organic electroluminescent compound" in the present disclosure means a compound that may be used in an organic electroluminescent device, and may be comprised in any material layer constituting an organic electroluminescent device, as necessary.

The term "organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material, an electron buffer material, a hole blocking material, an electron transport material, or an electron injection material.

The term "hole transport zone" in the present disclosure means an area in which holes move between the first electrode and the light-emitting layer, and may comprise, for example, at least one of a hole injection layer, a hole transport layer, a hole auxiliary layer, a light-emitting auxiliary layer, and an electron blocking layer. The hole injection layer, the hole transport layer, the hole auxiliary layer, the light-emitting auxiliary layer, and the electron blocking layer may be, respectively, a single layer, or a multi-layer in which two or more layers are stacked. According to one embodiment of the present disclosure, the hole transport zone may comprise at least one of a hole injection layer, a hole transport layer, and a light-emitting auxiliary layer.

The hole transport layer may be placed between the anode (or the hole injection layer) and the light-emitting layer, enables holes transferred from the anode to smoothly move to the light-emitting layer, and may block the electrons transferred from the cathode to confine electrons within the light-emitting layer. The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or hole transport, or for preventing the overflow of electrons. When the light-emitting auxiliary layer is placed between the cathode and the light-emitting layer, it can be used for promoting the electron injection and/or electron transport, or for preventing the overflow of holes. Also, the hole auxiliary layer may be placed between the hole transport layer (or hole injection layer) and the light-emitting layer, and may be effective to promote or block the hole transport rate (or hole injection rate), thereby enabling the charge balance to be controlled. Further, the electron blocking layer may be placed between the hole transport layer (or hole injection layer) and the light-emitting layer, and can confine the excitons within the light-emitting layer by blocking the overflow of electrons from the light-emitting layer to prevent a light-emitting leakage. When an organic electroluminescent device includes two or more hole transport layers, the hole transport layer, which is further included, may be used as a hole auxiliary layer or an electron blocking layer. The light-emitting auxiliary layer, the hole auxiliary layer or the electron blocking layer may have an effect of improving the efficiency and/or the lifespan of the organic electroluminescent device.

The "electron transport zone" means an area in which electrons move between the second electrode and the light-emitting layer, and may comprise, for example, at least one of an electron buffer layer, a hole blocking layer, an electron transport layer, and an electron injection layer, preferably at least one of an electron buffer layer, an electron transport layer, and an electron injection layer. The electron buffer layer is a layer capable of improving the problem that the current characteristics in the device changes upon exposure to a high temperature in a panel fabrication process to cause deformation of light emission luminance, which can control the flow of charge.

The light-emitting layer is a layer from which light is emitted, and may be a single layer, or a multi-layer in which two or more layers are stacked. The doping concentration of the dopant compound with respect to the host compound in the light-emitting layer is preferably less than 20 wt %.

Hereinafter, the compound represented by formula 1 will be described in detail.

In formula 1 above, $Ar_1$ represents a substituted or unsubstituted (C1-C30)alkyl, a substituted or unsubstituted (C6-C30)aryl, or a substituted or unsubstituted 5- to 30-membered heteroaryl; preferably, a substituted or unsubstituted (C6-C25)aryl, or a substituted or unsubstituted 5- to 25-membered heteroaryl; and more preferably, a substituted or unsubstituted (C6-C18)aryl, or a substituted or unsubstituted 5- to 18-membered heteroaryl, in which the substituent of the substituted aryl or the substituted heteroaryl may be at least one of a (C1-C30)alkyl, a (C6-C30)aryl, and a 5- to 30-membered heteroaryl. According to one embodiment of the present disclosure, $Ar_1$ may represent a phenyl unsubstituted or substituted with at least one methyl(s), phenyl(s), naphthyl(s), pyridyl(s), quinolyl(s), or isoquinolyl(s); a biphenyl; a naphthylphenyl; a phenylnaphthyl; a fluorenyl; a dimethylfluorenyl; a triphenylenyl; a terphenyl; a pyridyl unsubstituted or substituted with at least one phenyl(s), naphthyl(s), or isoquinolinyl(s); a dibenzothiophenyl; a dibenzofuranyl; or a carbazolyl substituted with a phenyl(s).

According to one embodiment of the present disclosure, $Ar_1$ may be selected from the following structures:

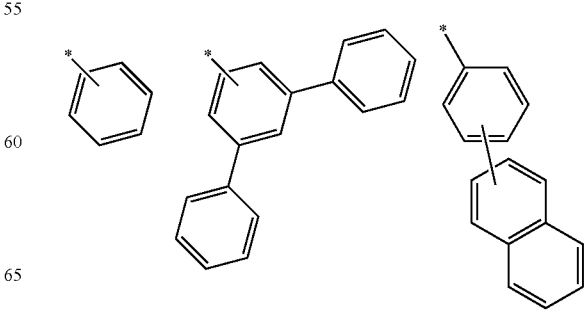

-continued

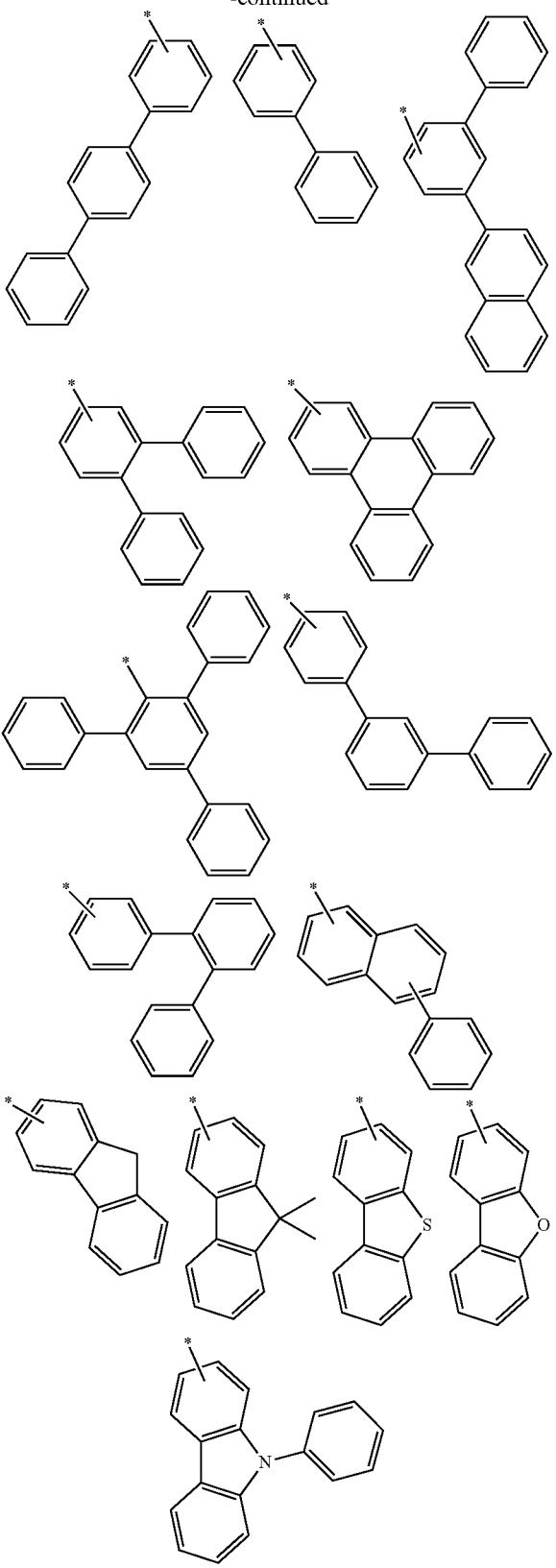

wherein * represents a bonding site with N.

In the above structures, at least one carbon atom of the aromatic ring may be replaced with a nitrogen atom. Further, in the above structures, at least one carbon atom of the aromatic ring may be substituted with at least one selected from the group consisting of deuterium, a halogen, a cyano, a carboxyl, a nitro, a hydroxyl, a (C1-C30)alkyl, a halo(C1-C30)alkyl, a (C2-C30)alkenyl, a (C2-C30)alkynyl, a (C1-C30)alkoxy, a (C1-C30)alkylthio, a (C3-C30)cycloalkyl, a (C3-C30)cycloalkenyl, a 3- to 7-membered heterocycloalkyl, a (C6-C30)aryloxy, a (C6-C30)arylthio, a 5- to 30-membered heteroaryl, a (C6-C30)aryl, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30)arylamino, a (C1-C30)alkyl(C6-C30)arylamino, a (C1-C30)alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30)alkyl, and a (C1-C30)alkyl(C6-C30)aryl.

In formula 1 above, $R_1$ and $R_2$ each independently represent hydrogen, deuterium, a halogen, a substituted or unsubstituted (C1-C30)alkyl, a substituted or unsubstituted (C6-C30)aryl, or a substituted or unsubstituted (C3-C30)cycloalkyl; or are linked to an adjacent substituent(s) to form a substituted or unsubstituted, mono- or polycyclic, 3- to 30-membered alicyclic or aromatic ring, or a combination thereof, in which the formed ring may contain at least one heteroatom selected from nitrogen, oxygen, and sulfur; preferably, a substituted or unsubstituted (C1-C20)alkyl, or a substituted or unsubstituted (C6-C25)aryl; and more preferably, an unsubstituted (C1-C10)alkyl, or an unsubstituted (C6-C18)aryl. According to one embodiment of the present disclosure, $R_1$ and $R_2$ each independently represent methyl or phenyl. $R_1$ and $R_2$ may be the same as or different from each other. According to one embodiment of the present disclosure, $R_1$ and $R_2$ may be the same as each other.

In formula 1 above, $R_3$ to $R_7$ each independently represent hydrogen, deuterium, a halogen, a substituted or unsubstituted (C1-C30)alkyl, a substituted or unsubstituted (C6-C30)aryl, a substituted or unsubstituted 5- to 30-membered heteroaryl, a substituted or unsubstituted (C3-C30)cycloalkyl, a substituted or unsubstituted (C6-C30)aryl(C1-C30)alkyl, $-N(R_{11})(R_{12})$, $-Si(R_{13})(R_{14})(R_{15})$, $-S(R_{16})$, $-O(R_{17})$, a cyano, a nitro, or a hydroxyl; or are linked to an adjacent substituent(s) to form a substituted or unsubstituted, mono- or polycyclic, 3- to 30-membered alicyclic or aromatic ring, or a combination thereof, in which the formed ring may contain at least one heteroatom selected from nitrogen, oxygen, and sulfur; and $R_{11}$ to $R_{17}$ each independently represent hydrogen, deuterium, a halogen, a substituted or unsubstituted (C1-C30)alkyl, a substituted or unsubstituted (C6-C30)aryl, a substituted or unsubstituted 5- to 30-membered heteroaryl, a substituted or unsubstituted 3- to 7-membered heterocycloalkyl, or a substituted or unsubstituted (C3-C30)cycloalkyl; or are linked to an adjacent substituent(s) to form a substituted or unsubstituted, mono- or polycyclic, 3- to 30-membered alicyclic or aromatic ring, or a combination thereof, in which the formed ring may contain at least one heteroatom selected from nitrogen, oxygen, and sulfur.

Preferably, $R_3$ to $R_7$ each independently represent hydrogen, deuterium, a halogen, a substituted or unsubstituted (C1-C20)alkyl, a substituted or unsubstituted (C6-C25)aryl, a substituted or unsubstituted 5- to 25-membered heteroaryl, a substituted or unsubstituted (C3-C25)cycloalkyl, or a substituted or unsubstituted (C6-C25)aryl(C1-C20)alkyl; and more preferably hydrogen, deuterium, a halogen, an unsubstituted (C1-C10)alkyl, an unsubstituted (C6-C18)aryl, an unsubstituted 5- to 18-membered heteroaryl, an unsubstituted (C3-C18)cycloalkyl, or an unsubstituted (C6-C18)aryl(C1-C10)alkyl. According to one embodiment of the present disclosure, $R_3$ to $R_7$ may represent hydrogen.

In formula 1 above, a and e each independently represent an integer of 1 to 4, b and c each independently represent an integer of 1 to 3, and d represents an integer of 1 or 2, in which if each of a to e is an integer of 2 or more, each of $R_3$ to $R_7$ may be the same or different. Preferably, a to e each independently represent an integer of 1 or 2. According to one embodiment of the present disclosure, a to e may represent 1.

In the formula of the present disclosure, if some substituents are linked to an adjacent substituent(s) to form a substituted or unsubstituted, mono- or polycyclic, 3- to 30-membered alicyclic or aromatic ring, or a combination thereof, the formed ring may contain at least one heteroatom selected from nitrogen, oxygen, and sulfur.

In the formula of the present disclosure, the heteroaryl or the heterocycloalkyl may contain at least one heteroatom selected from B, N, O, S, Si, and P, preferably, N, O, and S. The heteroatom may be bonded with at least one substituent selected from the group consisting of hydrogen, deuterium, a halogen, a cyano, a substituted or unsubstituted (C1-C30)alkyl, a substituted or unsubstituted (C6-C30)aryl, a substituted or unsubstituted 5- to 30-membered heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, and a substituted or unsubstituted (C1-C30)alkyl(C6-C30)arylamino.

According to one embodiment of the present disclosure, in formula 1 above, benzofluorenylamine may bond to the 2- or 3-position of fluorene. Specifically, the compound represented by formula 1 may be represented by the following formula 2 or 3:

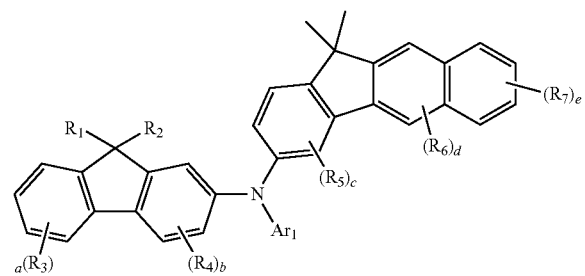

(2)

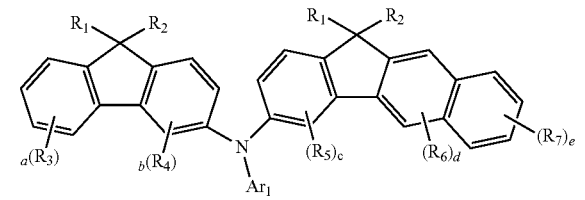

(3)

wherein $Ar_1$, $R_1$ to $R_7$, and a to e are as defined in formula 1.

Herein, "(C1-C30)alkyl" is meant to be a linear or branched alkyl having 1 to 30 carbon atoms constituting the chain, in which the number of carbon atoms is preferably 1 to 20, more preferably 1 to 10, and includes methyl, ethyl, n-propyl, isopropyl, n-butyl, isobutyl, tert-butyl, etc. "(C2-C30)alkenyl" is meant to be a linear or branched alkenyl having 2 to 30 carbon atoms constituting the chain, in which the number of carbon atoms is preferably 2 to 20, more preferably 2 to 10, and includes vinyl, 1-propenyl, 2-propenyl, 1-butenyl, 2-butenyl, 3-butenyl, 2-methylbut-2-enyl, etc. "(C2-C30)alkynyl" is meant to be a linear or branched alkynyl having 2 to 30 carbon atoms constituting the chain, in which the number of carbon atoms is preferably 2 to 20, more preferably 2 to 10, and includes ethynyl, 1-propynyl, 2-propynyl, 1-butynyl, 2-butynyl, 3-butynyl, 1-methylpent-2-ynyl, etc. "(C3-C30)cycloalkyl" is meant to be a mono- or polycyclic hydrocarbon having 3 to 30 ring backbone carbon atoms, in which the number of carbon atoms is preferably 3 to 20, more preferably 3 to 7, and includes cyclopropyl, cyclobutyl, cyclopentyl, cyclohexyl, etc. "3- to 7-membered heterocycloalkyl" is meant to be a cycloalkyl having at least one heteroatom selected from the group consisting of B, N, O, S, Si, and P, preferably O, S, and N, and 3 to 7 ring backbone atoms, preferably 5 to 7 ring backbone atoms, and includes tetrahydrofuran, pyrrolidine, thiolan, tetrahydropyran, etc. "(C6-C30)aryl" is meant to be a monocyclic or fused ring radical derived from an aromatic hydrocarbon having 6 to 30 ring backbone carbon atoms, which may be partially saturated and may have a spiro structure, in which the number of ring backbone carbon atoms is preferably 6 to 25, more preferably 6 to 18, and includes phenyl, biphenyl, terphenyl, naphthyl, binaphthyl, phenylnaphthyl, naphthylphenyl, phenylterphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, etc. "3- to 30-membered heteroaryl" is meant to be an aryl group having at least one, preferably 1 to 4 heteroatoms selected from the group consisting of B, N, O, S, Si, and P, and 3 to 30 ring backbone atoms, which is a monocyclic ring, or a fused ring condensed with at least one benzene ring; may be partially saturated; may be one formed by linking at least one heteroaryl or aryl group to a heteroaryl group via a single bond(s); may have a spiro structure; and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, benzoquinazolinyl, quinoxalinyl, benzoquinoxalinyl, naphthyridinyl, carbazolyl, benzocarbazolyl, dibenzocarbazolyl, phenoxazinyl, phenothiazinyl, phenanthridinyl, benzodioxolyl, dihydroacridinyl, etc. "Halogen" includes F, Cl, Br, and I.

Herein, "substituted" in the expression "substituted or unsubstituted" means that a hydrogen atom in a certain functional group is replaced with another atom or functional group, i.e., a substituent. The substituents of the substituted alkyl, the substituted aryl, the substituted heteroaryl, the substituted cycloalkyl, the substituted heterocycloalkyl, the substituted arylalkyl, or the substituted mono- or polycyclic, alicyclic or aromatic ring, or a combination thereof in $Ar_1$, $R_1$ to $R_7$, and $R_{11}$ to $R_{17}$ in formulas 1 to 3 each independently are at least one selected from the group consisting of deuterium, a halogen, a cyano, a carboxyl, a nitro, a hydroxyl, a (C1-C30)alkyl, a halo(C1-C30)alkyl, a (C2-C30)alkenyl, a (C2-C30)alkynyl, a (C1-C30)alkoxy, a (C1-C30)alkylthio, a (C3-C30)cycloalkyl, a (C3-C30)cycloalkenyl, a 3- to 7-membered heterocycloalkyl, a (C6-C30)aryloxy, a (C6-C30)arylthio, a 5- to 30-membered heteroaryl unsubstituted or substituted with a (C6-C30)aryl(s), a (C6-C30)aryl unsubstituted or substituted with a 5- to 30-membered heteroaryl(s), a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30)arylamino, a (C1-C30)alkyl(C6-C30)arylamino, a (C1-C30)alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30)alkyl, and a (C1-C30)alkyl(C6-C30)aryl; preferably at least one selected from the group consisting of a (C1-C20)alkyl, a (C6-C25)aryl, and a 5- to 25-membered heteroaryl; more preferably at least one selected from the group consisting of a (C1-C10)alkyl, a (C6-C18)aryl, and a 5- to 18-membered heteroaryl; and, for example, at least one selected from the group consisting of methyl, phenyl, naphthyl, pyridyl, quinolyl, and isoquinolyl.

The compound represented by formula 1 includes the following compounds, but is not limited thereto:

C-1

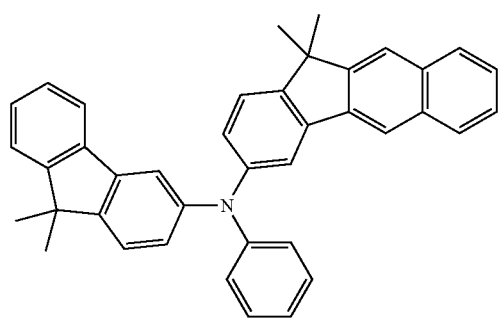

C-2

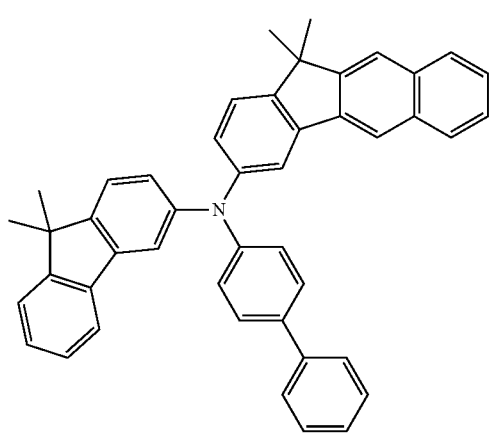

C-3

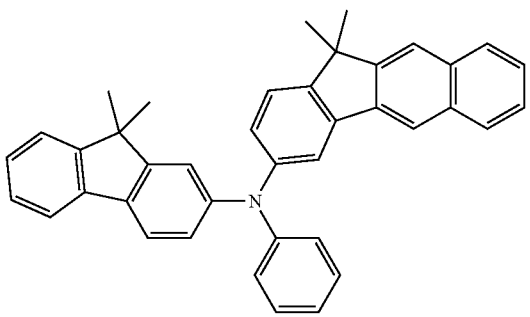

C-4

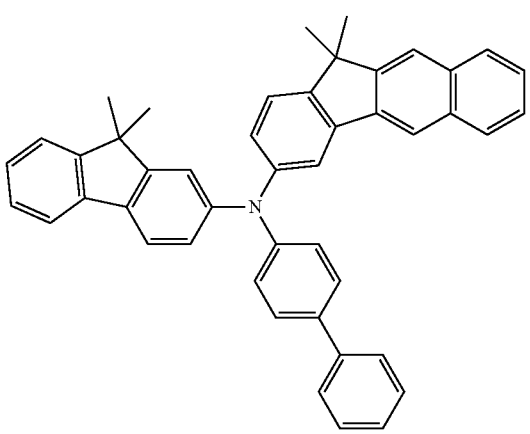

C-5

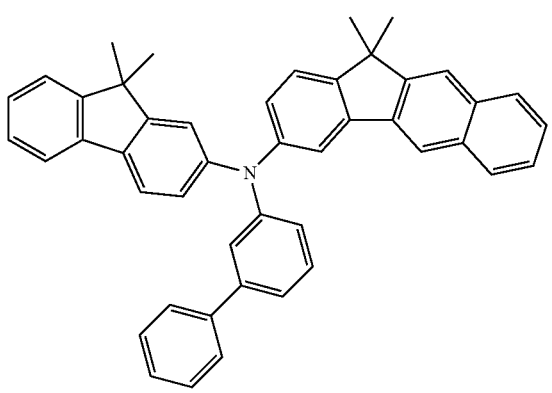

C-6

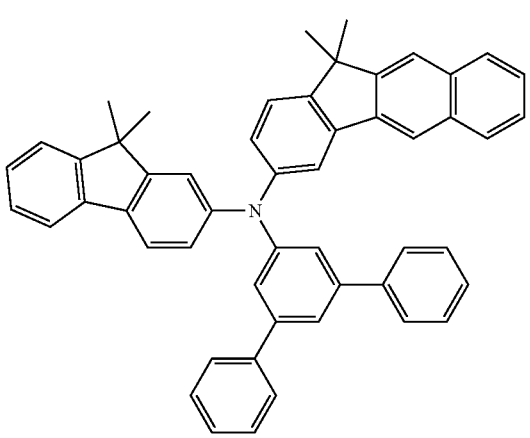

C-7
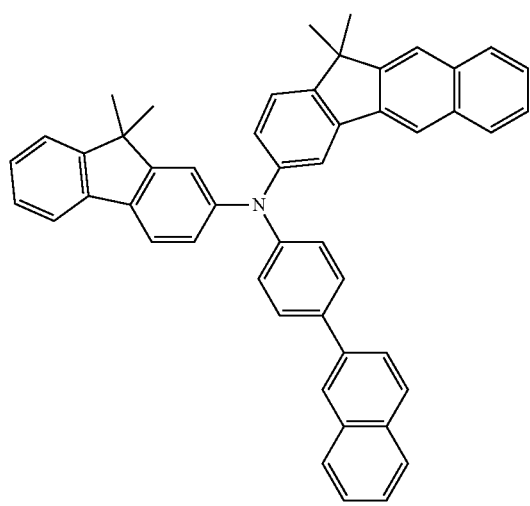
C-8
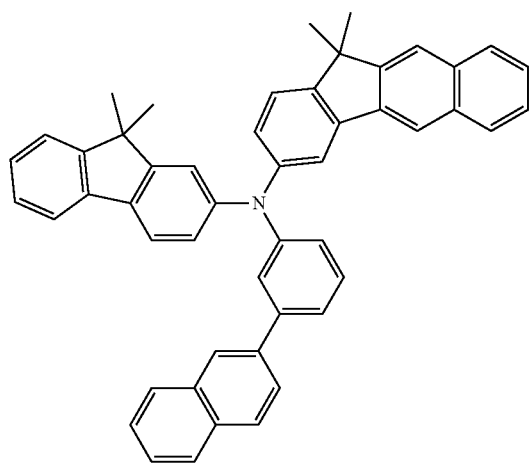
C-9
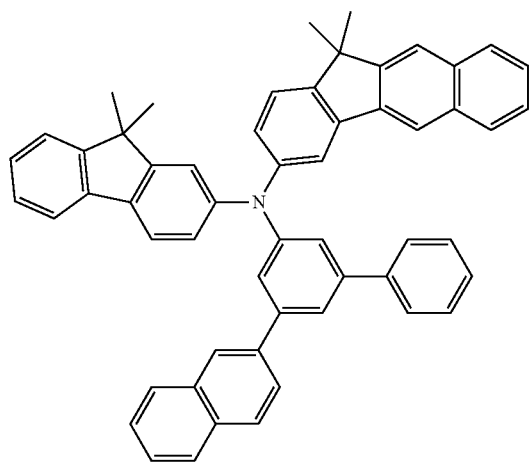
C-10
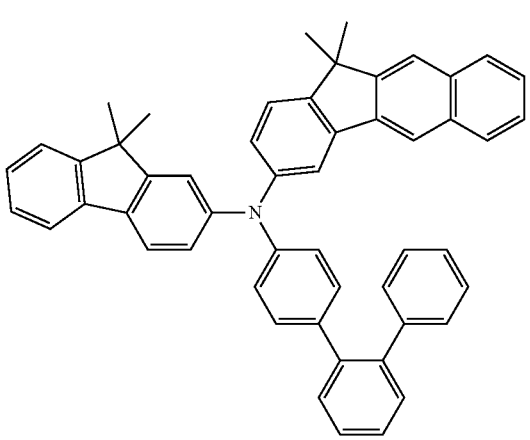
C-11
C-12
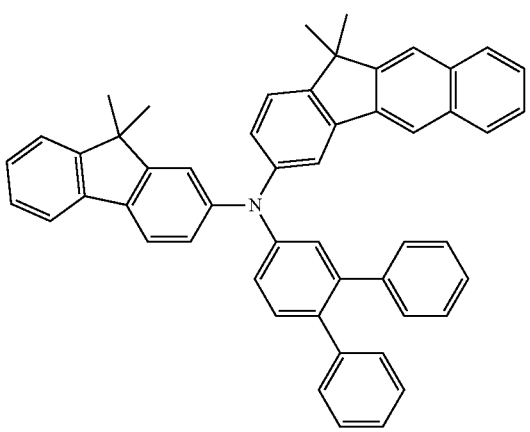

C-13
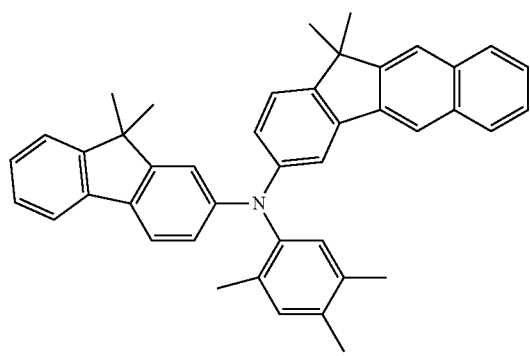
C-14
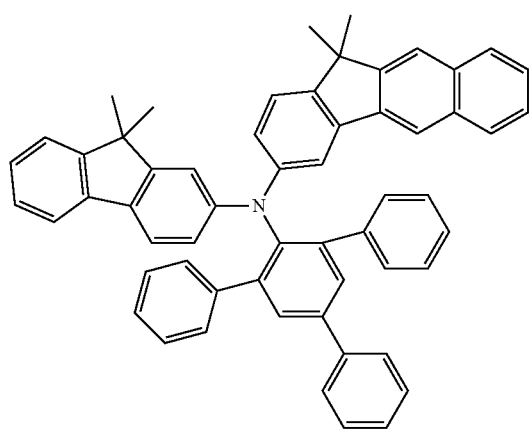
C-15
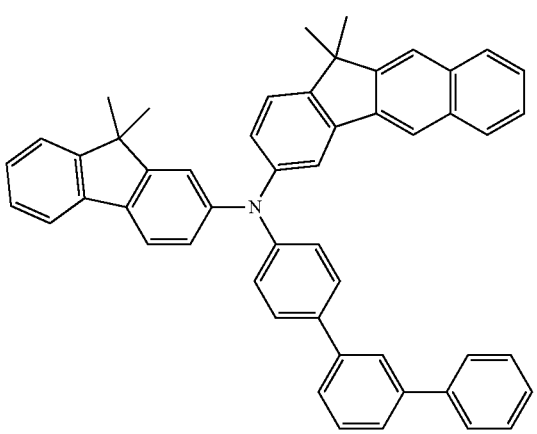
C-16
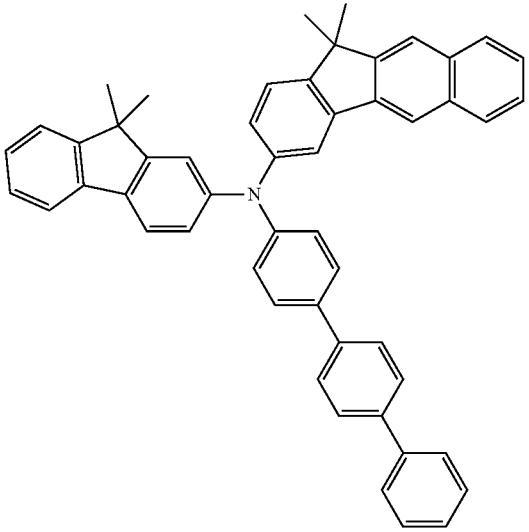
C-17
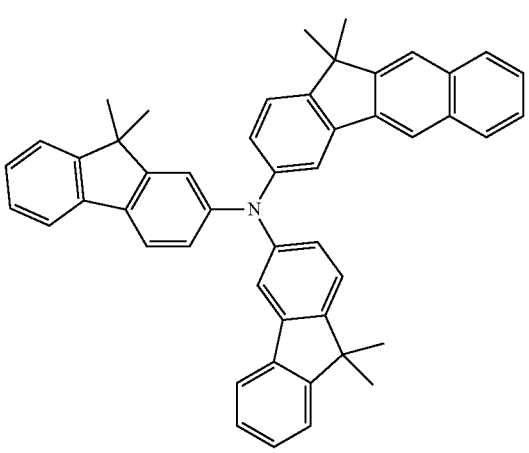
C-18
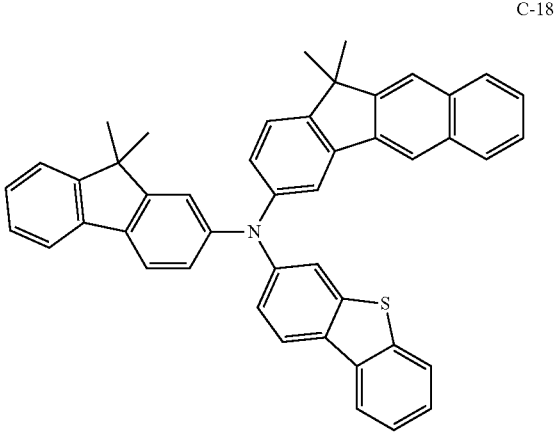

C-19
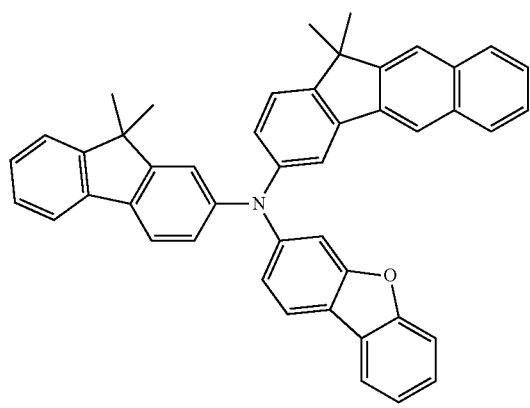
C-22
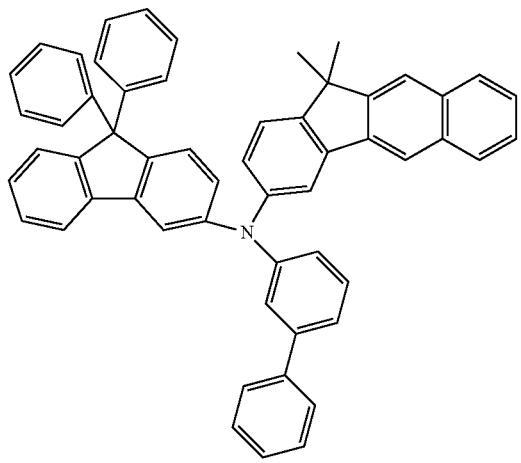
C-20
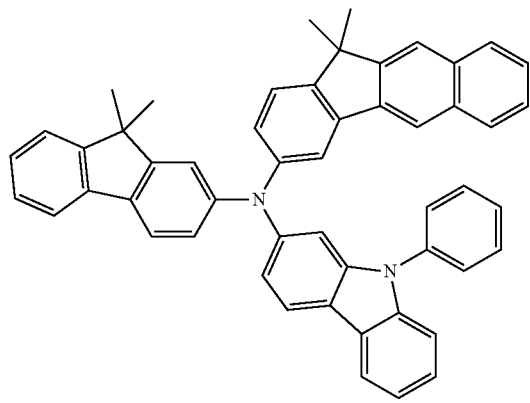
C-23
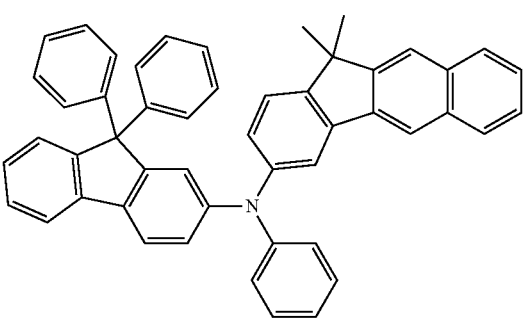
C-21
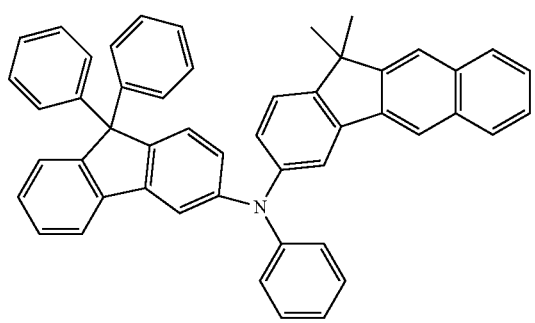
C-24
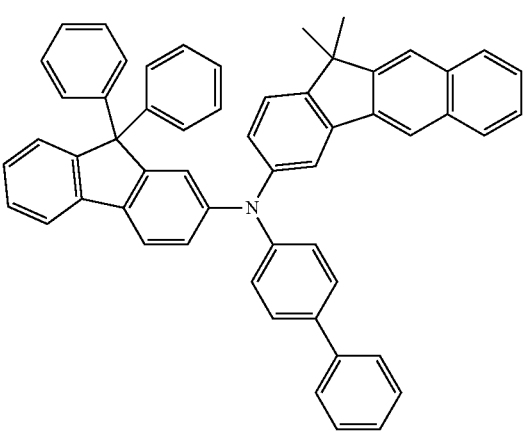

C-25
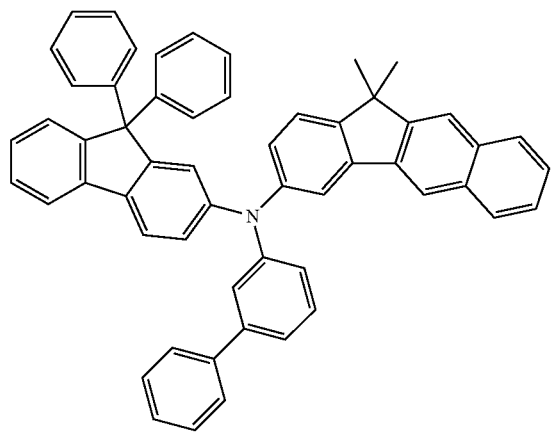
C-28
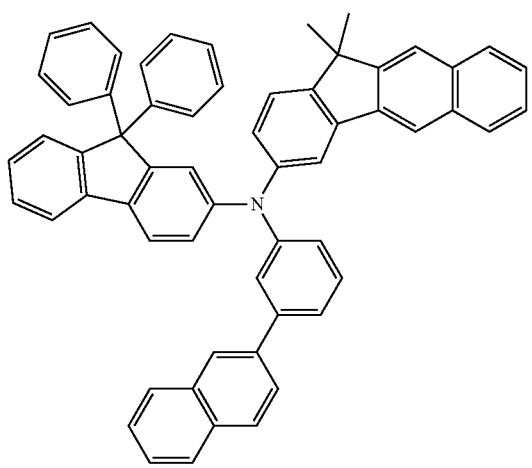
C-26
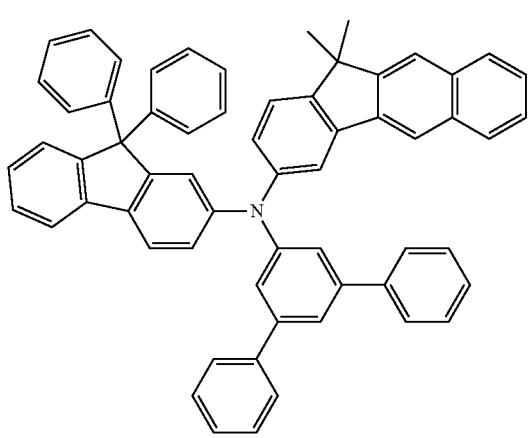
C-29
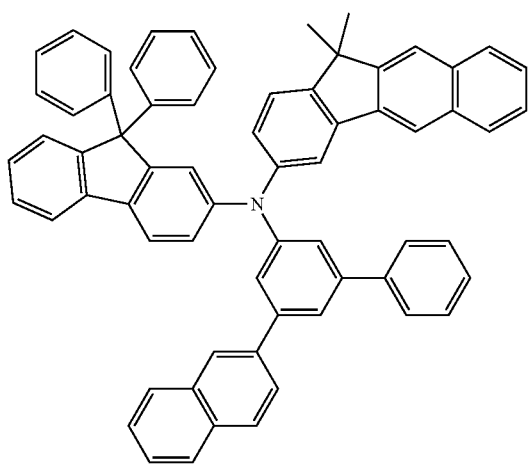
C-27
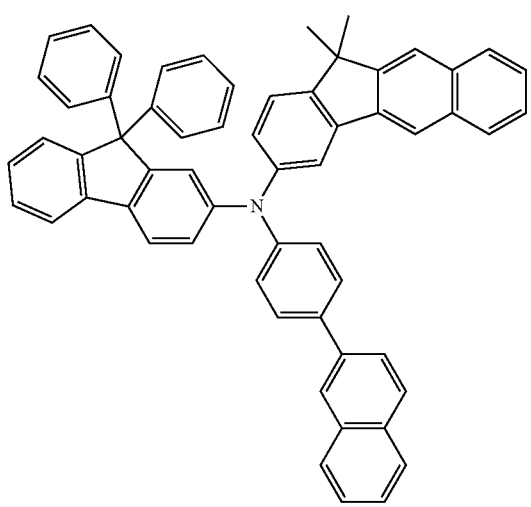
C-30
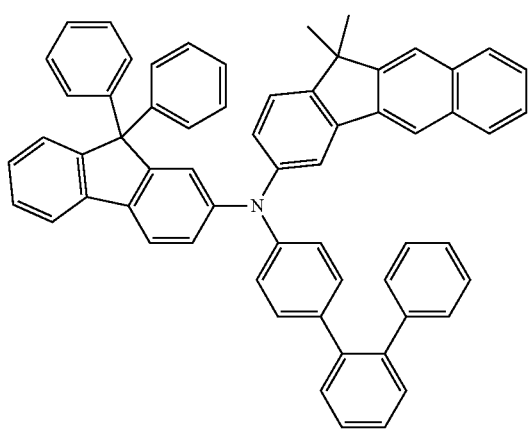

C-31
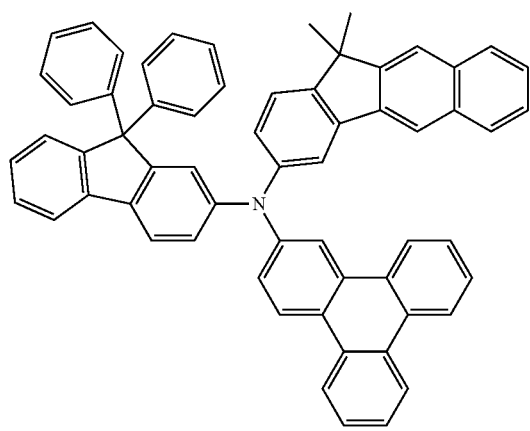
C-32
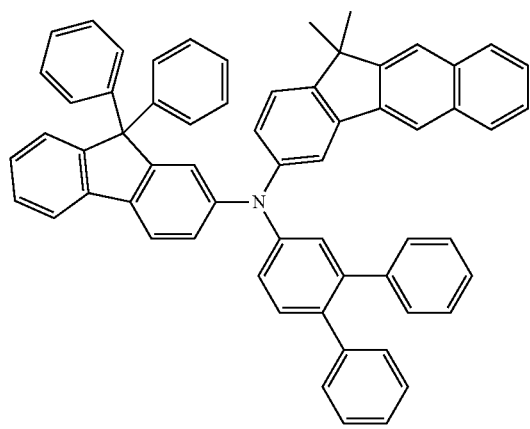
C-33
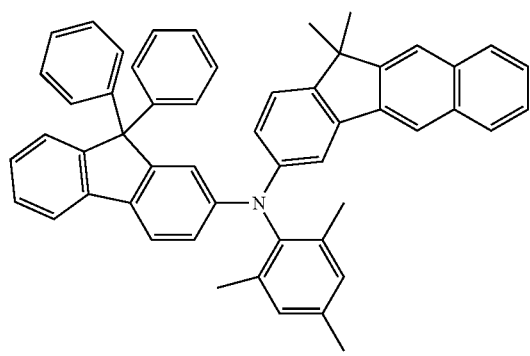
C-34
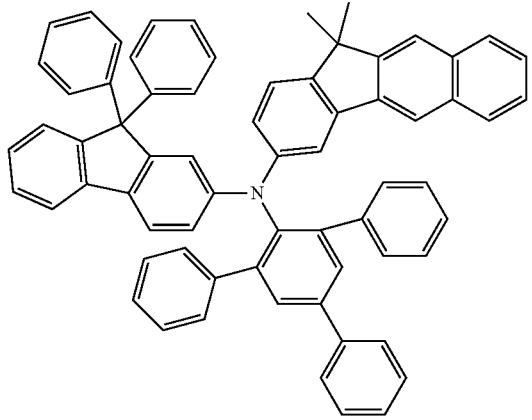
C-35
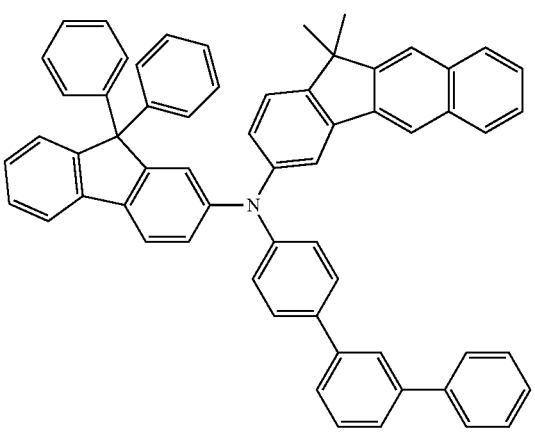
C-36
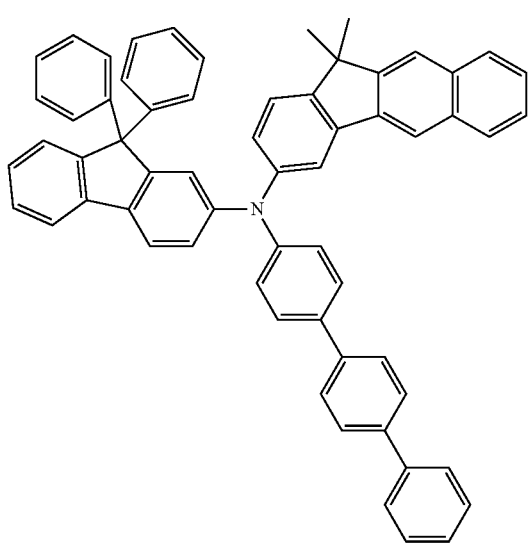

C-37
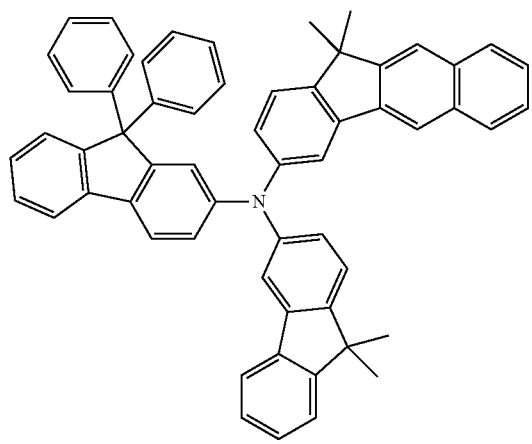
C-38
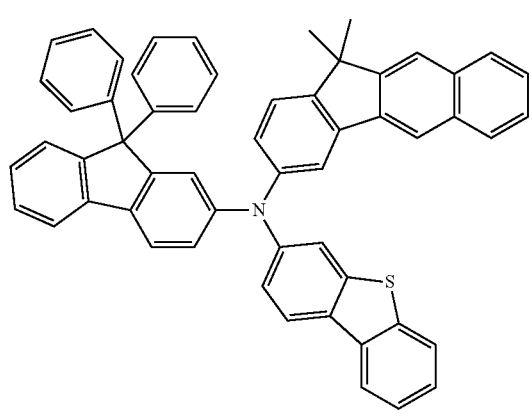
C-39
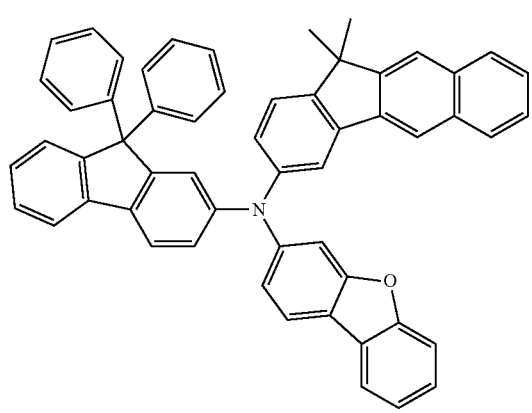
C-40
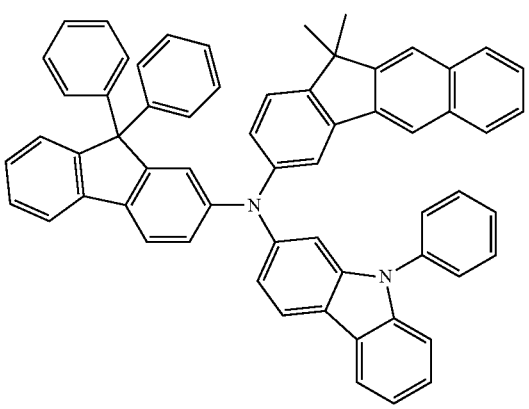
C-41
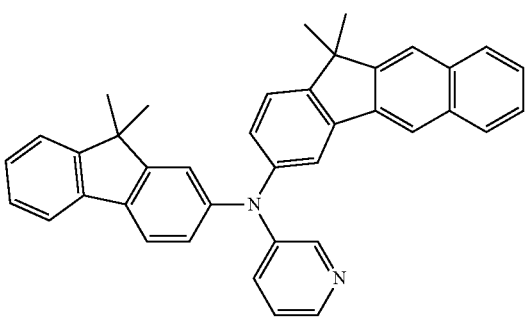
C-42
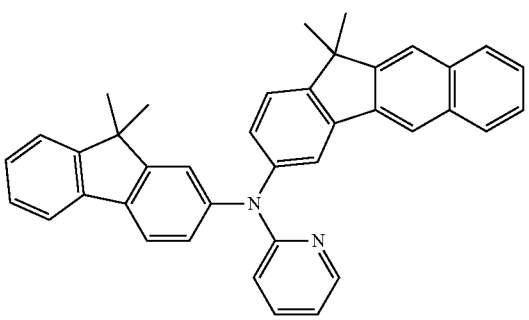
C-43
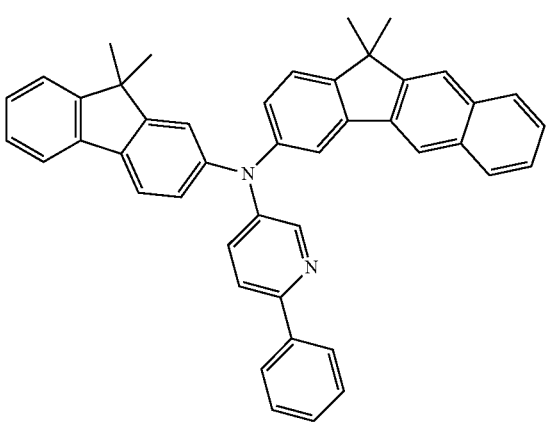

C-44
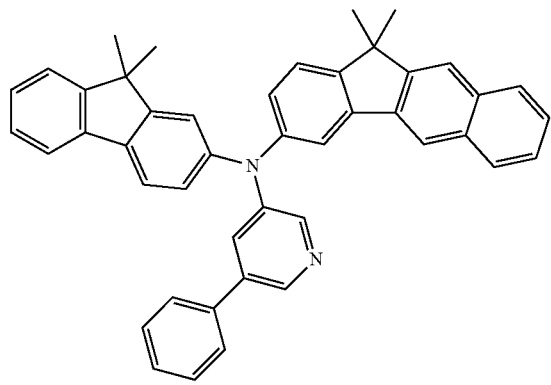
C-45
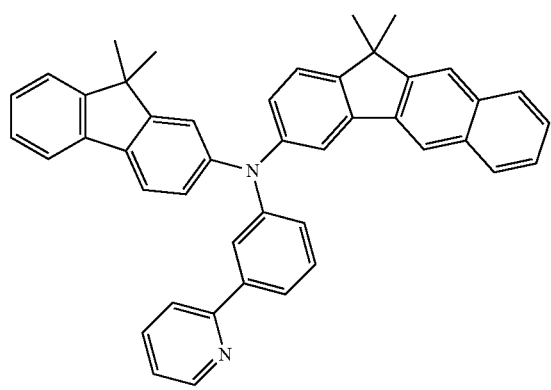
C-46
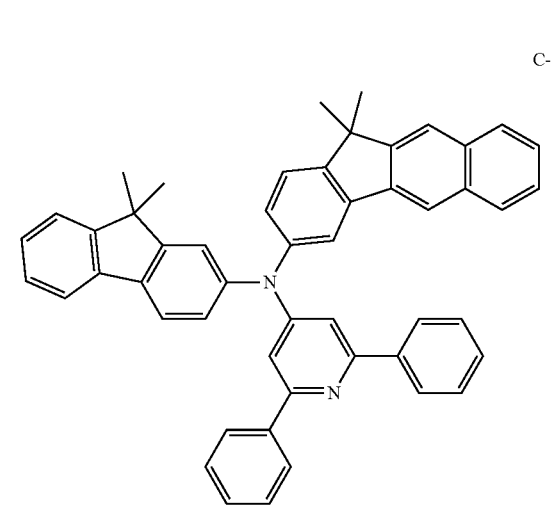
C-47
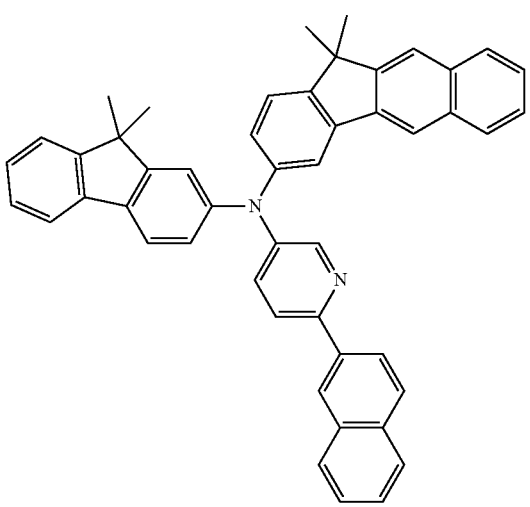
C-48
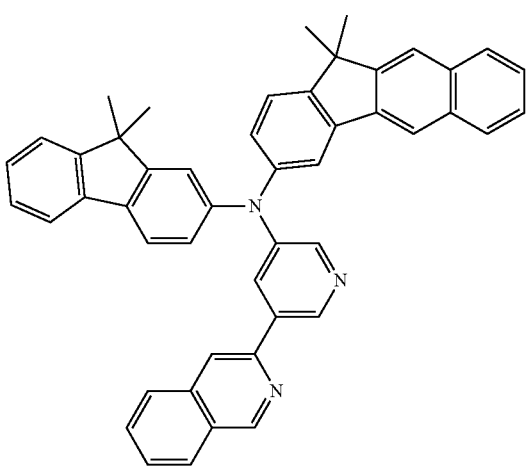
C-49
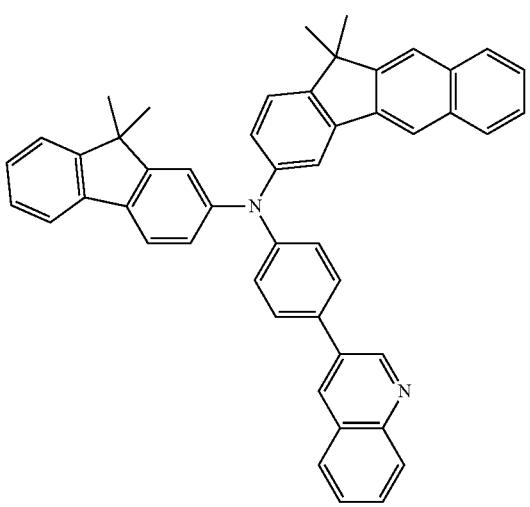

C-50
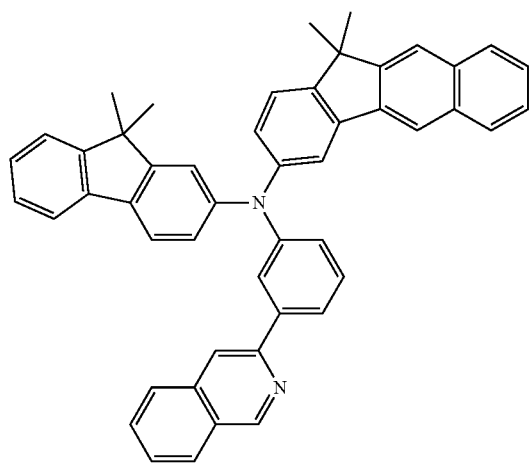
C-51
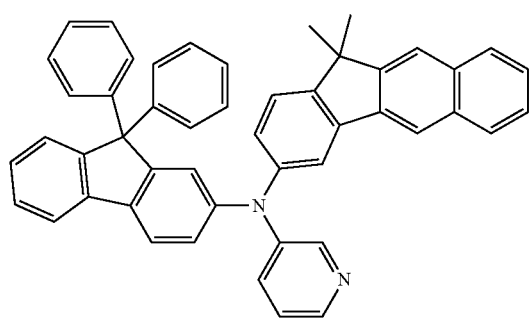
C-52
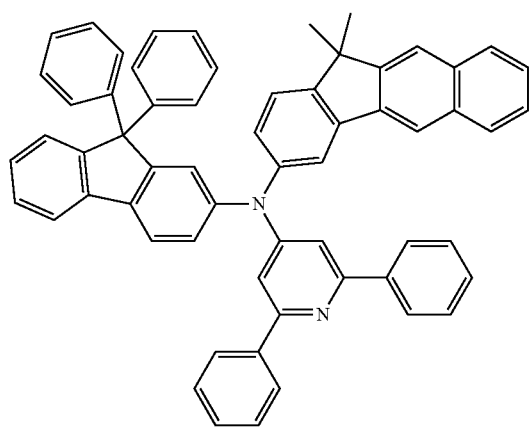
C-53
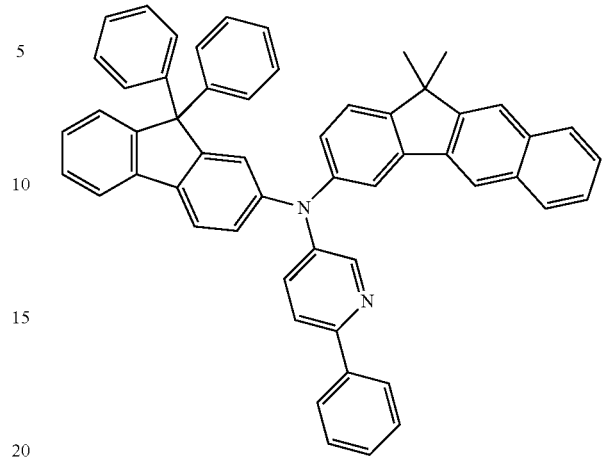
C-54
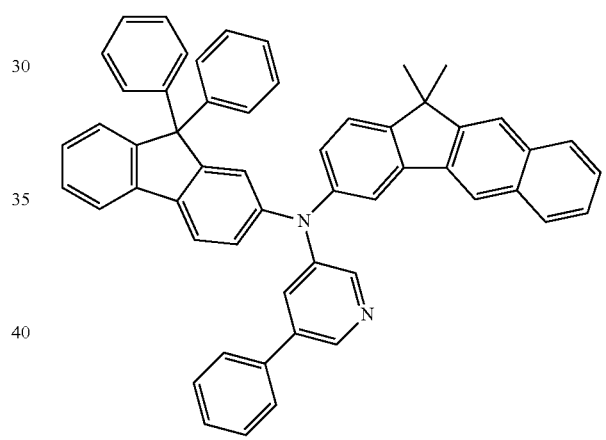
C-55
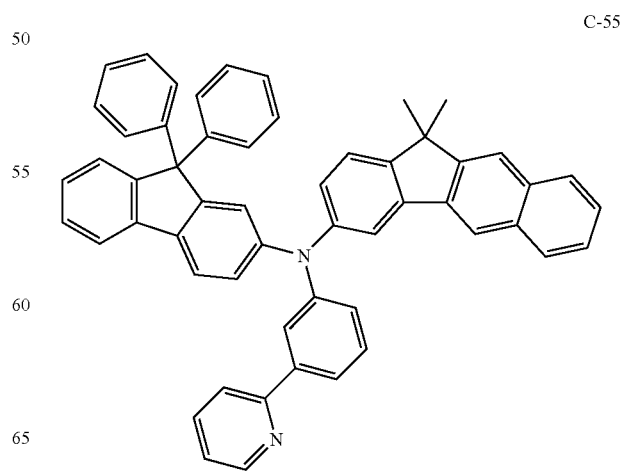

-continued

C-56

C-57

C-58

-continued

C-59

C-60

C-61

C-62

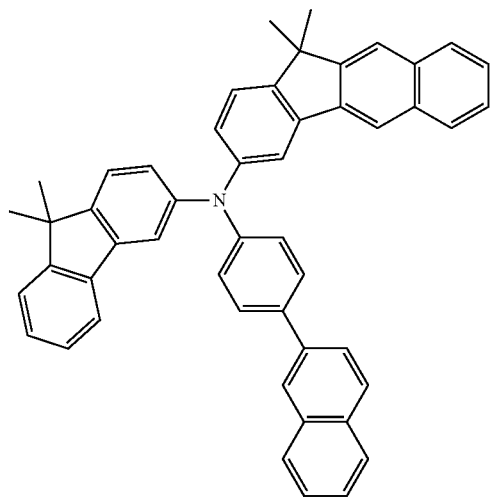
C-63
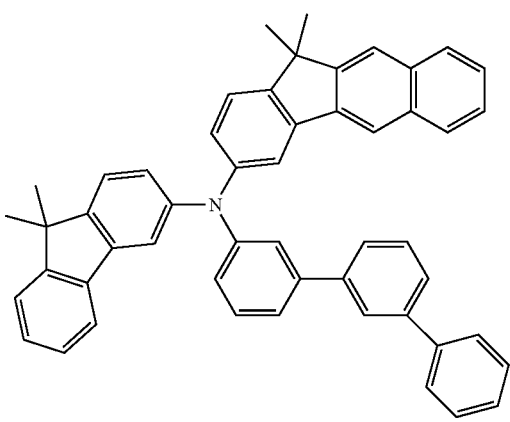
C-64
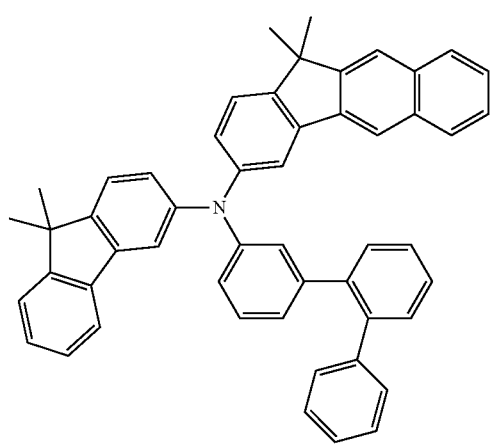
C-65
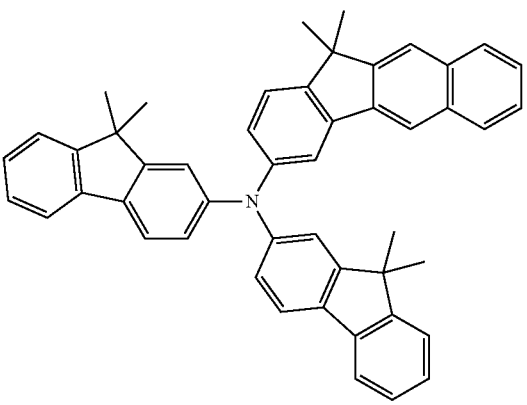
C-66
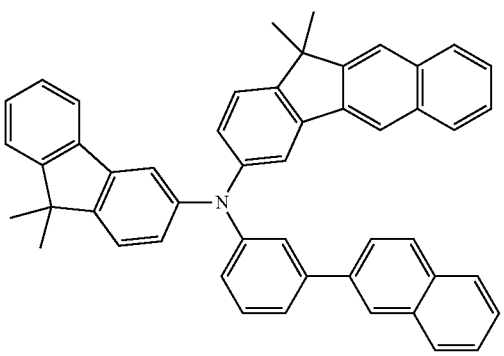
C-67
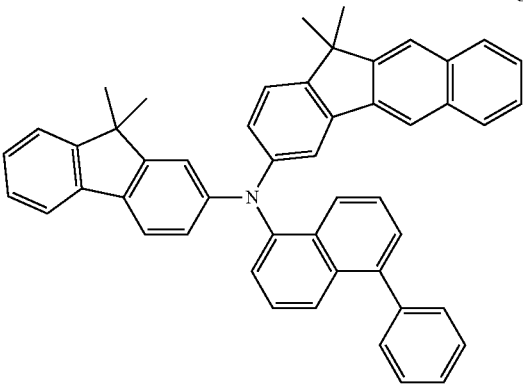
C-68
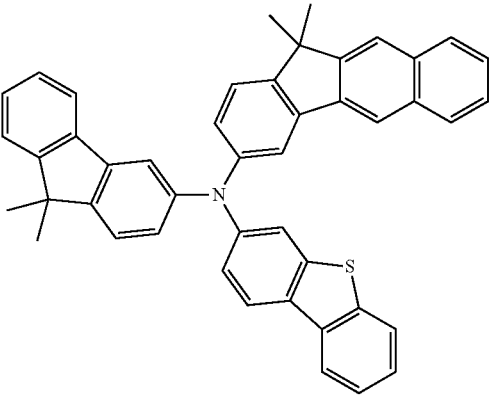
C-69

-continued

C-70
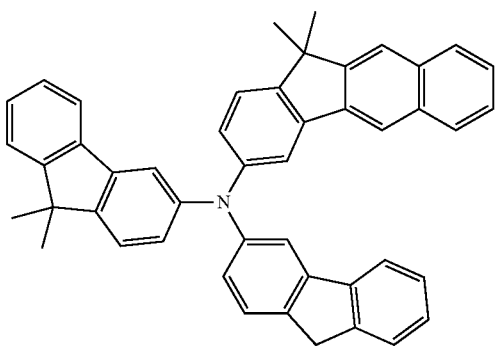

C-71
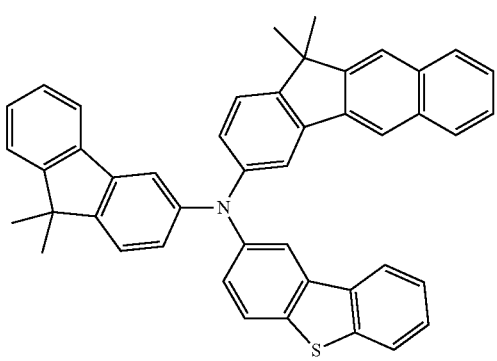

C-72
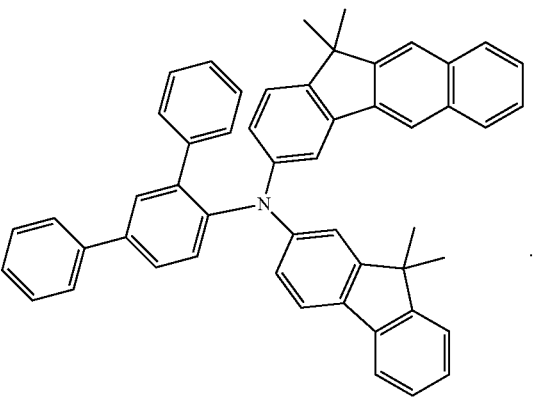

The compound of formula (1) according to the present disclosure can be prepared by a synthetic method known to a person skilled in the art. For example, it can be prepared according to the following reaction scheme 1, but is not limited thereto:

[Reaction Scheme 1]

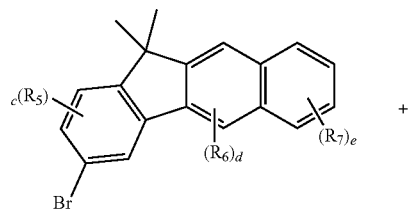

-continued

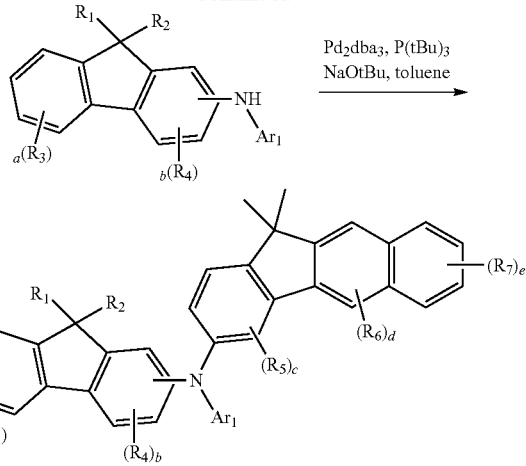

wherein $Ar_1$, $R_1$ to $R_7$, and a to e are as defined in formula 1.

The present disclosure may provide an organic electroluminescent material comprising at least one organic electroluminescent compound represented by formula 1, and an organic electroluminescent device comprising the organic electroluminescent material. According to one embodiment of the present disclosure, a hole transport material comprising at least one compound represented by formula 1 may be provided.

The organic electroluminescent material may include the organic electroluminescent compound according to the present disclosure alone, or may further include conventional materials used in organic electroluminescent materials.

The present disclosure may provide an organic electroluminescent device comprising at least one organic electroluminescent compound represented by formula 1. According to one embodiment of the present disclosure, the organic electroluminescent device may comprise at least one compound represented by formula 1 in a hole transport zone, or in at least one layer of a plurality of hole transport layers.

A host compound which can be used in combination with the compound of the present disclosure includes the compound represented by any one of the following formulas 11 to 13, but is not limited thereto:

(11)
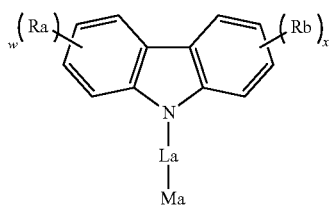

(12)
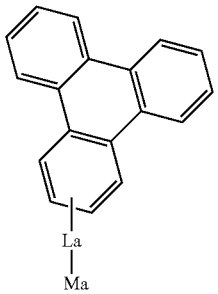

-continued

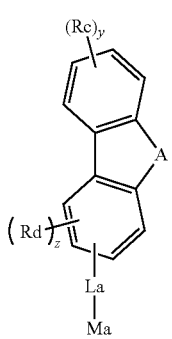
(13)

wherein
Ma represents a substituted or unsubstituted (C6-C30) aryl, a substituted or unsubstituted mono- or di-(C6-C30)arylamino, or a substituted or unsubstituted (3- to 30-membered) heteroaryl;
La represents a single bond, a substituted or unsubstituted (C6-C30)arylene, or a substituted or unsubstituted (3- to 30-membered)heteroarylene;
A represents S, O, N(Re), or C(Rf)(Rg);
Ra to Rd each independently represent hydrogen, deuterium, a halogen, a cyano, a substituted or unsubstituted (C1-C30)alkyl, a substituted or unsubstituted (C2-C30) alkenyl, a substituted or unsubstituted (C2-C30)alkynyl, a substituted or unsubstituted (C3-C30)cycloalkyl, a substituted or unsubstituted (C6-C60)aryl, a substituted or unsubstituted (3- to 30-membered)heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi (C6-C30)arylsilyl, a substituted or unsubstituted (C1-C30)alkyl(C6-C30)arylamino, or a substituted or unsubstituted mono- or di-(C6-C30)arylamino; or are linked to an adjacent substituent(s) to form a substituted or unsubstituted, mono- or polycyclic, 3- to 30-membered alicyclic or aromatic ring, or a combination thereof, in which the formed ring may contain at least one heteroatom selected from nitrogen, oxygen, and sulfur;
Re to Rg each independently represent hydrogen, deuterium, a halogen, a cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl (C6-C30)arylamino; or Rf and Rg are linked to each other to form a substituted or unsubstituted, mono- or polycyclic, 3- to 30-membered alicyclic or aromatic ring, or a combination thereof, in which the formed ring may contain at least one heteroatom selected from nitrogen, oxygen, and sulfur;
w to y each independently represent an integer of 1 to 4, and z represents an integer of 1 to 3; and
the heteroaryl(ene) contains at least one heteroatom selected from B, N, O, S, Si, and P.

The compound represented by any one of formulas 11 to 13 includes the following compounds, but is not limited thereto:

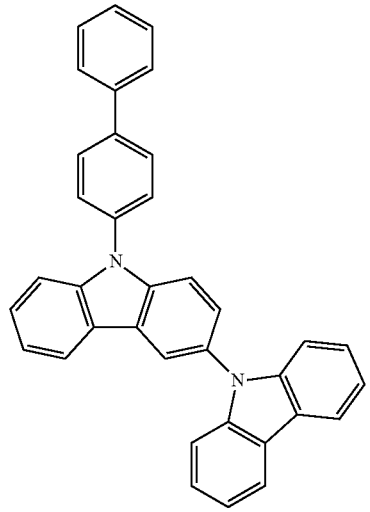
H-1

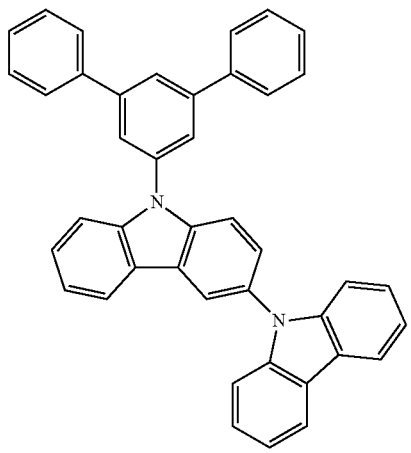
H-2

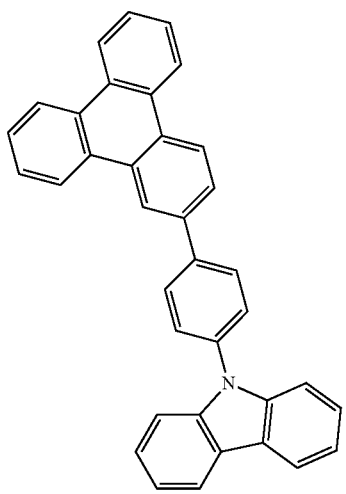
H-3

-continued
H-4
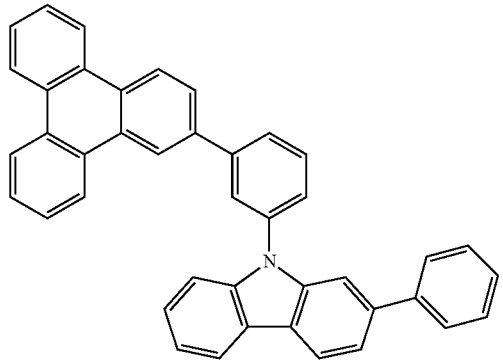
H-5
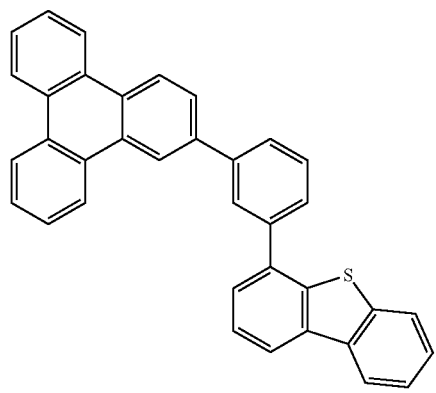
H-6
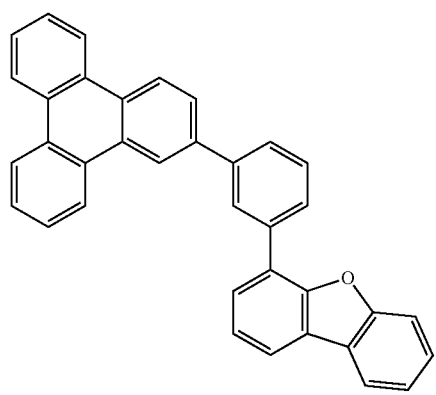
H-7
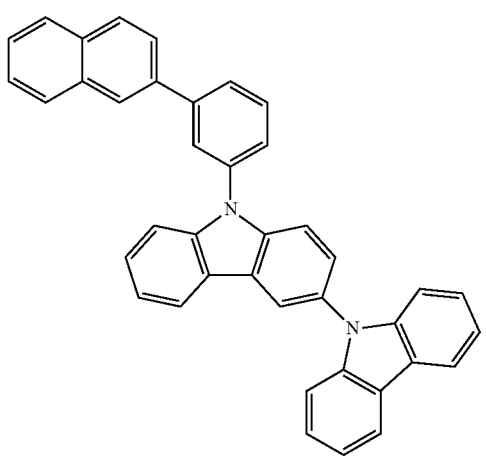
H-8
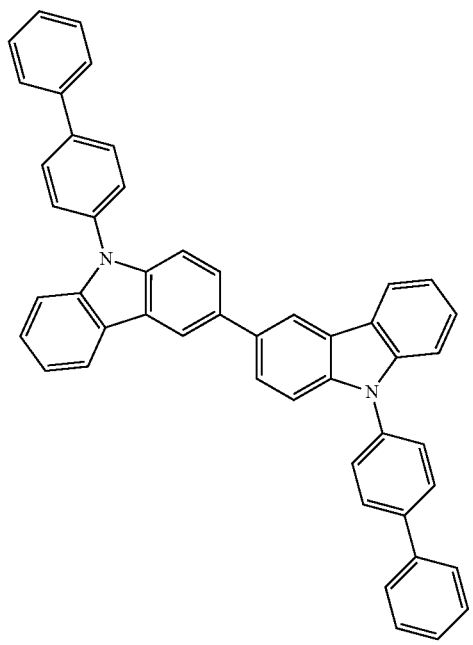
H-9
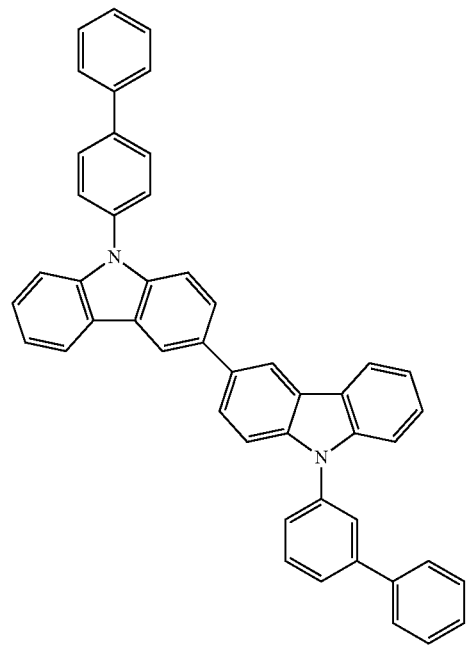

H-10
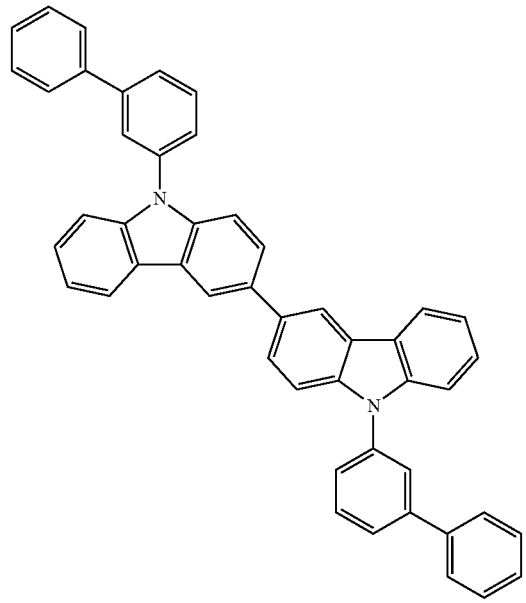
H-11
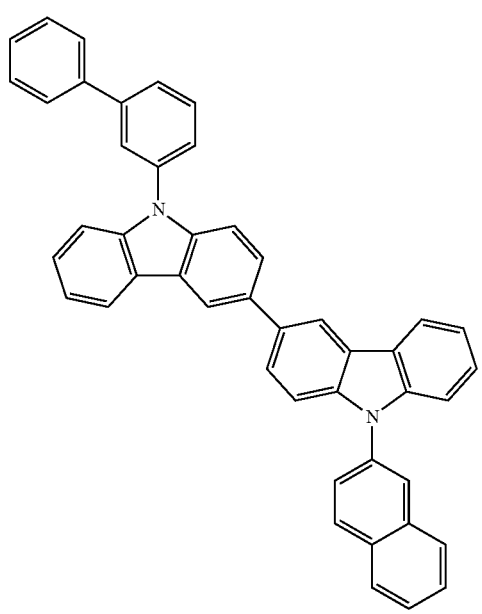
H-12
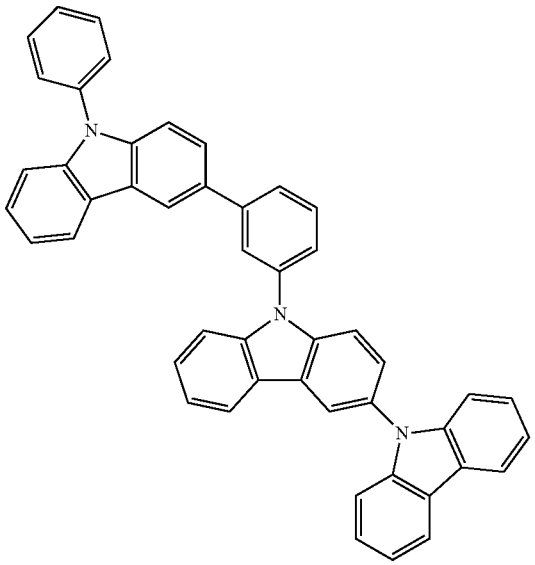
H-13
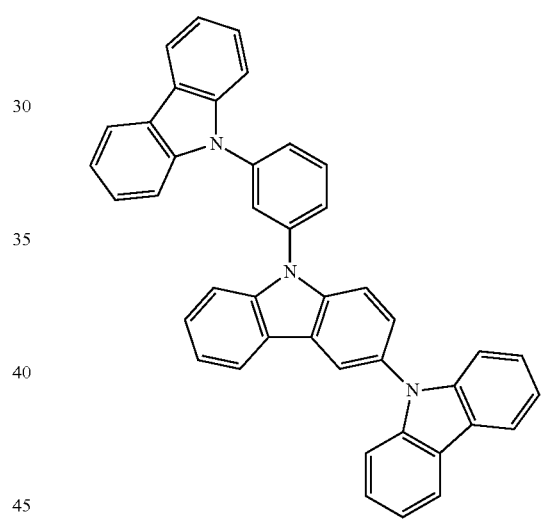
H-14
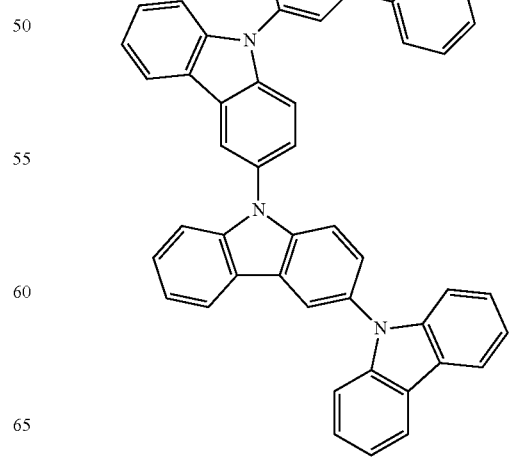

H-15
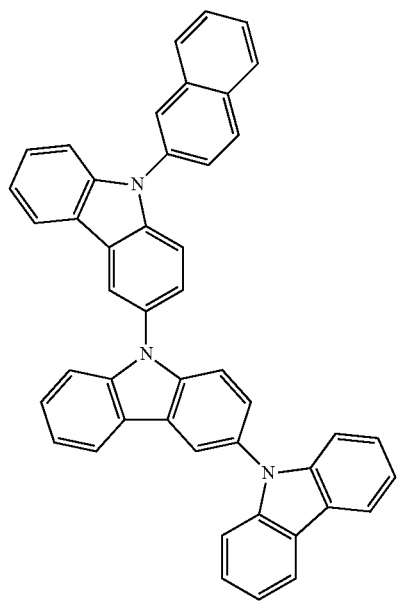
H-16
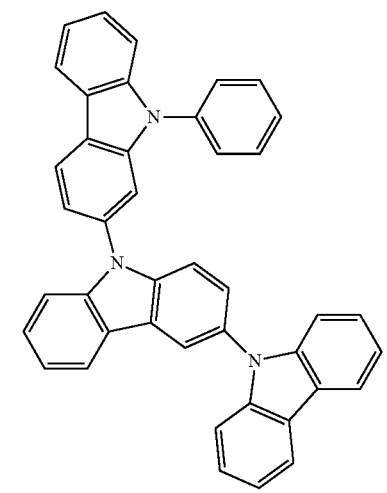
H-17
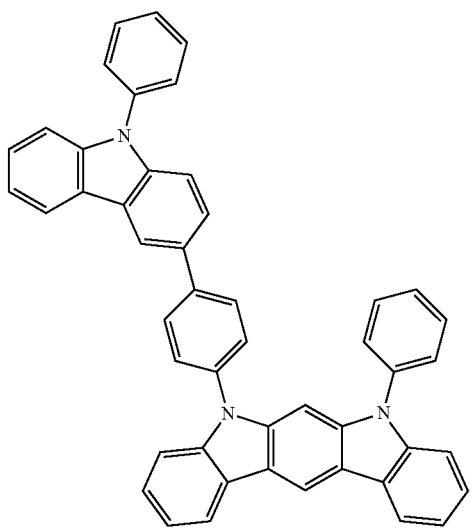
H-18
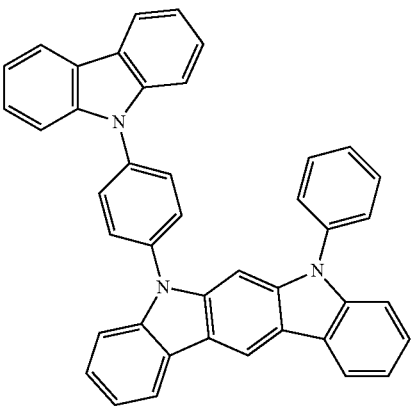
H-19
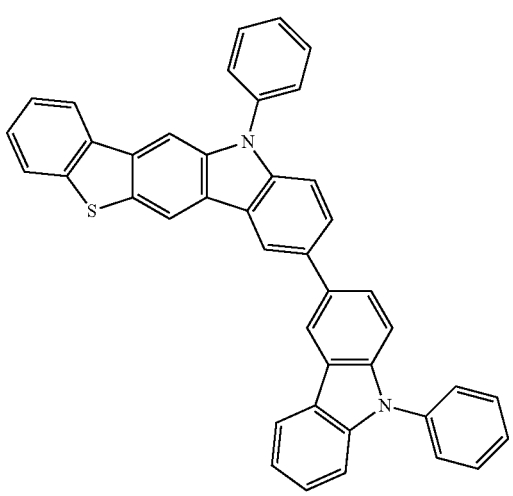
H-20
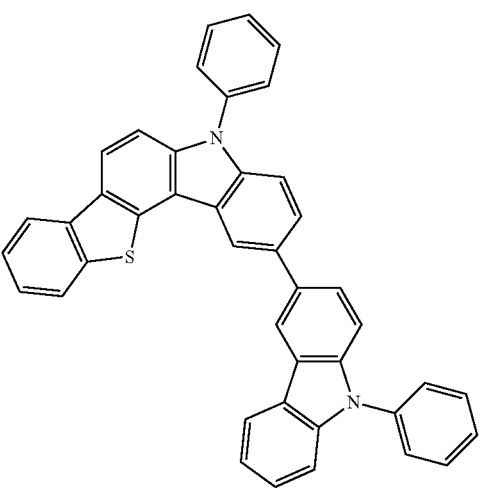

H-21
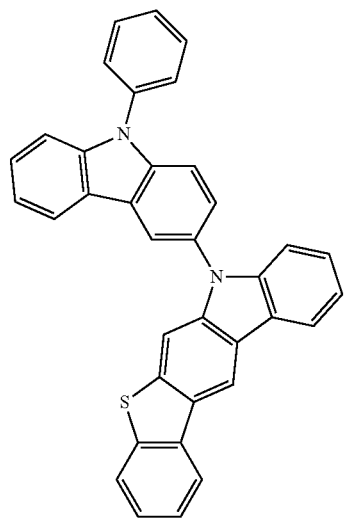
H-22
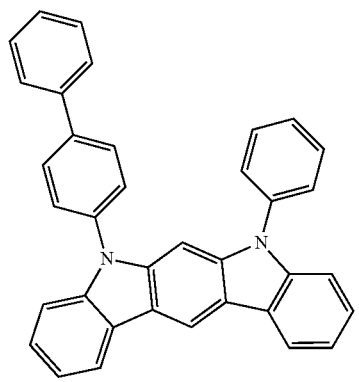
H-23
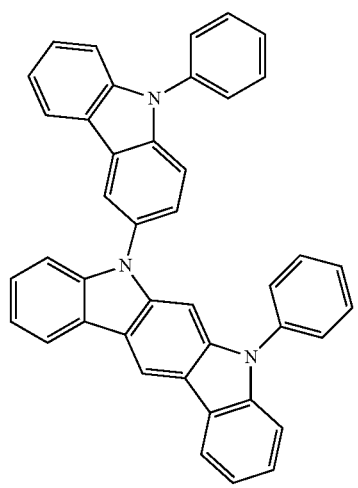
H-24
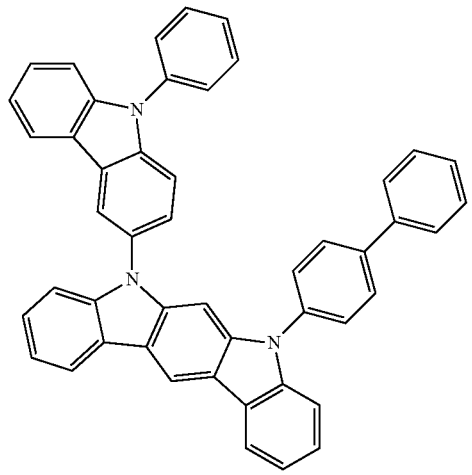
H-25
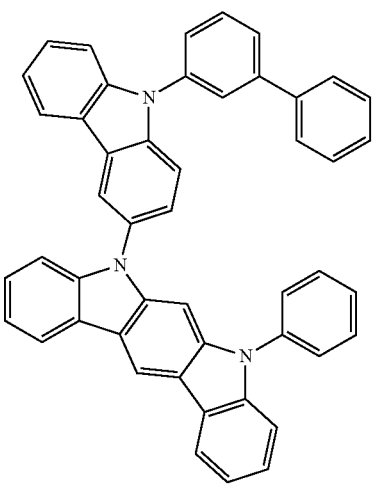
H-26
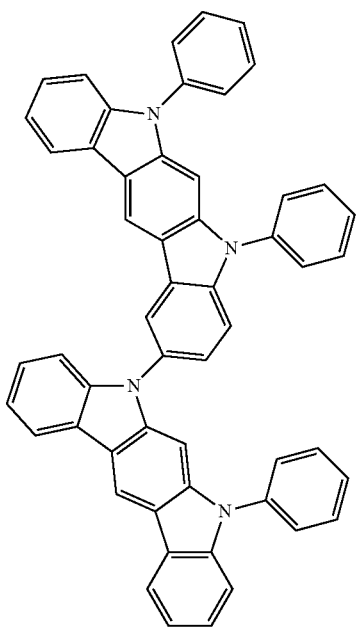

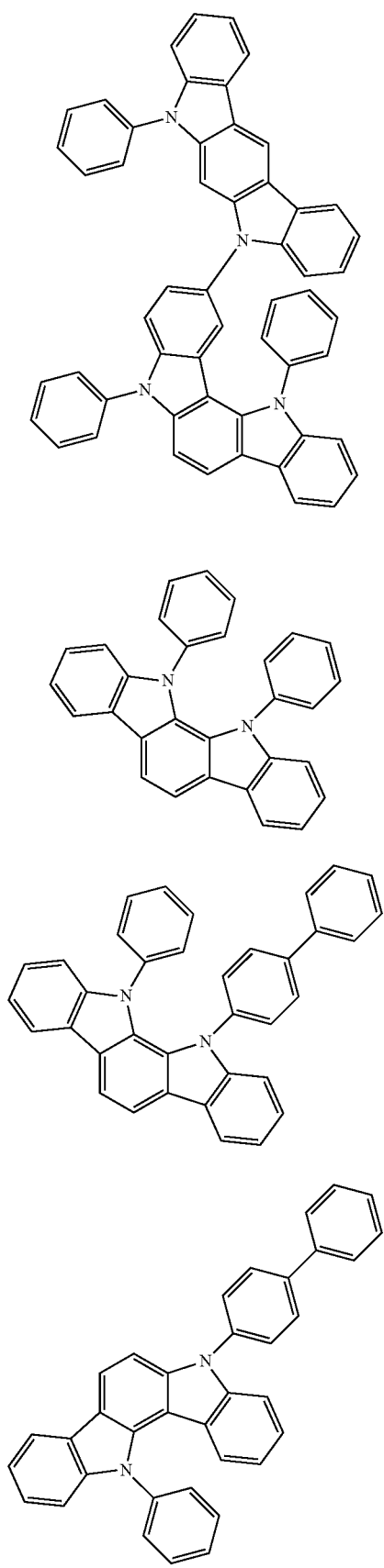
H-27
H-28
H-29
H-30
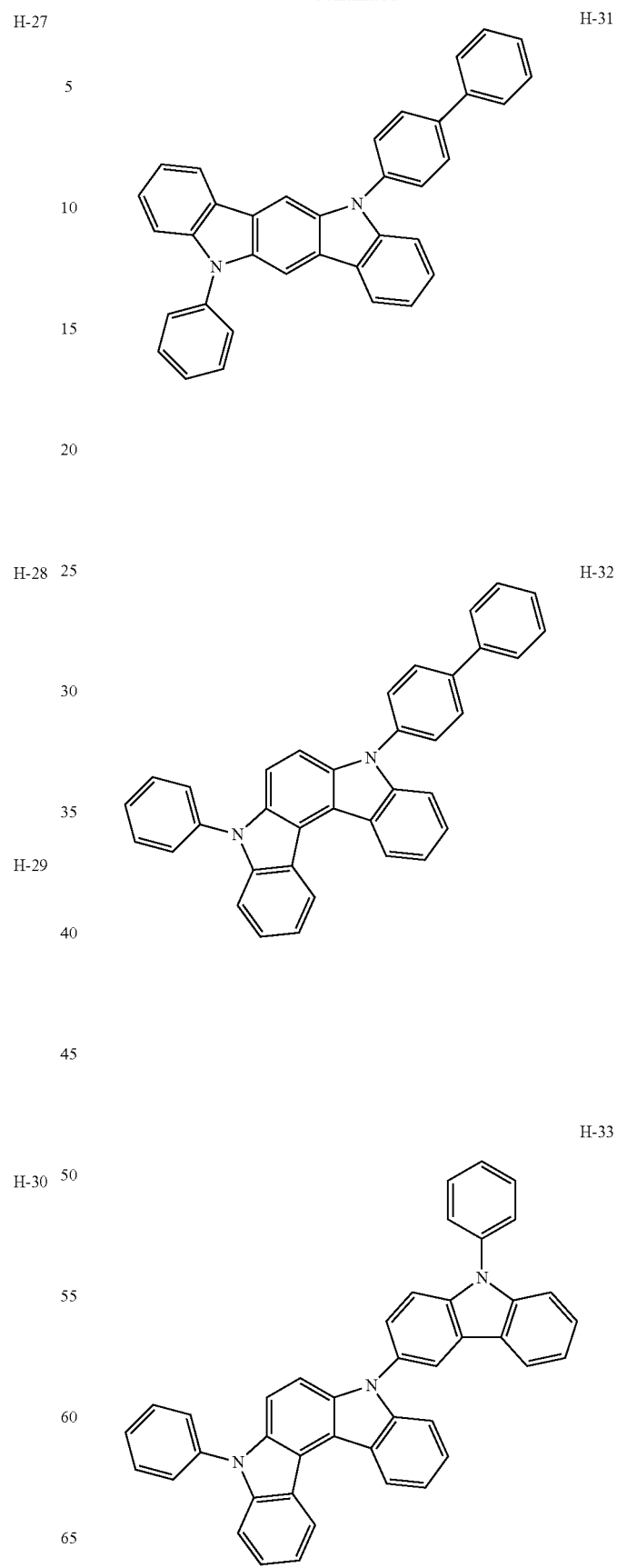
H-31
H-32
H-33

H-34
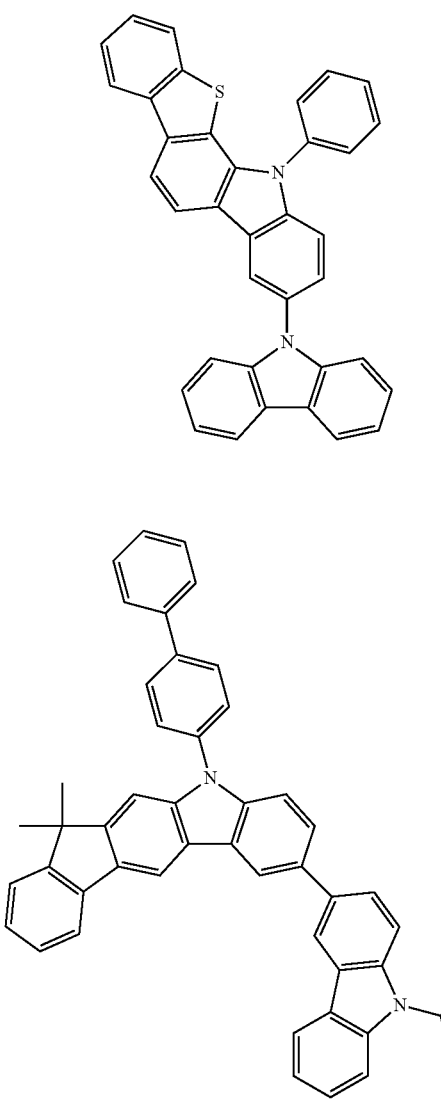
H-35
H-36
H-37
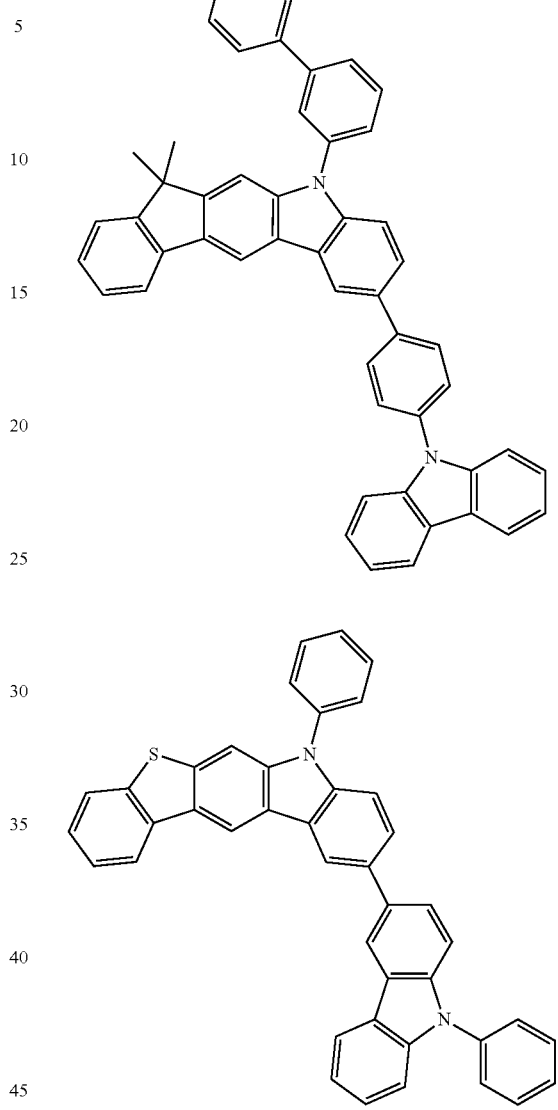
H-38
H-39
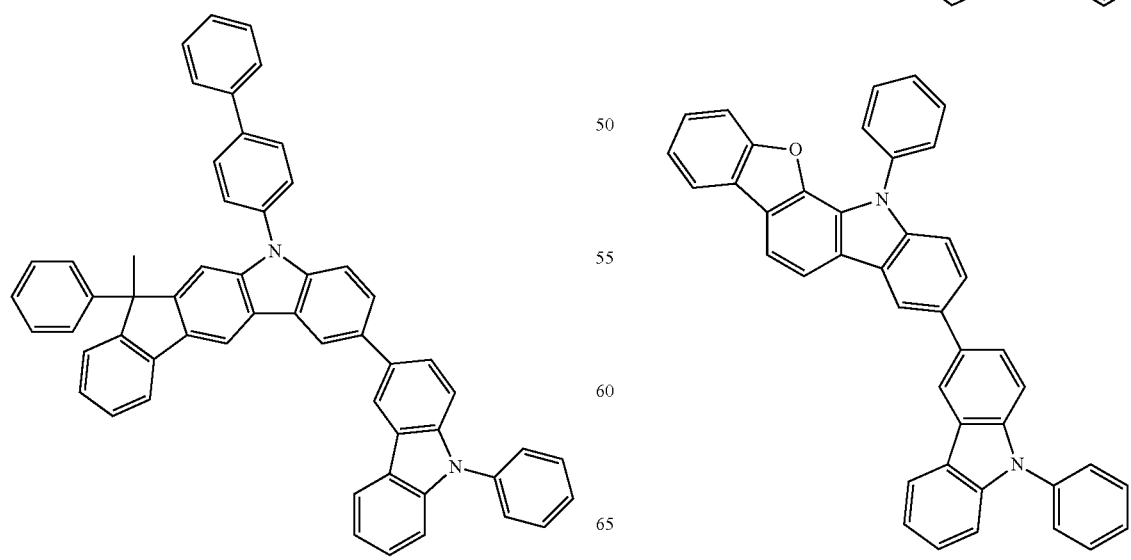

-continued
H-40
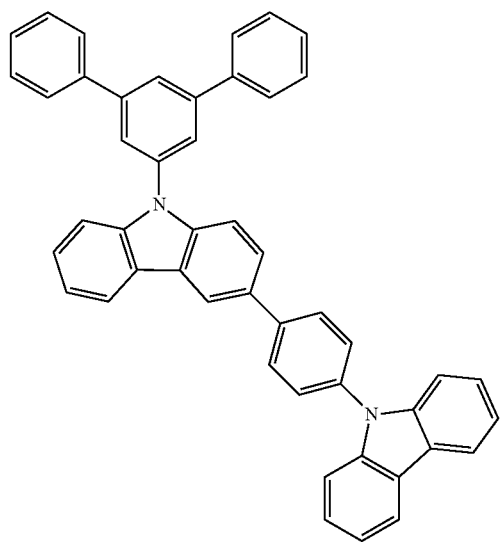
H-41
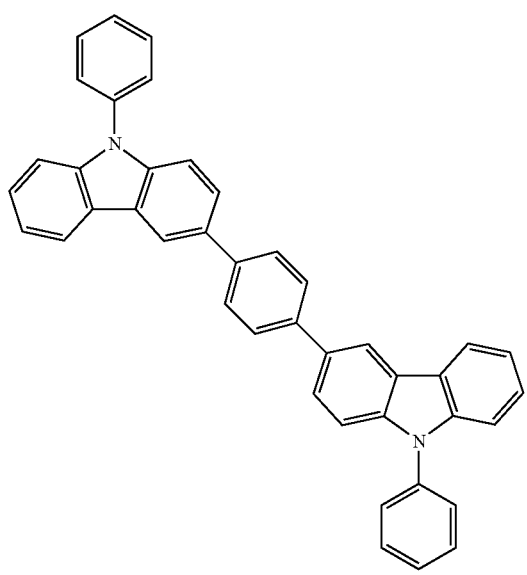
H-42
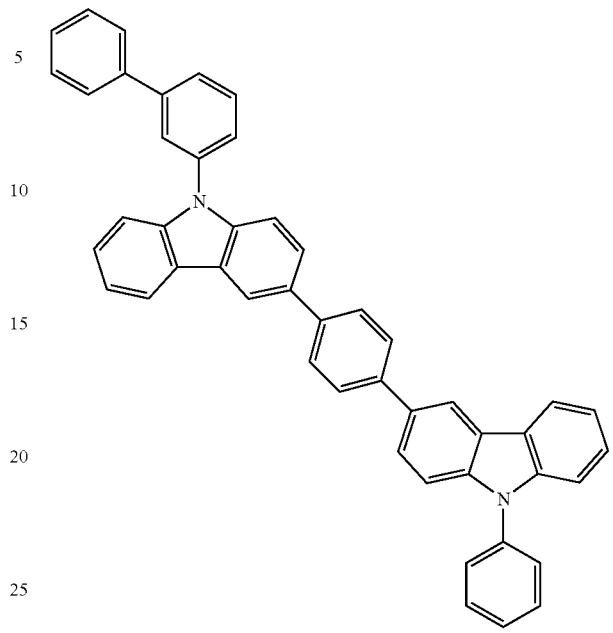
H-43
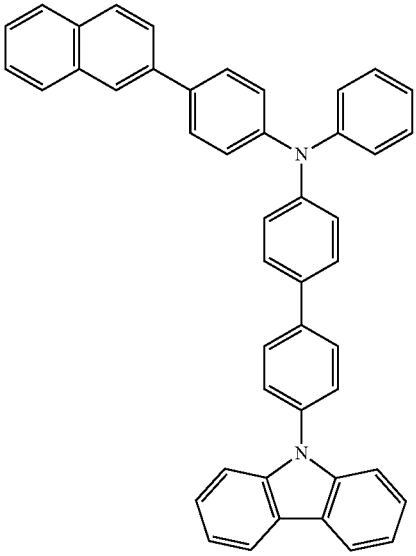

H-44
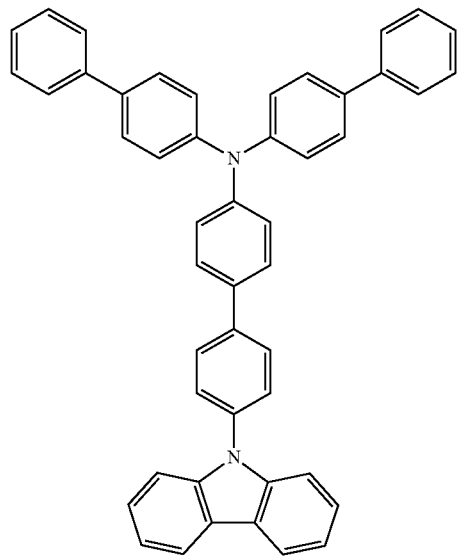
H-45
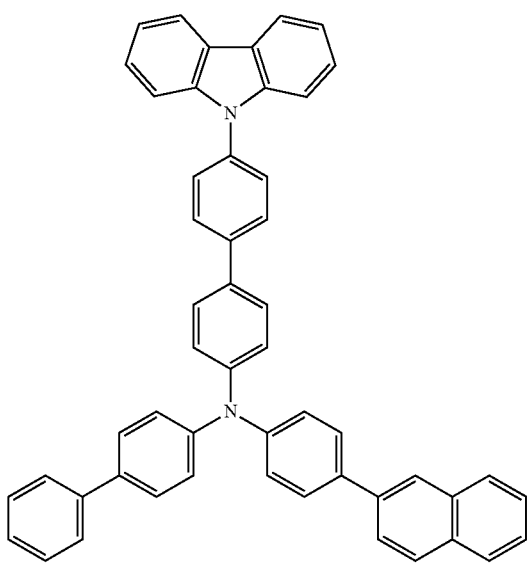
H-46
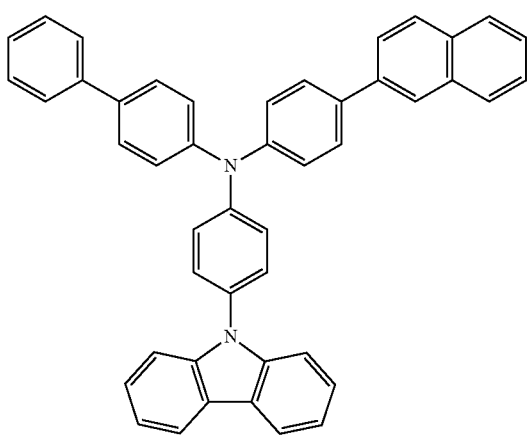
H-47
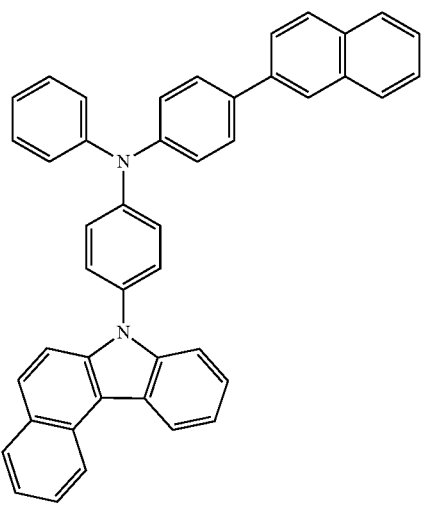
H-48
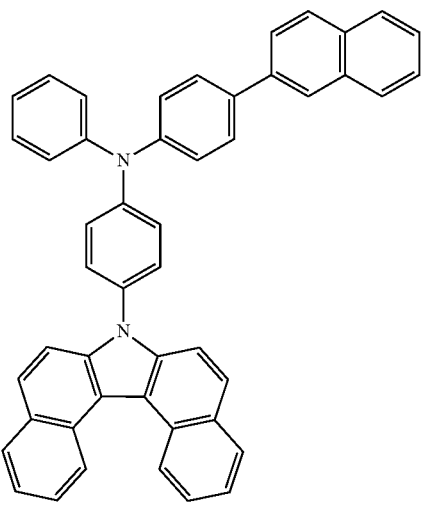
H-49
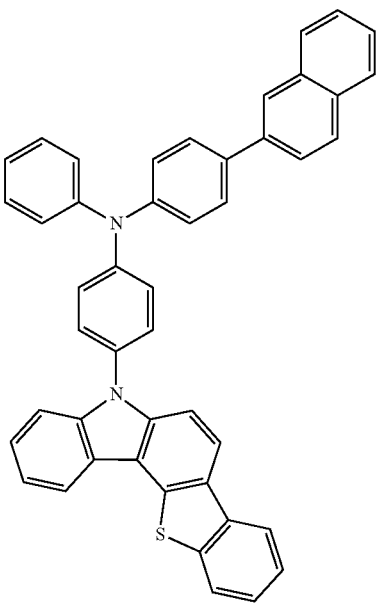

-continued
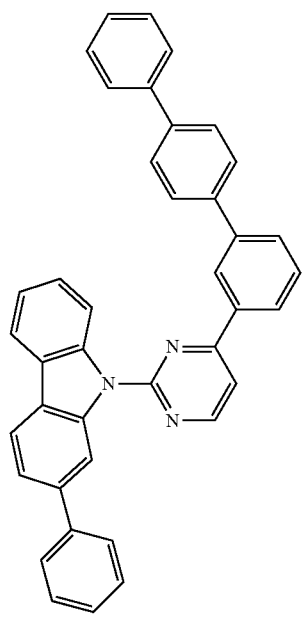
H-50
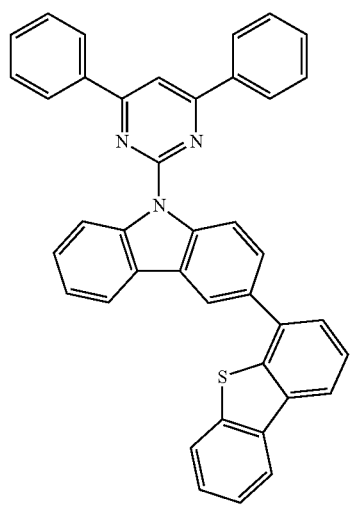
H-51
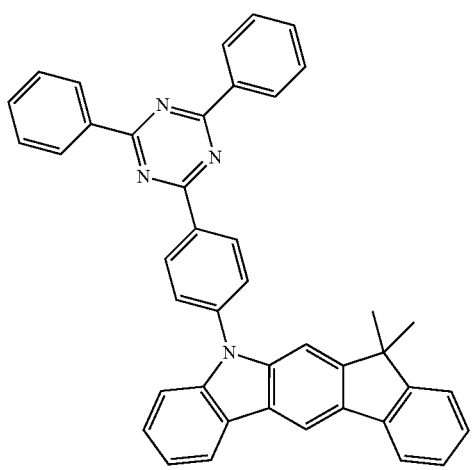
H-52
-continued
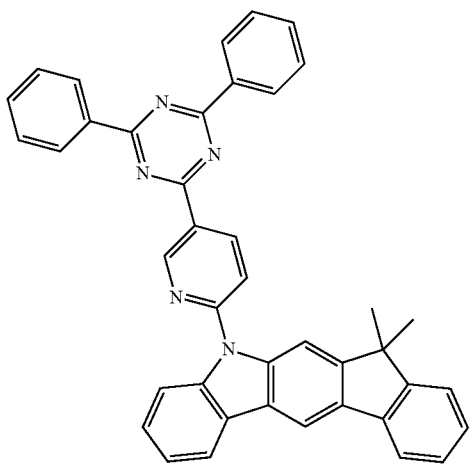
H-53
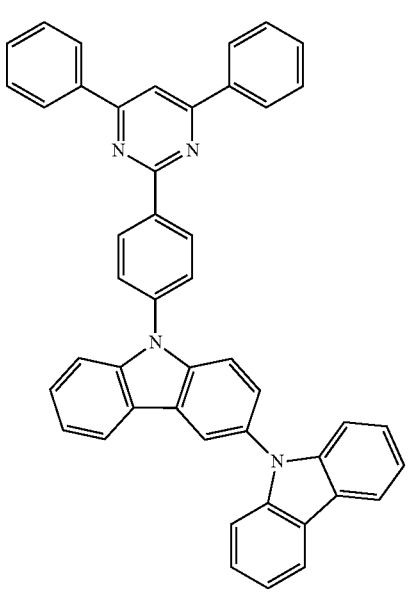
H-54
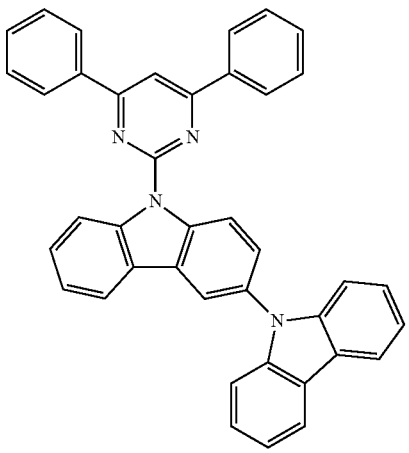
H-55

H-56
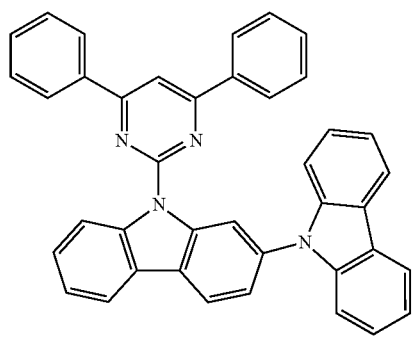
H-57
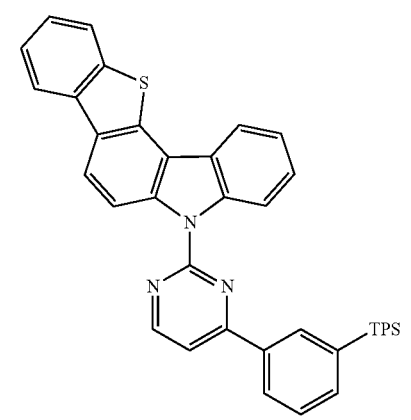
H-58
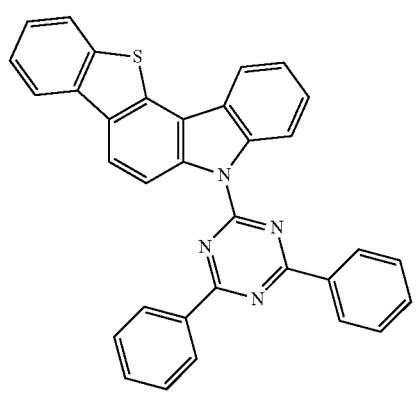
H-59
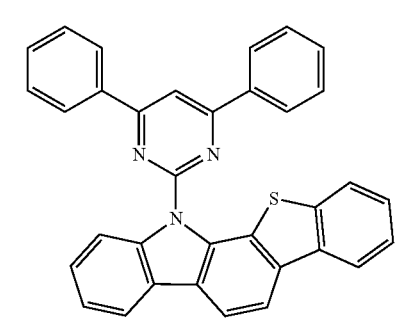
H-60
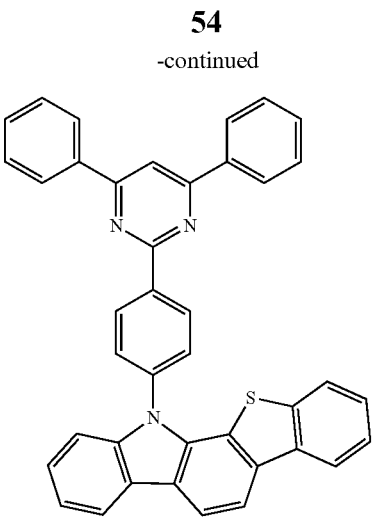
H-61
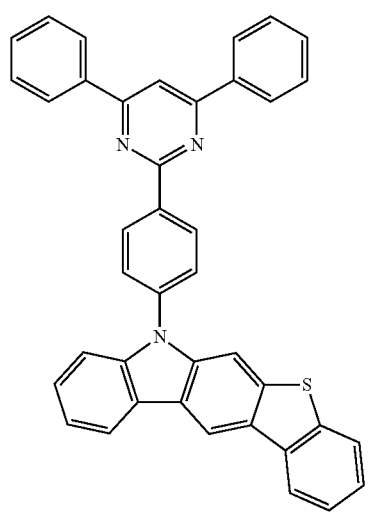
H-62
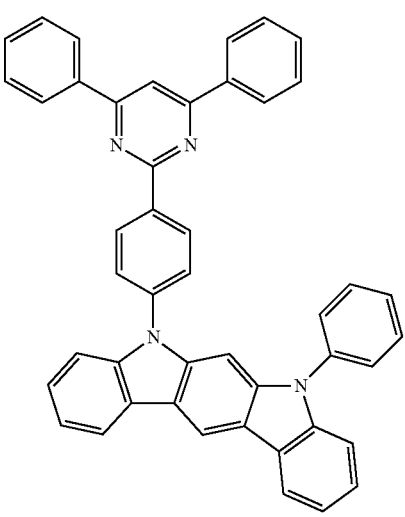

H-63
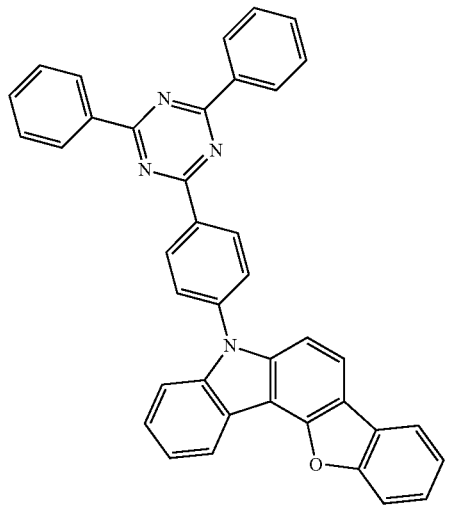
H-64
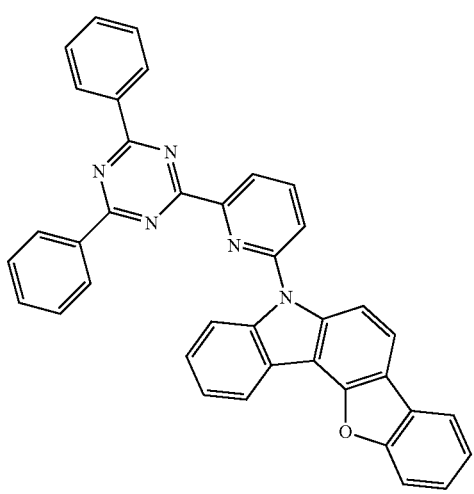
H-65
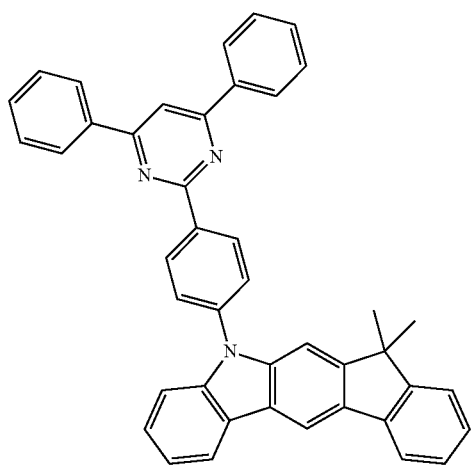
H-66
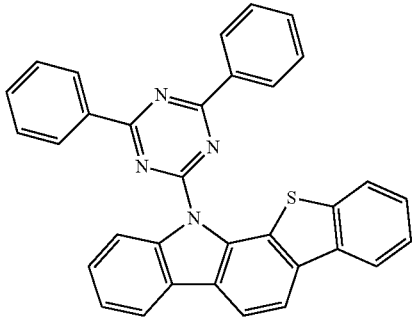
H-67
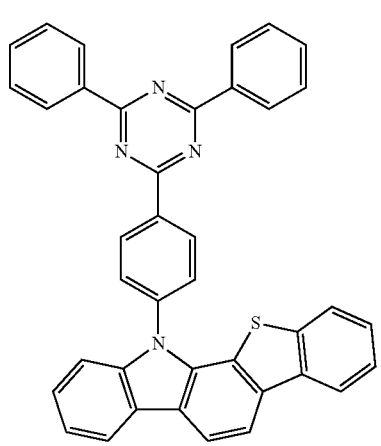
H-68
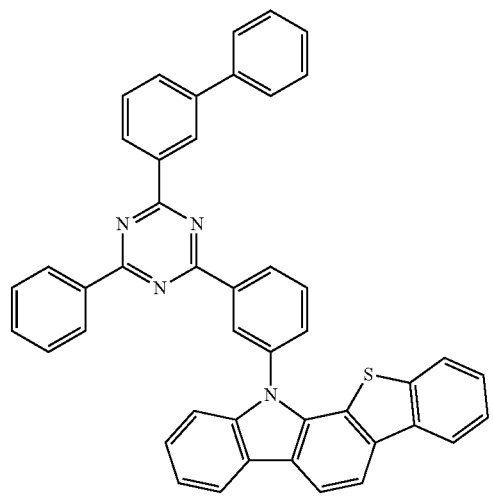

H-69
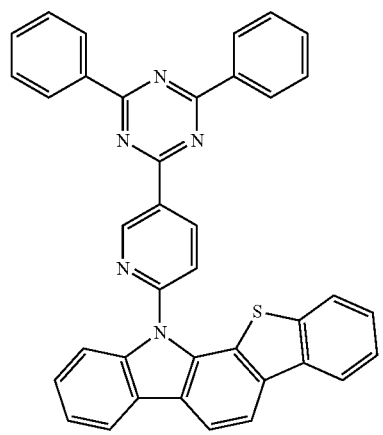
H-70
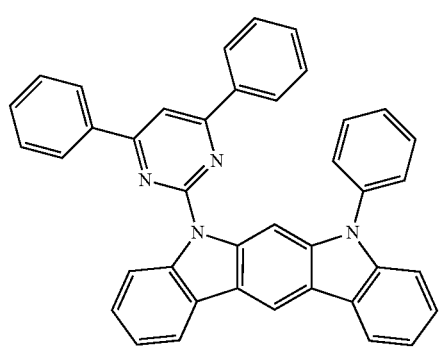
H-71
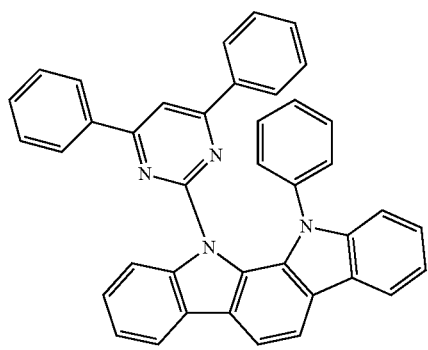
H-72
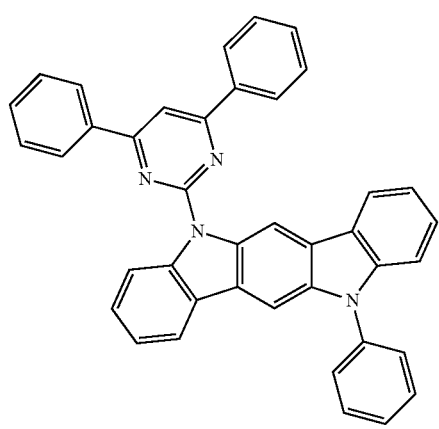
H-73
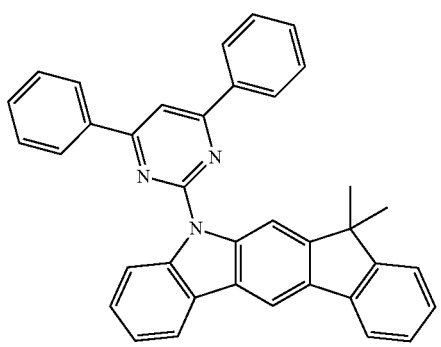
H-74
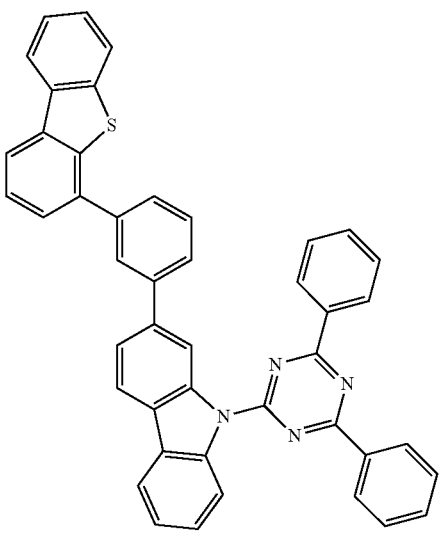
H-75
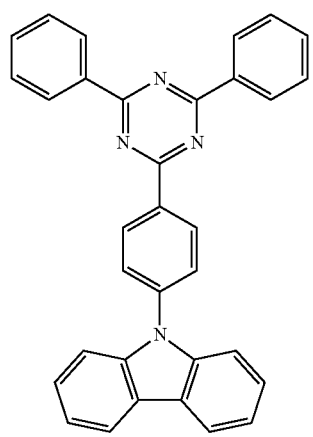

H-76
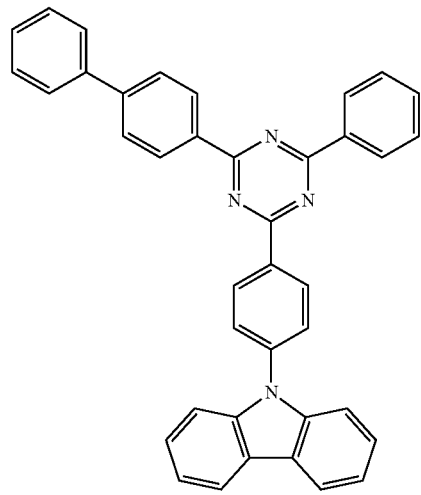
H-77
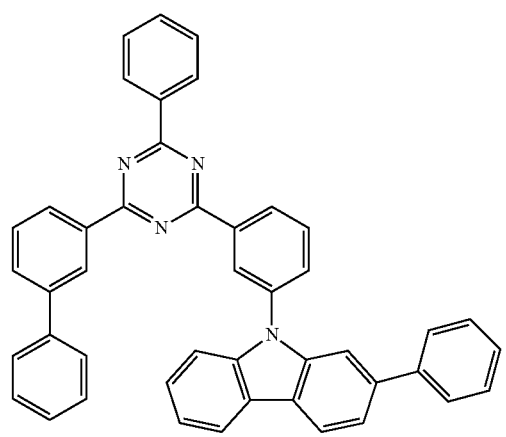
H-78
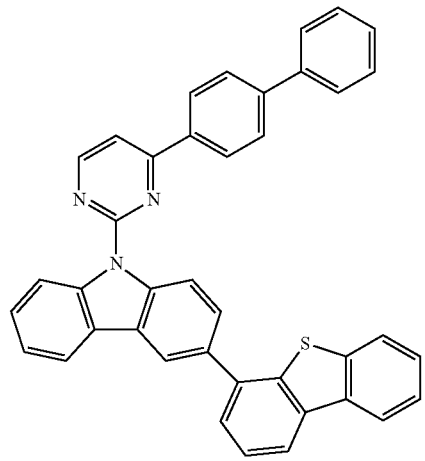
H-79
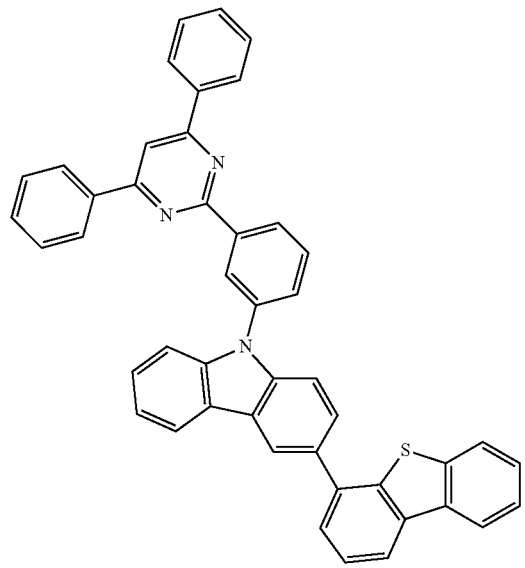
H-80
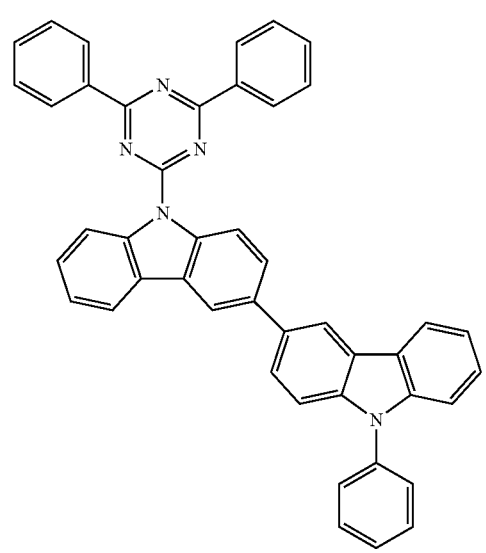
H-81
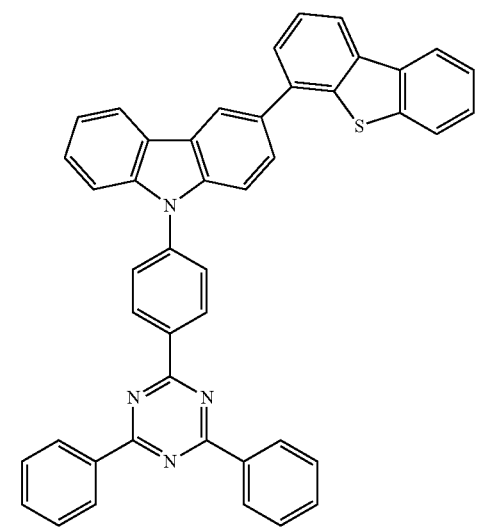

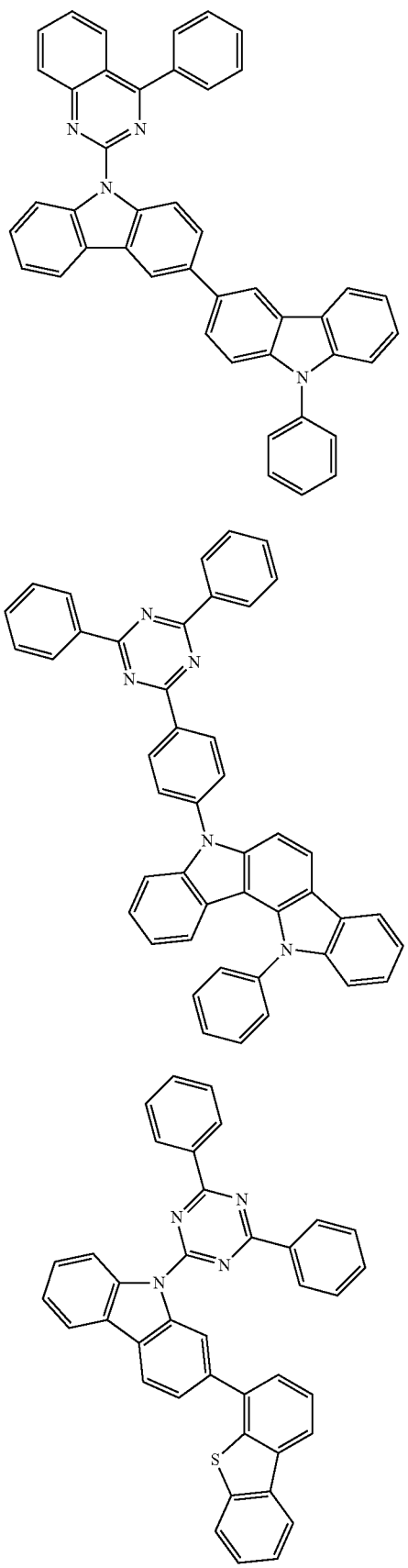
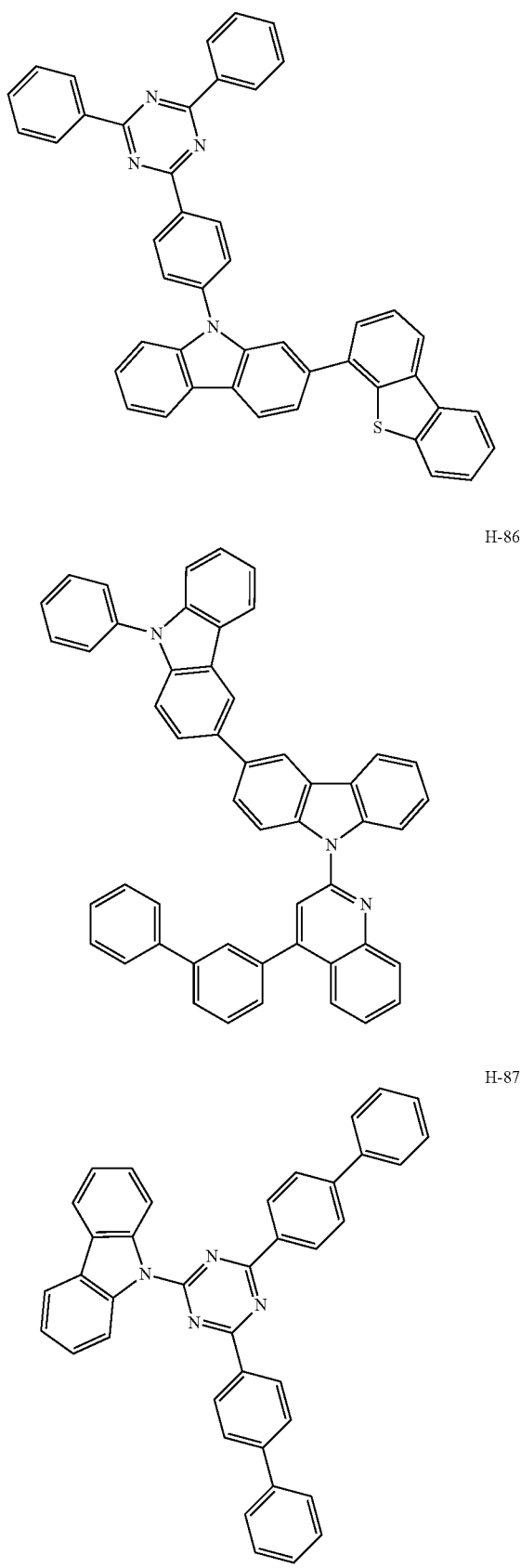

H-88
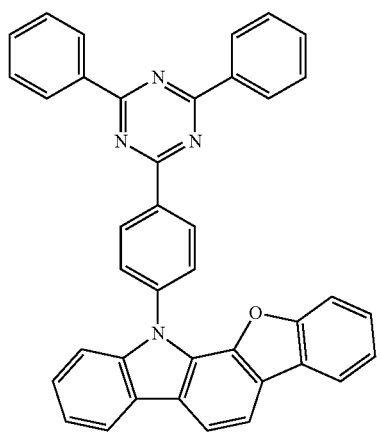
H-89
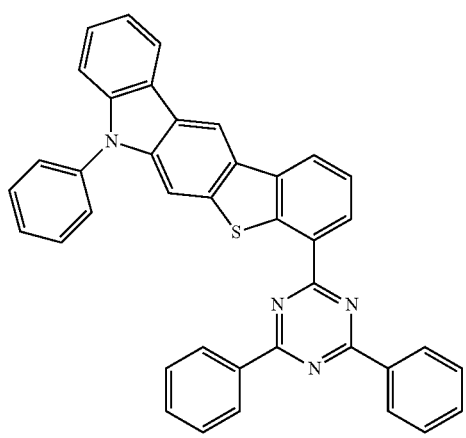
H-90
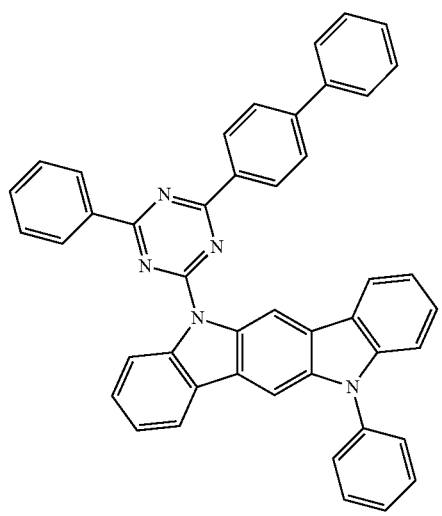
H-91
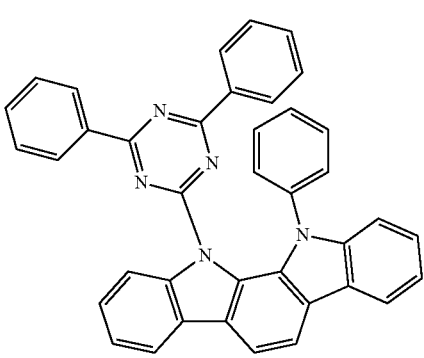
H-92
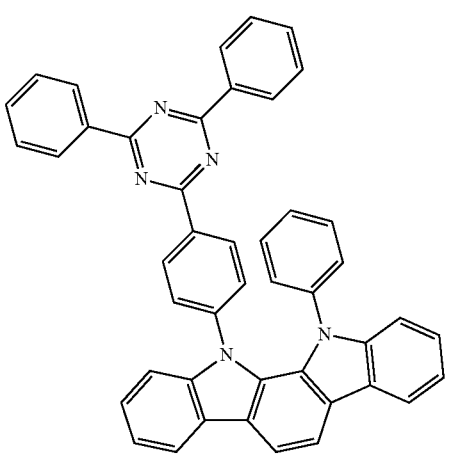
H-93
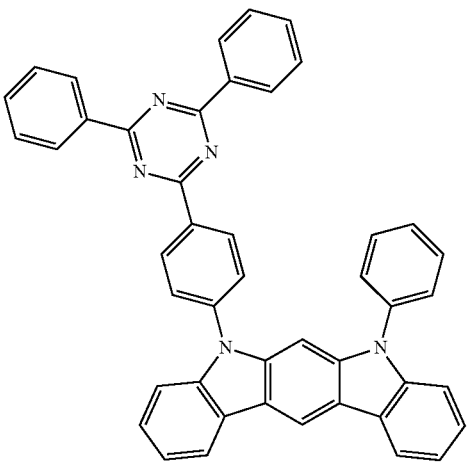

H-94
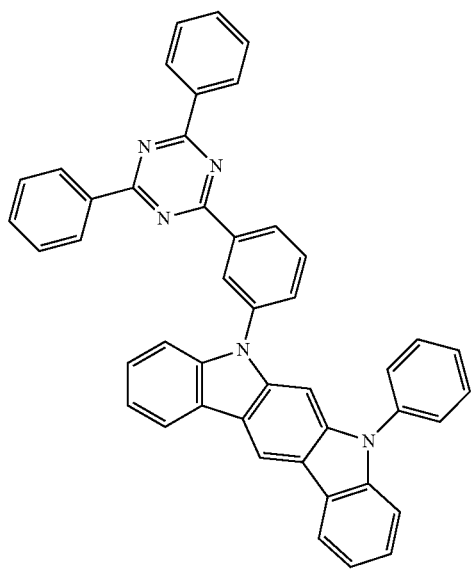
H-95
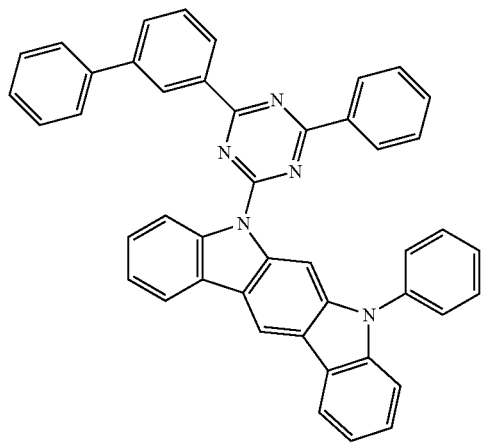
H-96
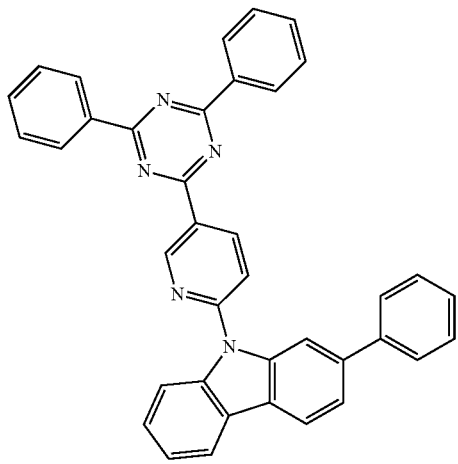
H-97
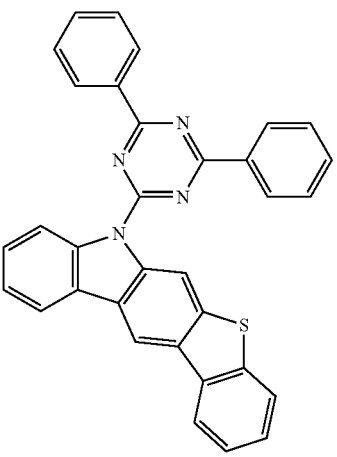
H-98
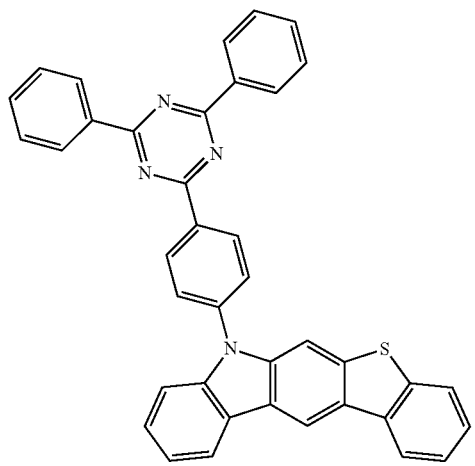
H-99
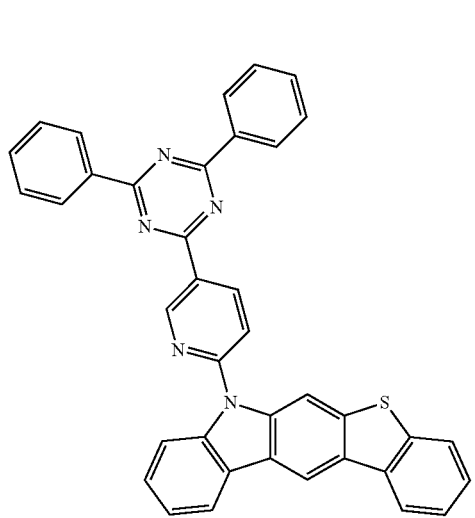

H-100
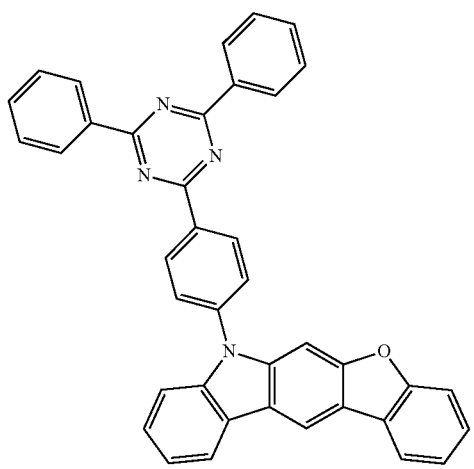
H-101
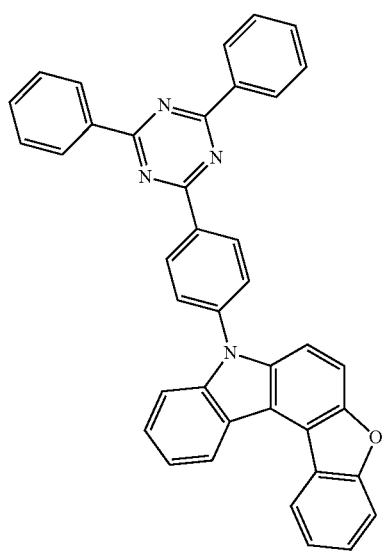
H-102
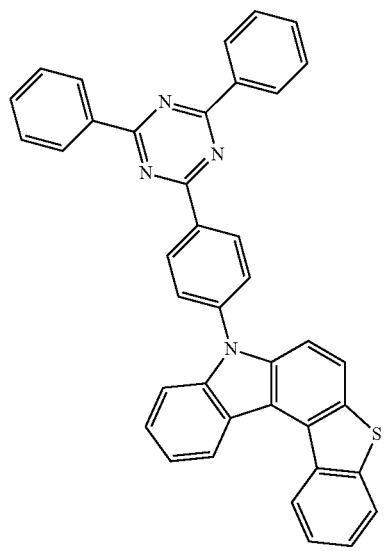
H-103
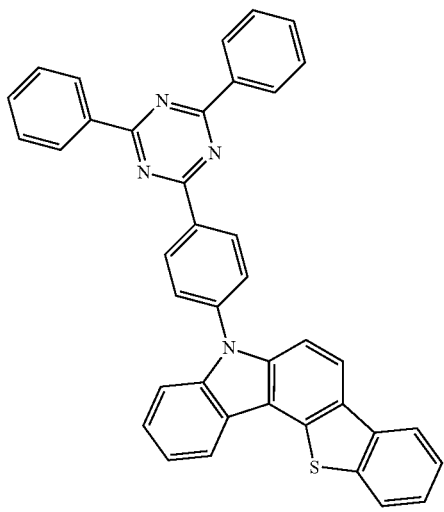
H-104
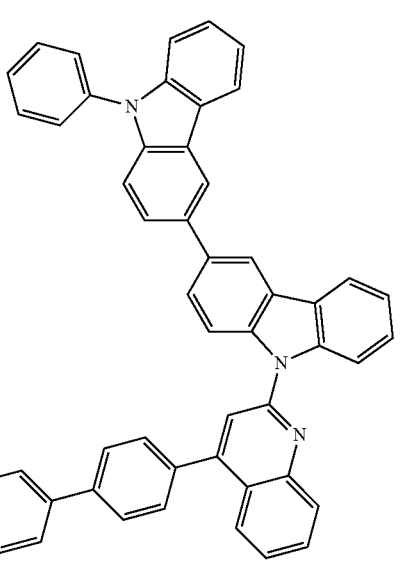
H-105
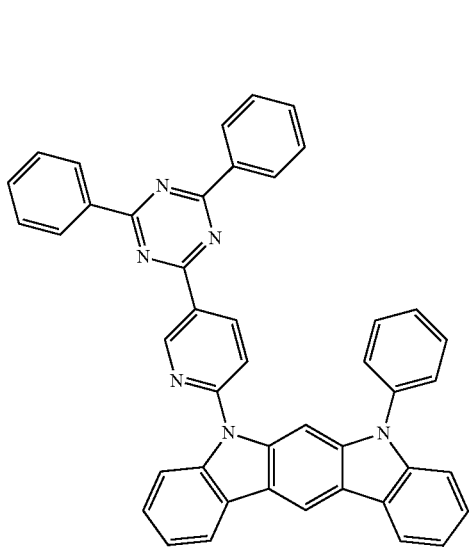

H-106
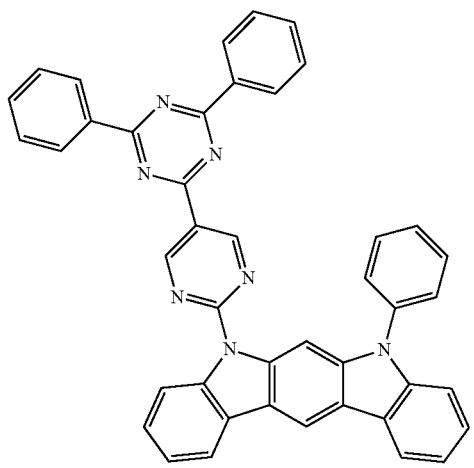
H-109
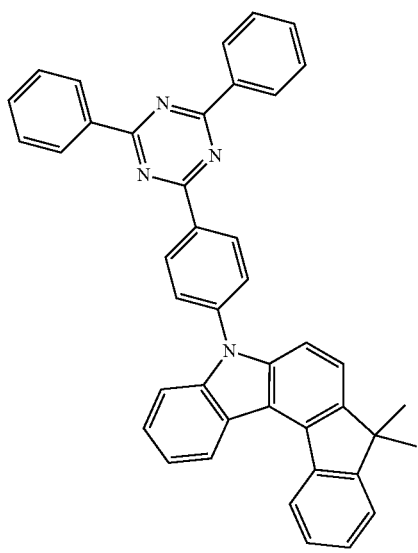
H-107
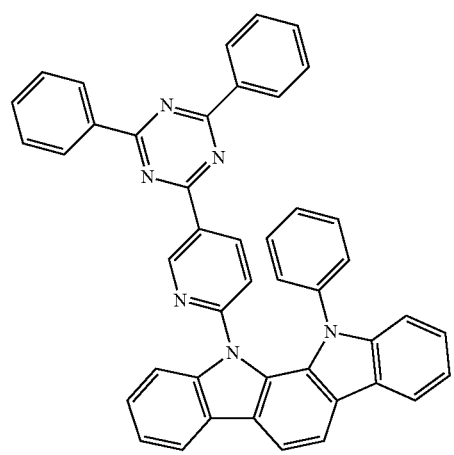
H-110
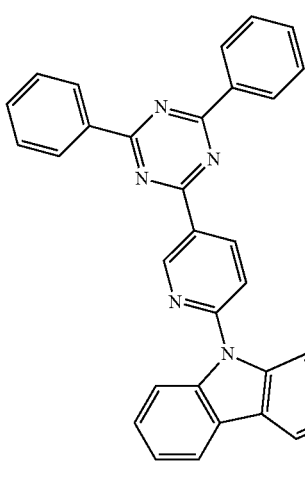
H-108
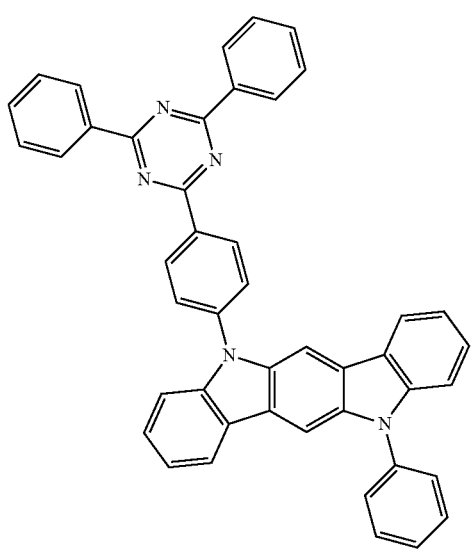
H-111
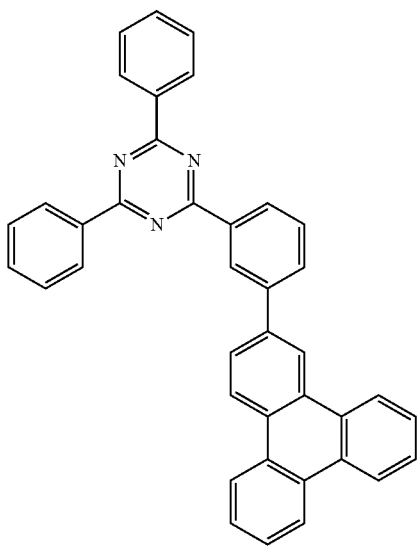

H-112
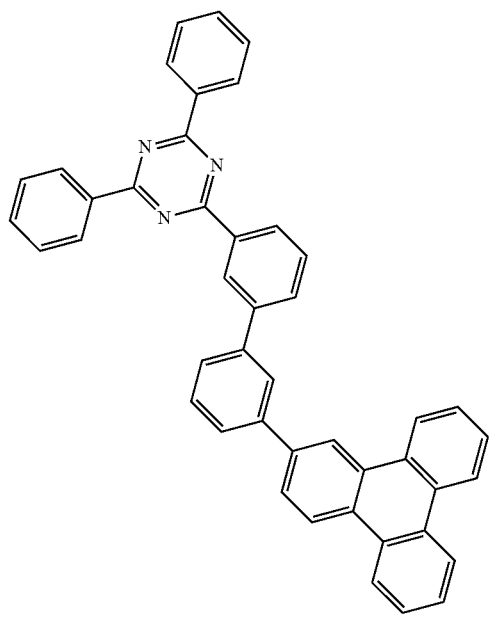
H-113
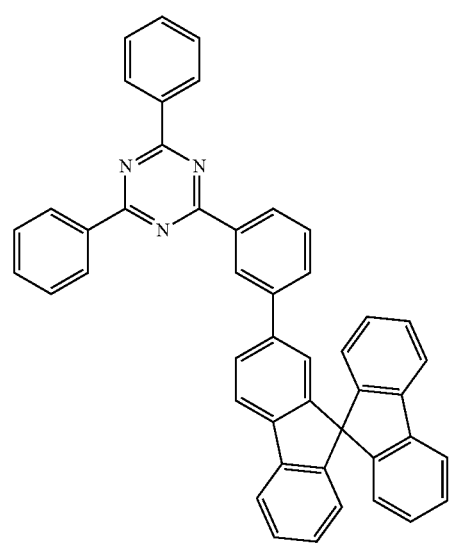
H-114
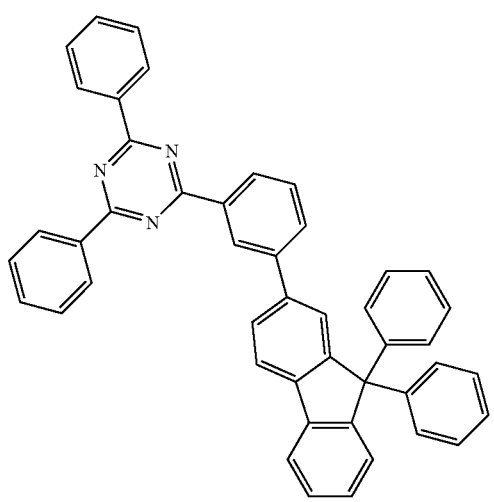
H-115
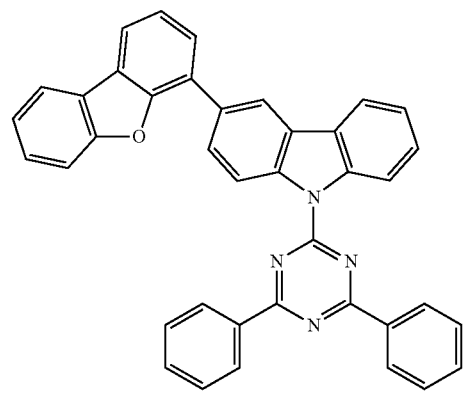
H-116
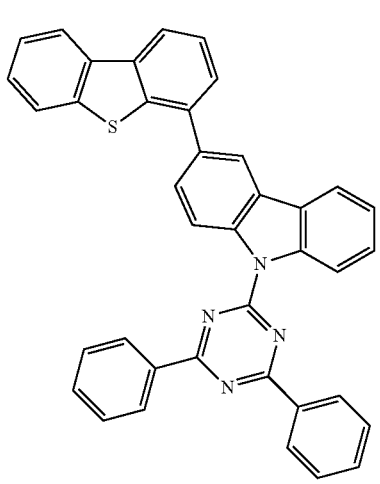
H-117
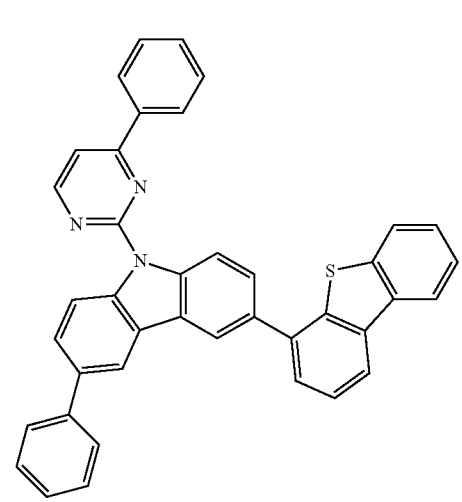

H-118
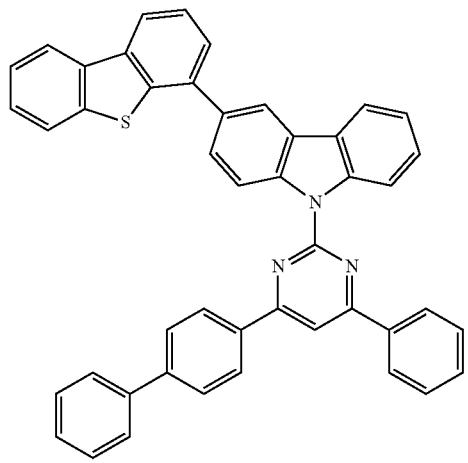
H-119
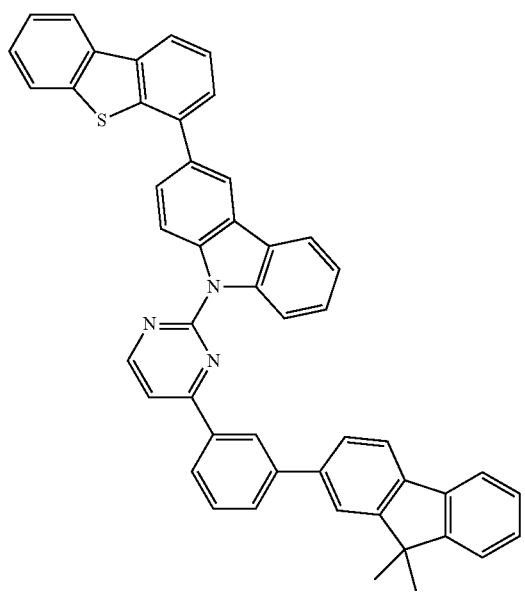
H-120
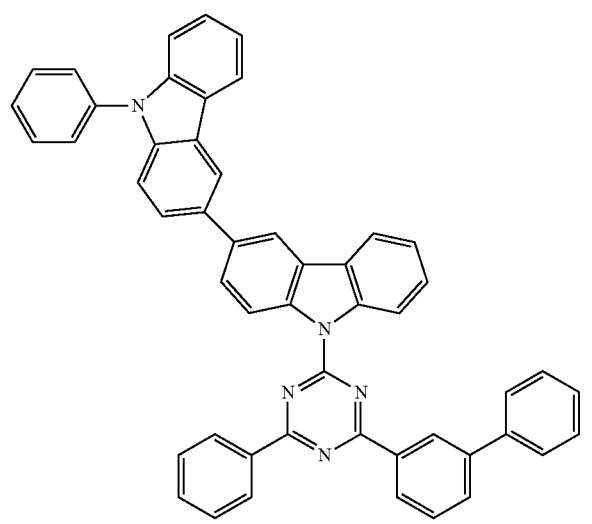
H-121
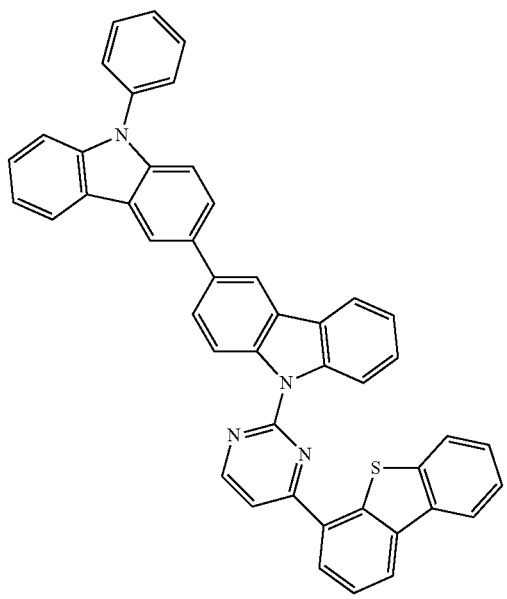
H-122
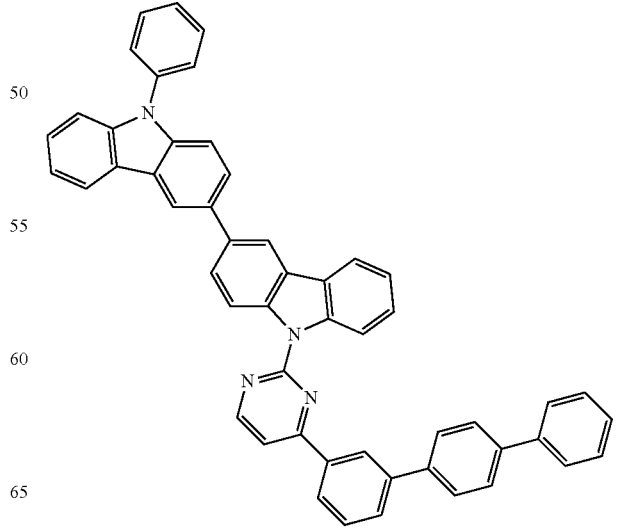

H-123
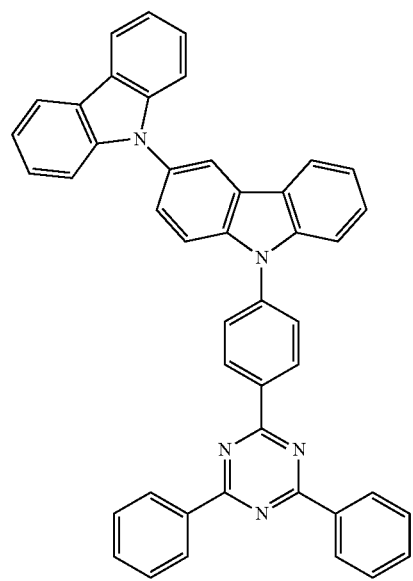
H-124
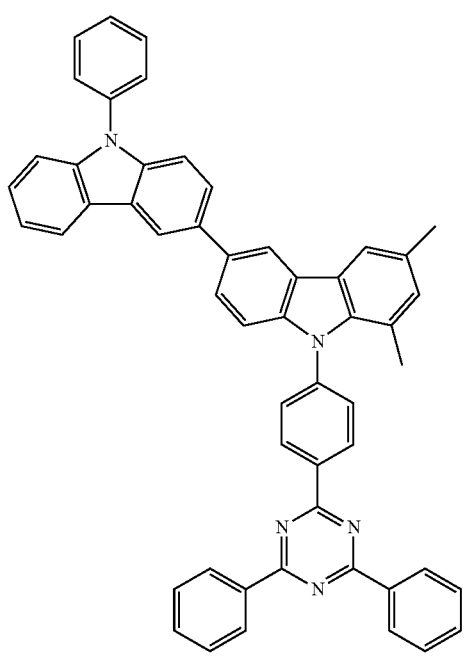
H-125
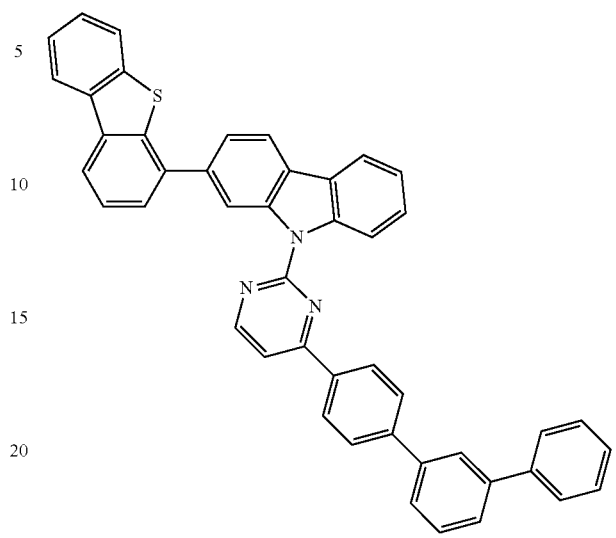
H-126
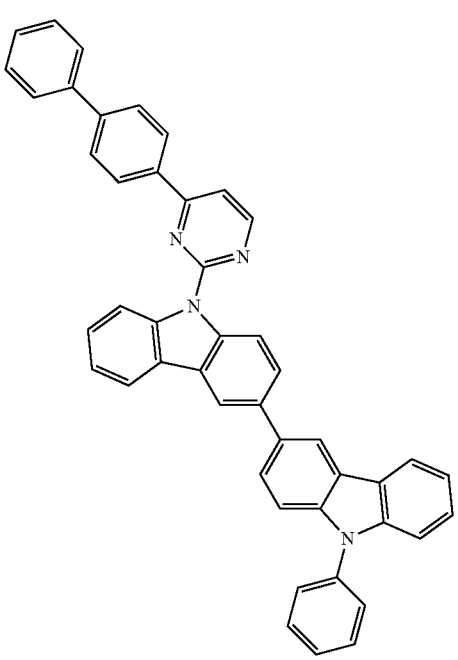

H-127
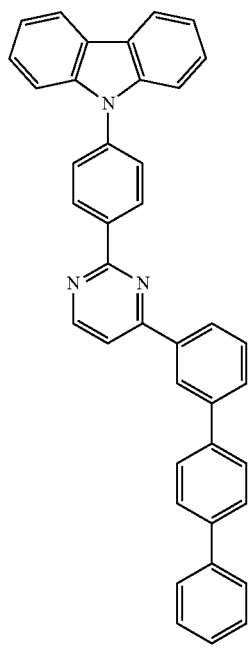
H-128
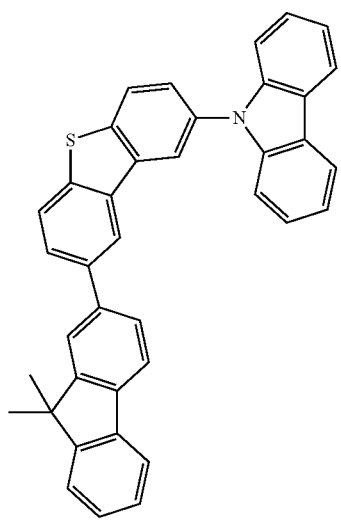
H-129
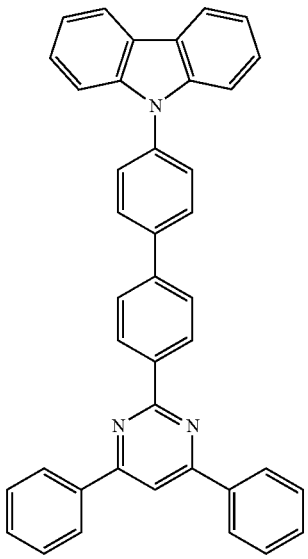
H-130

H-131
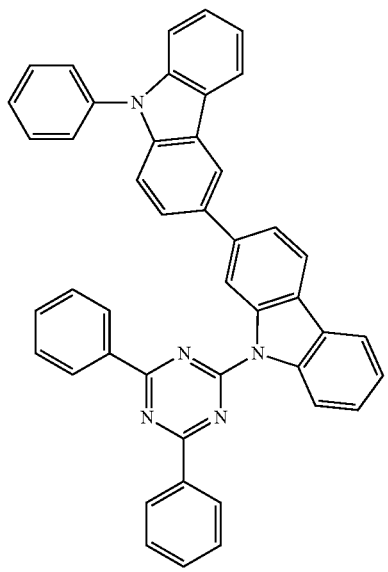
H-132
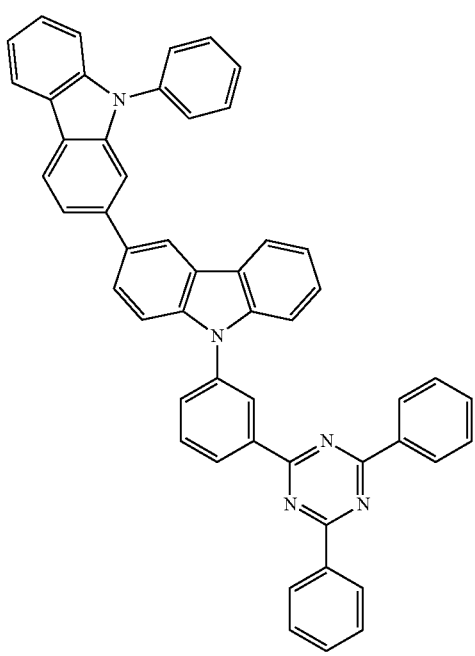
H-133
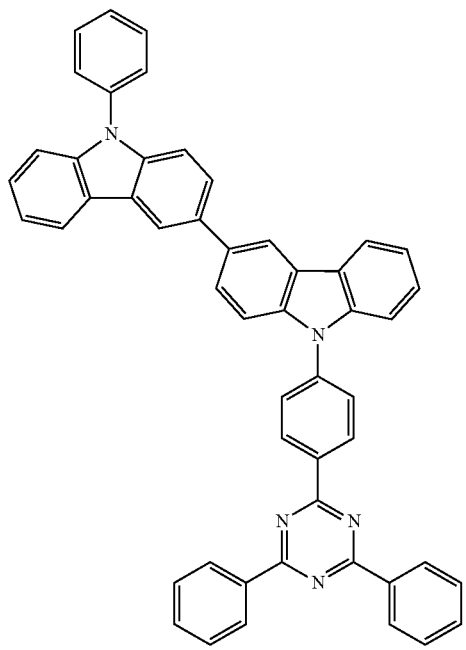
H-134
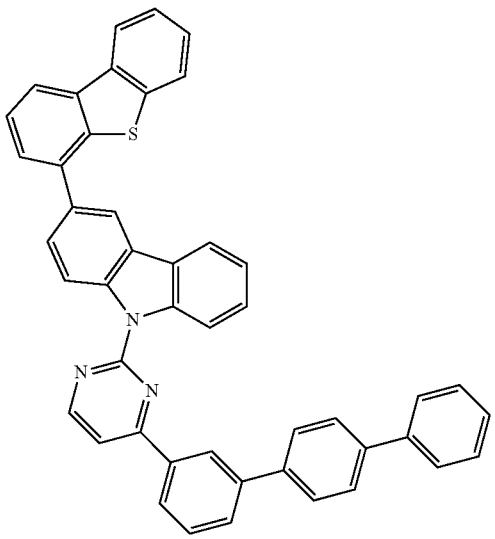

H-135
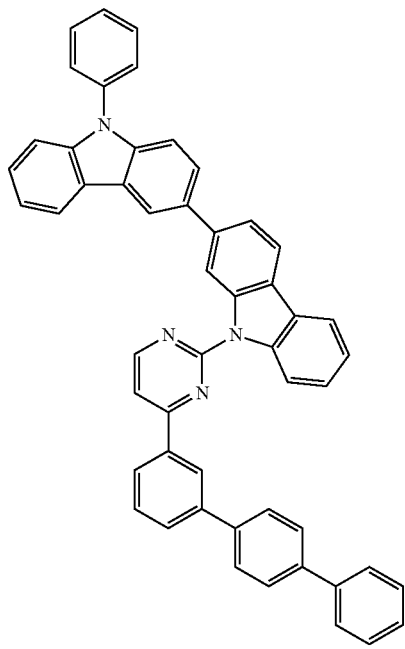
H-137
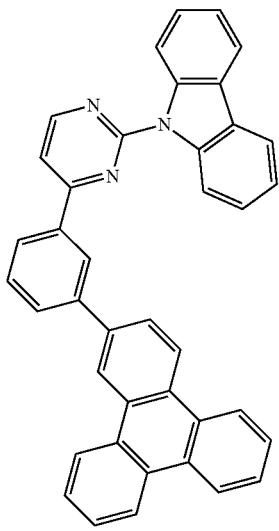
H-136
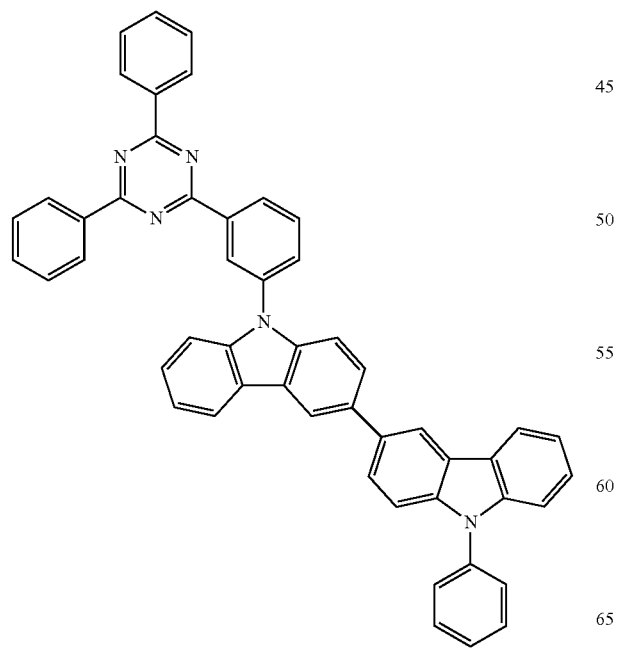
H-138
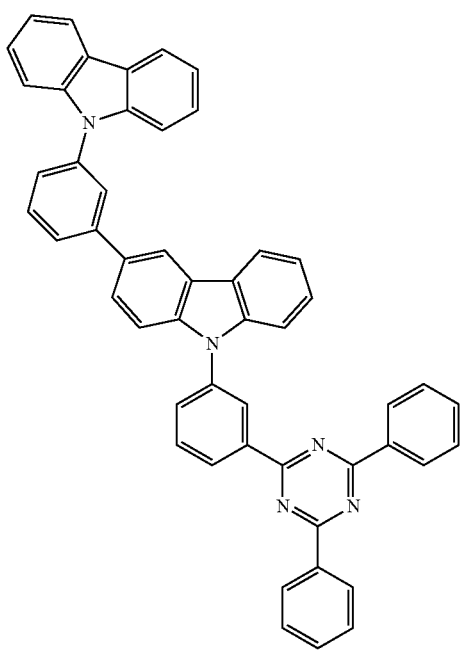

H-139
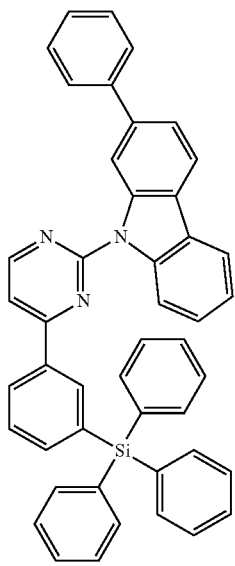
H-140
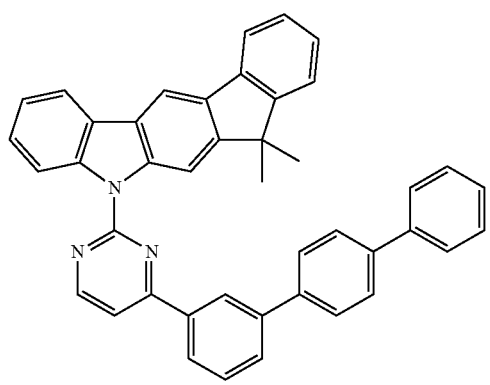
H-141
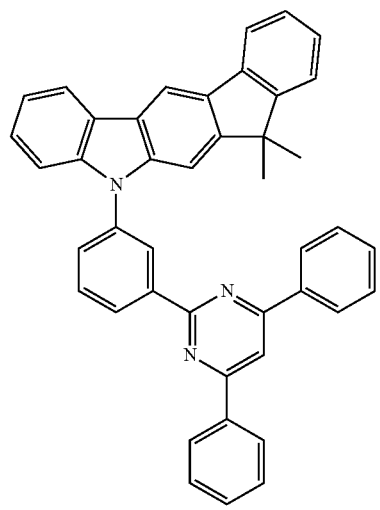
H-142
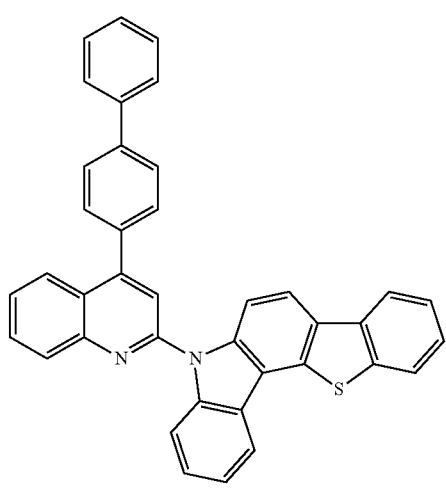
H-143
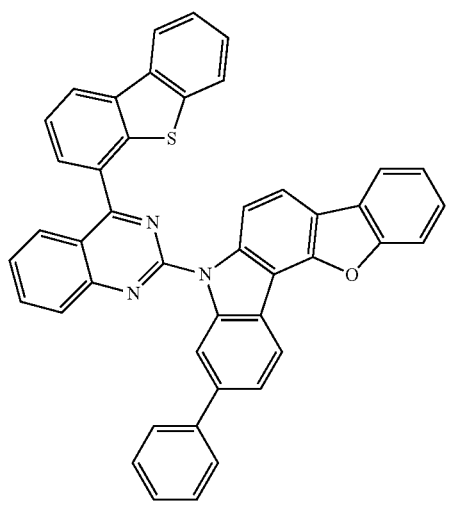
H-144
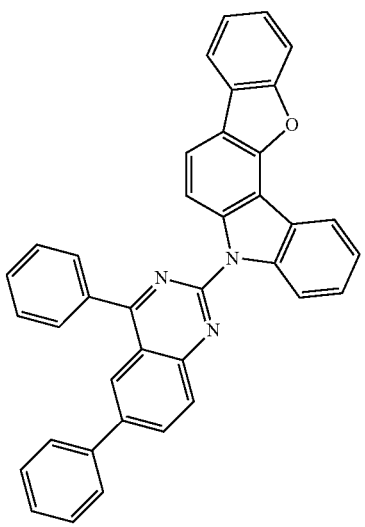

H-145
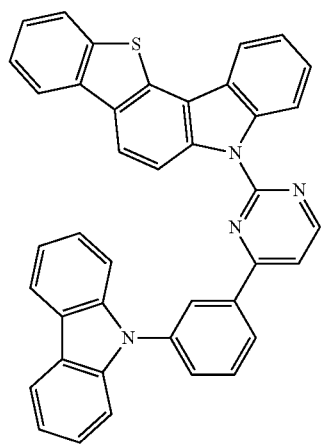
H-148
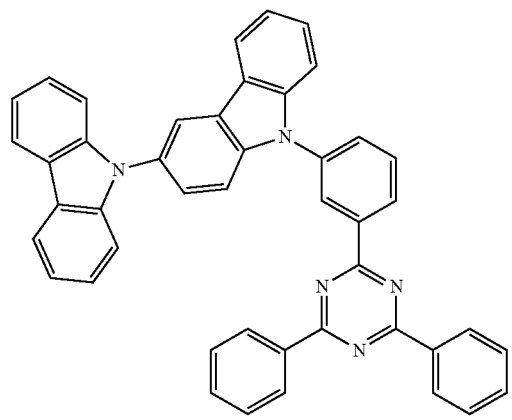
H-146
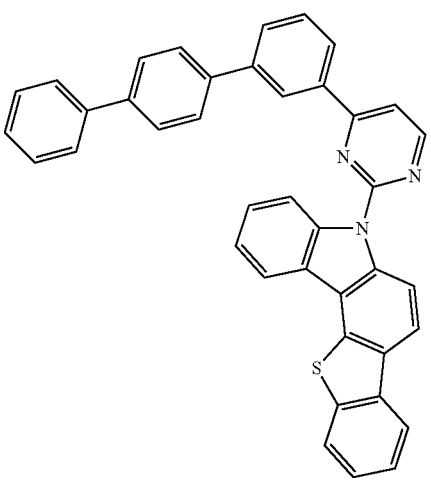
H-149
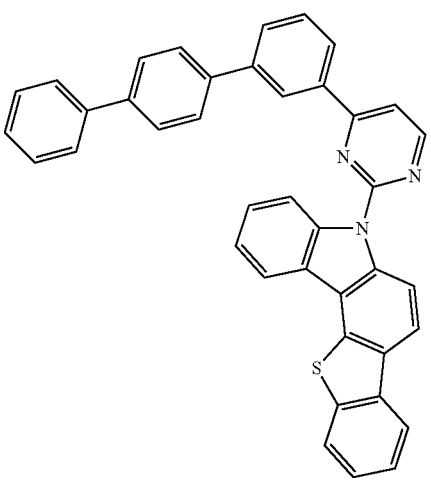
H-147
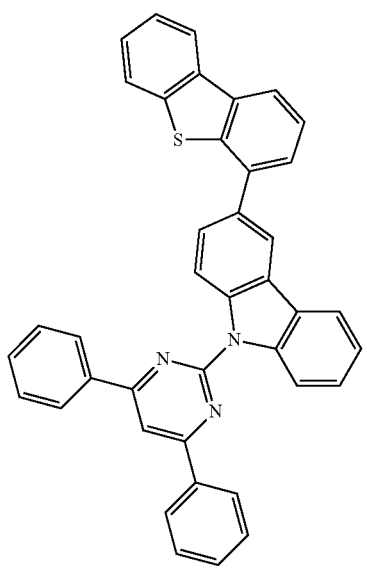
H-150
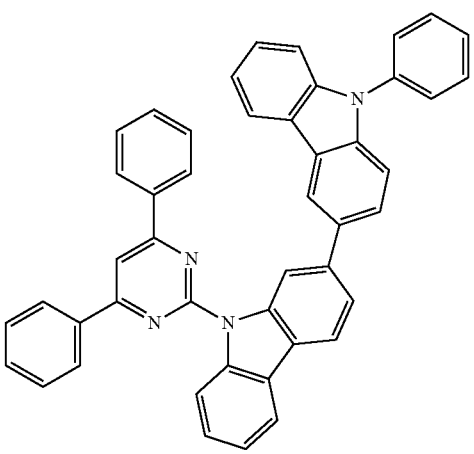

H-151
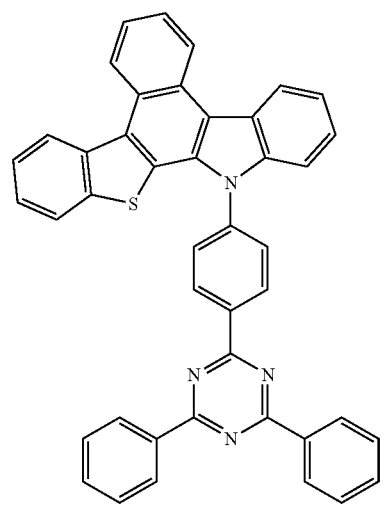
H-152
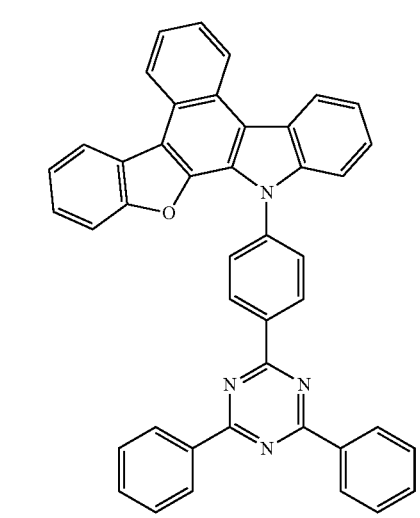
H-153
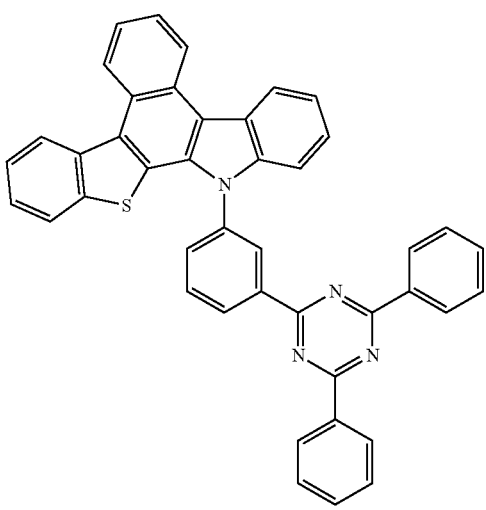
H-154
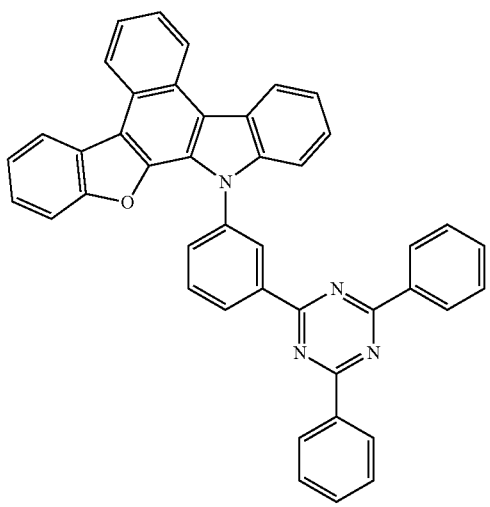
H-155
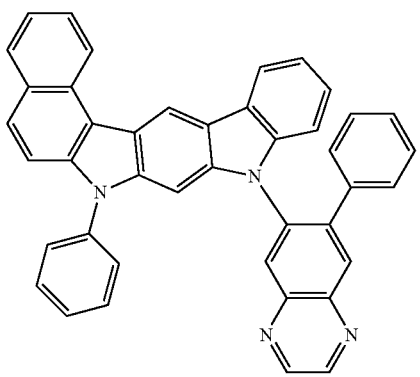
H-156
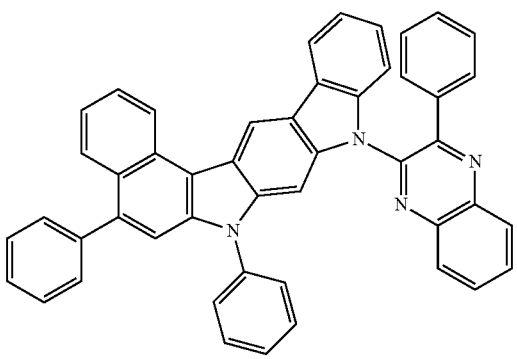
H-157
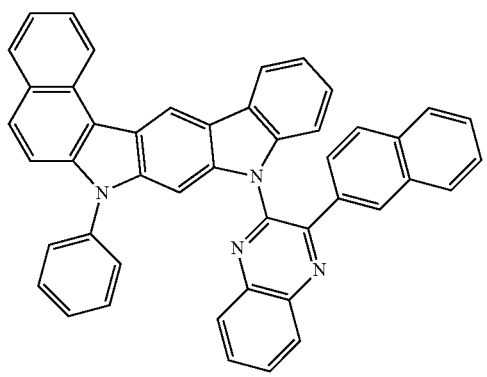

H-158
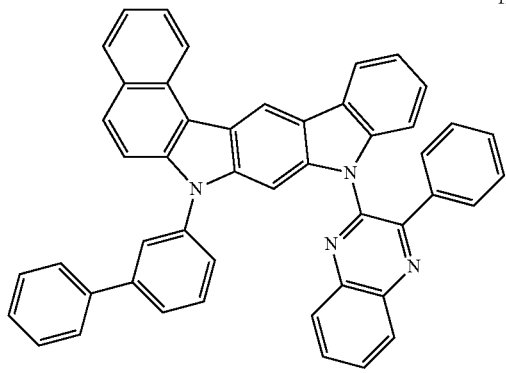
H-159
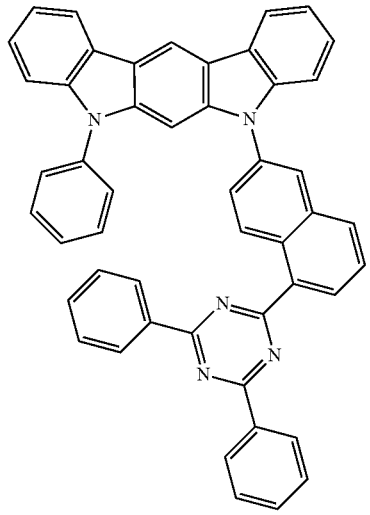
H-160
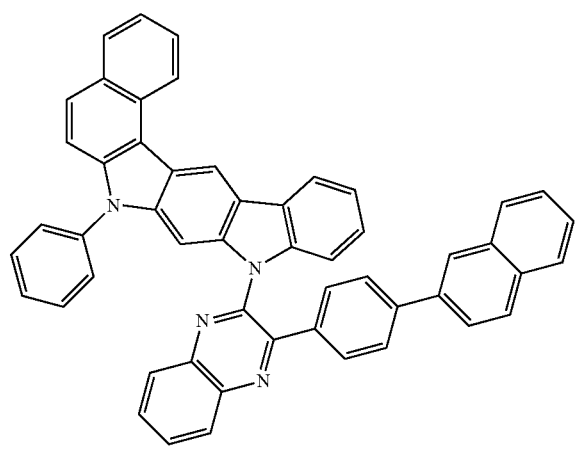
H-161
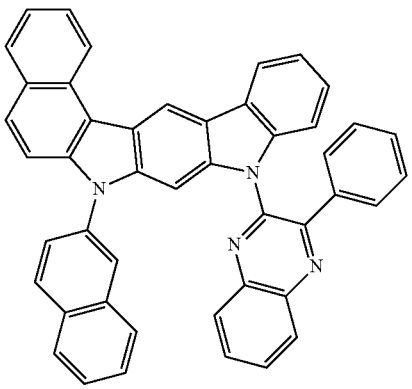
H-162
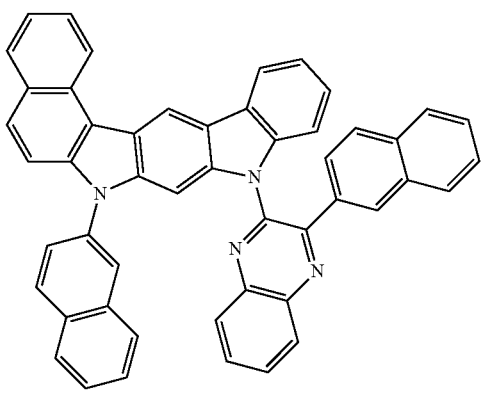
H-163
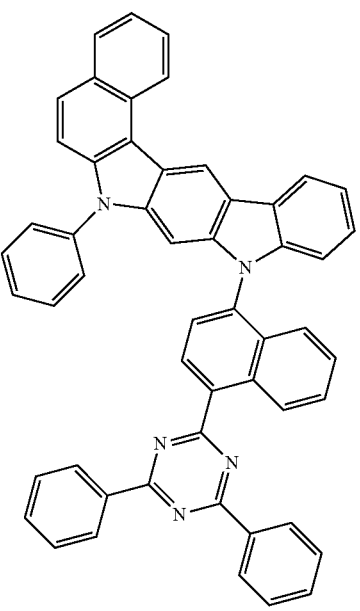

H-164
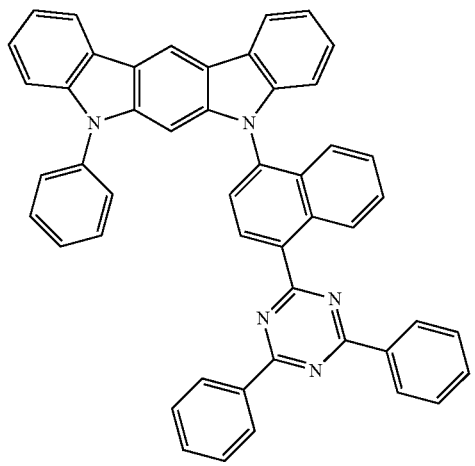
H-165
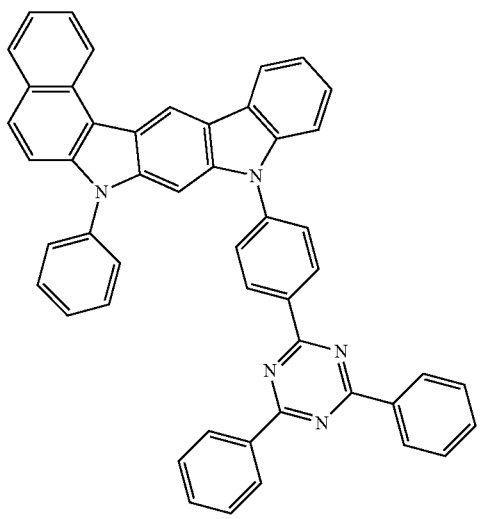
H-166
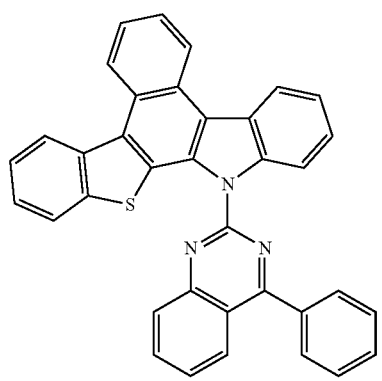
H-167
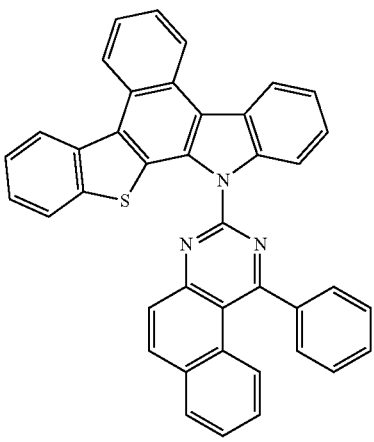
H-168
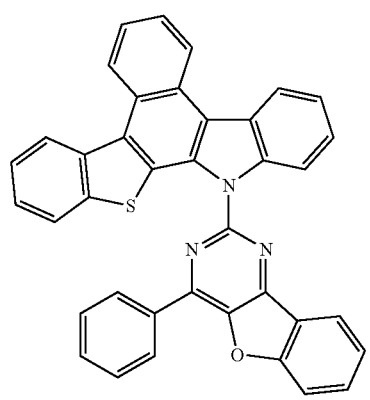
H-169
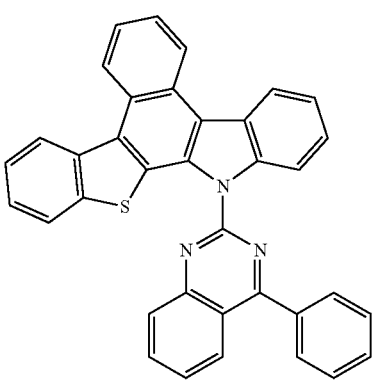
H-170
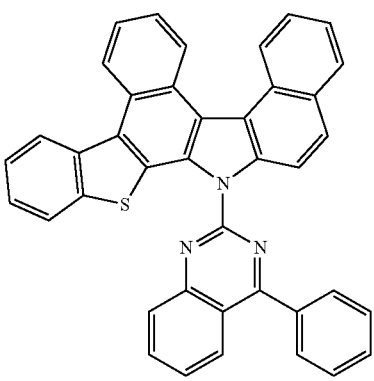

H-171 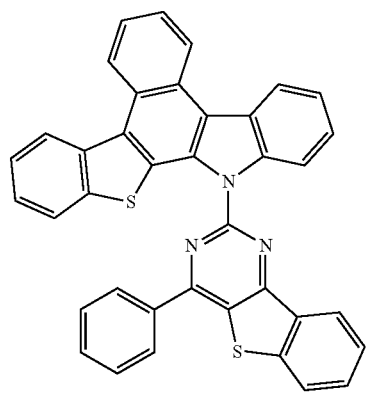
H-172 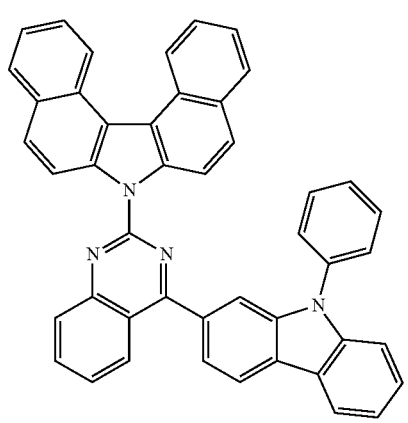
H-173 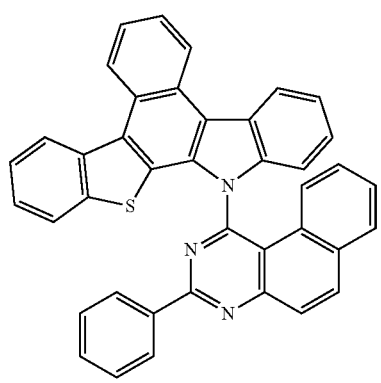
H-174 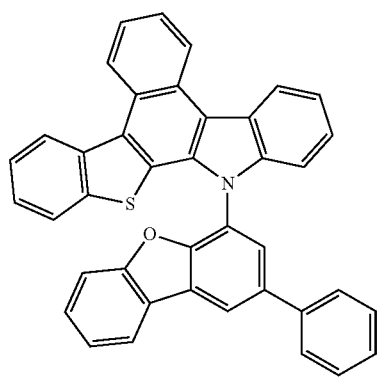
H-175 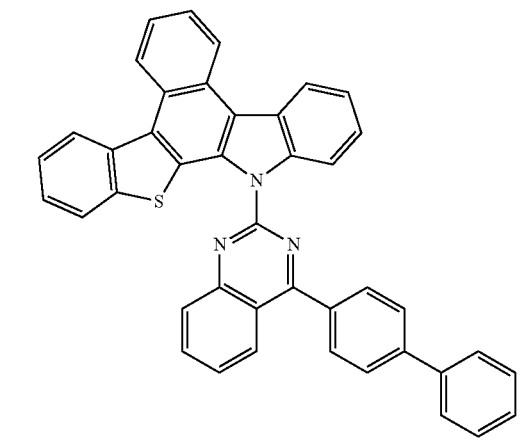
H-176 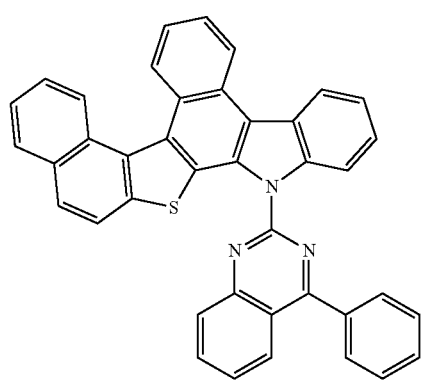
H-177 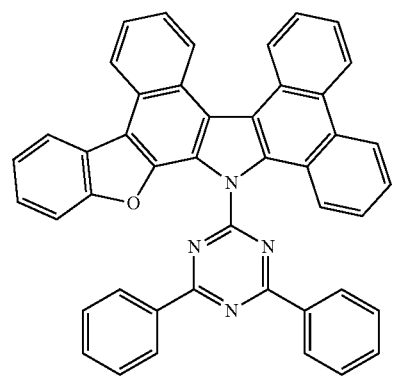
H-178 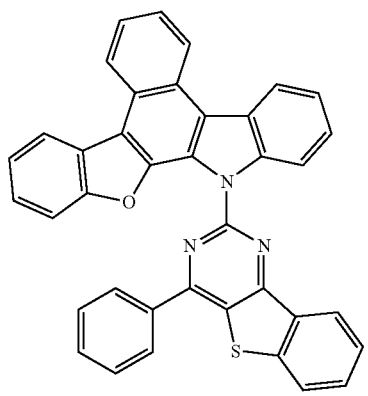

H-179
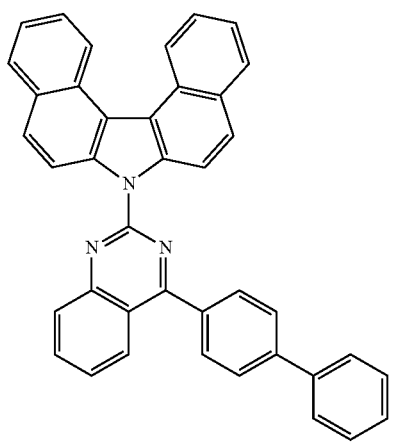
H-182
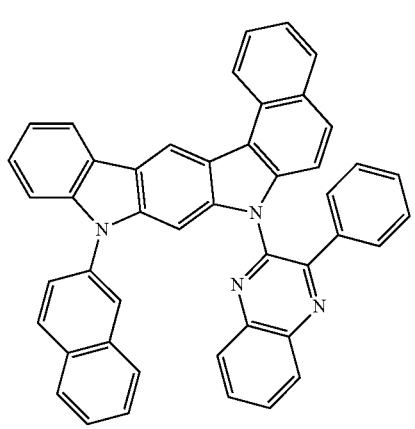
H-180
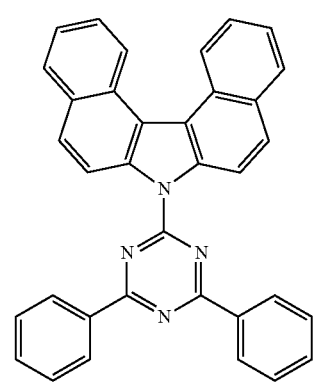
H-183
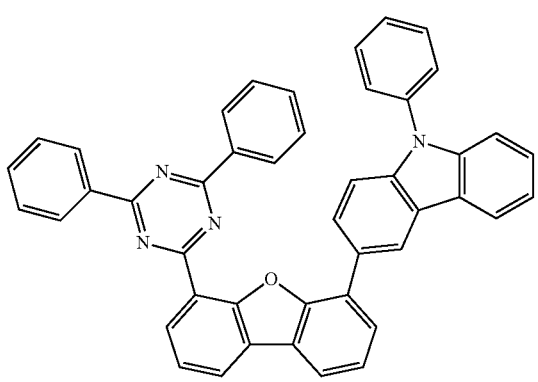
H-181
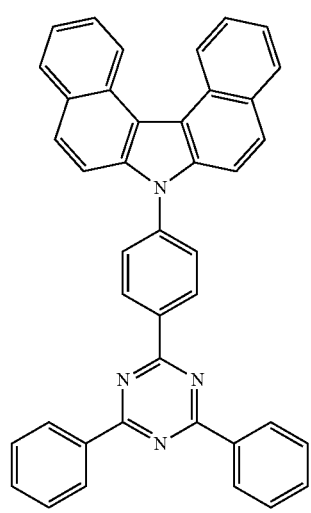
H-184
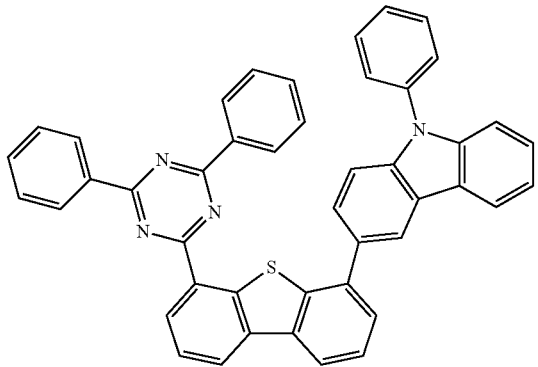

H-185
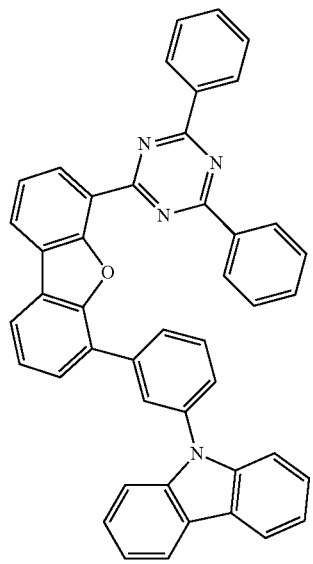
H-186
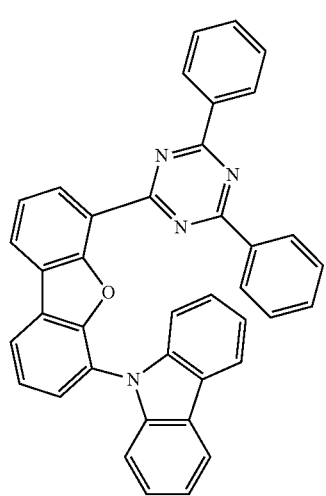
H-187
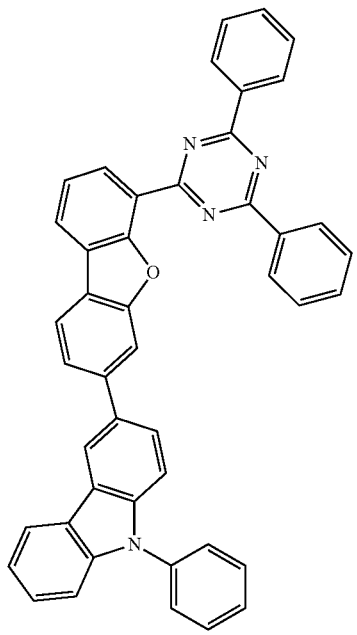
H-188
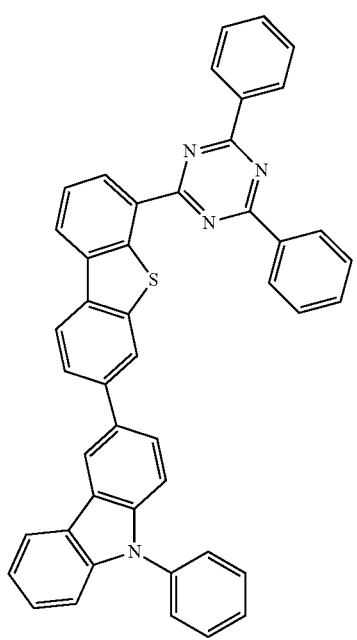

H-189
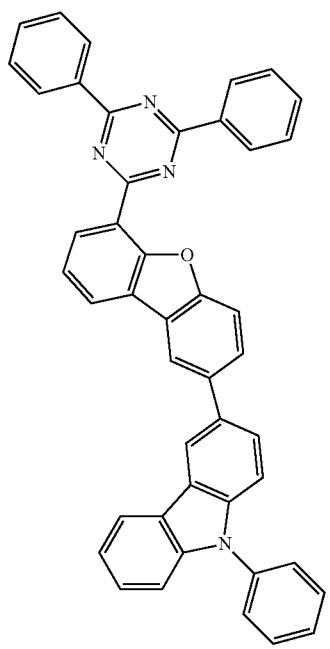
H-190
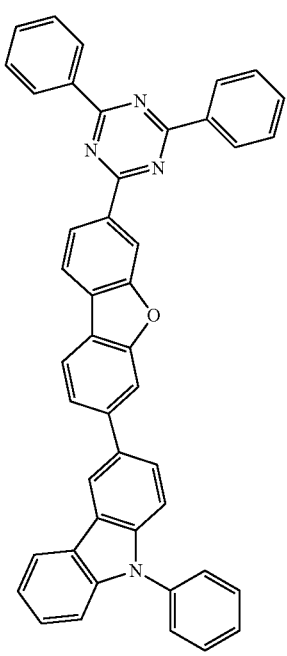
H-191
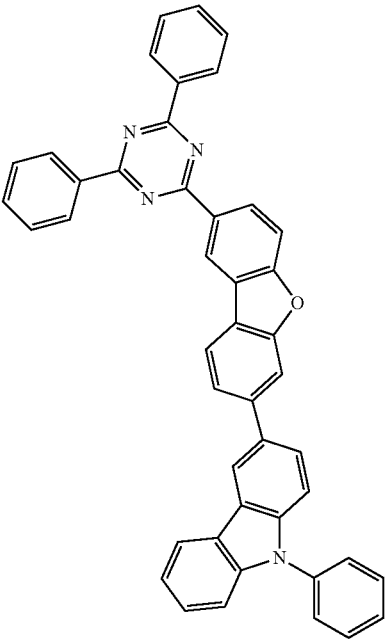
H-192
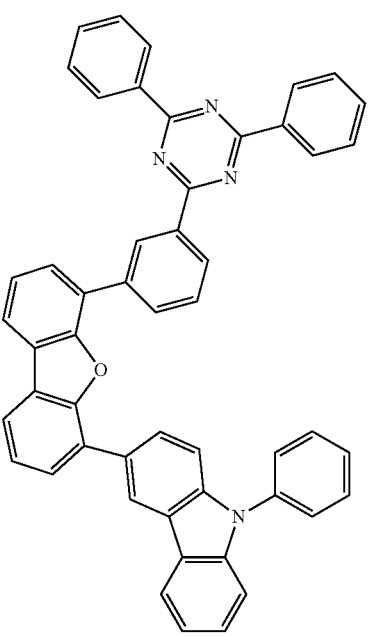

H-193
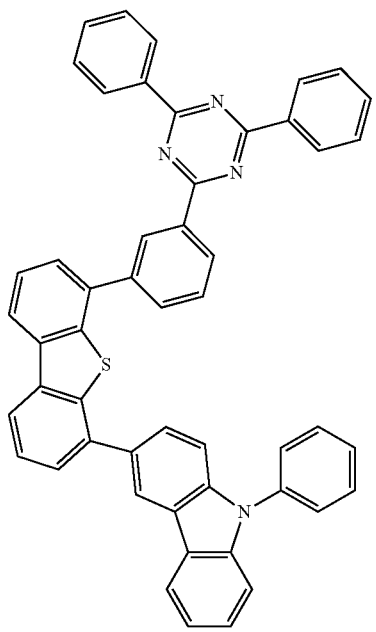
H-194
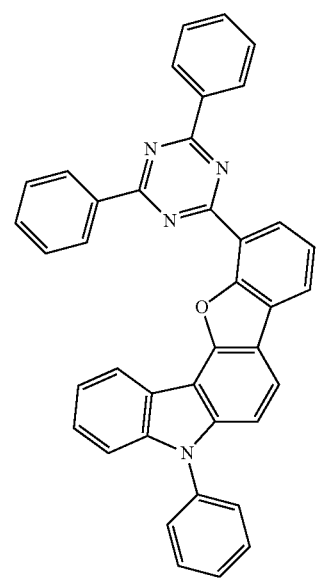
H-195
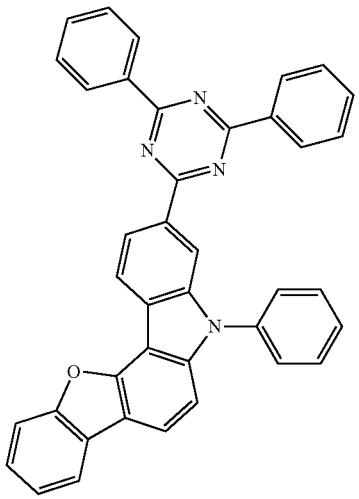
H-196
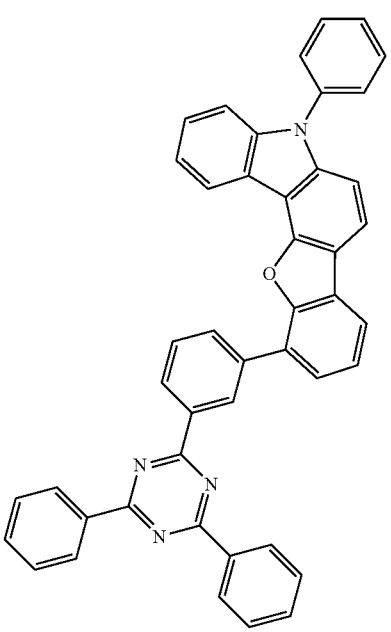

H-197
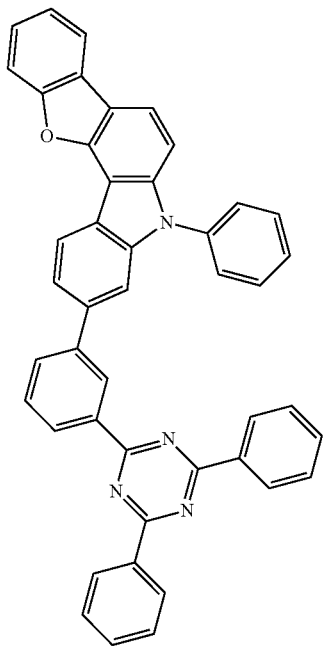
H-198
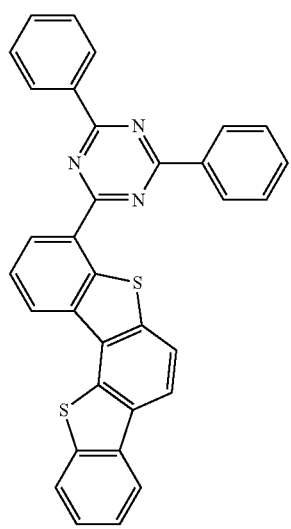
H-199
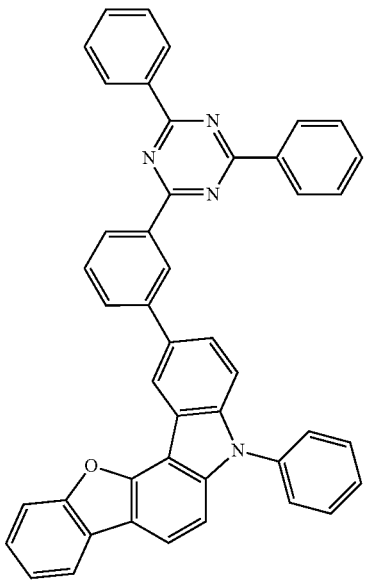
H-200
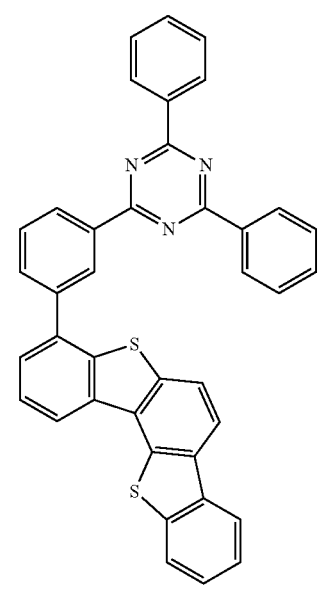
H-201

H-202
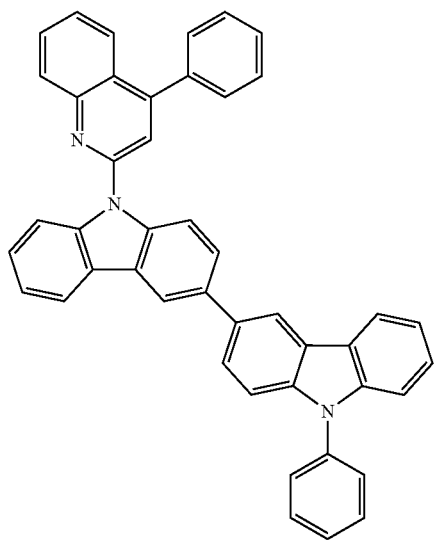
H-205
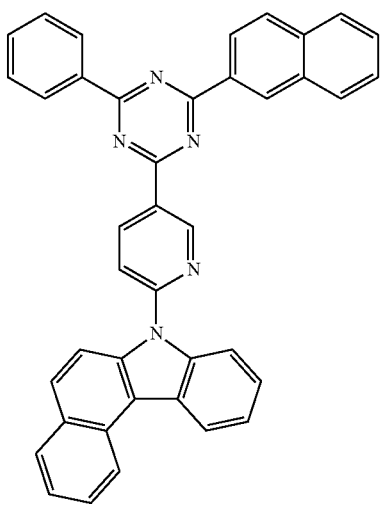
H-203
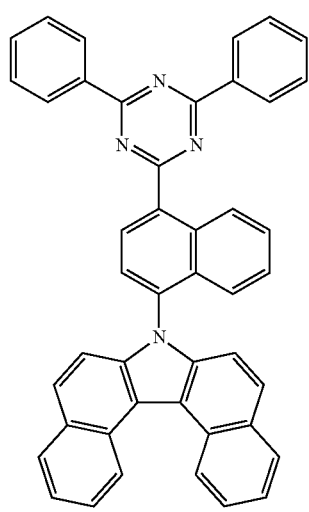
H-206
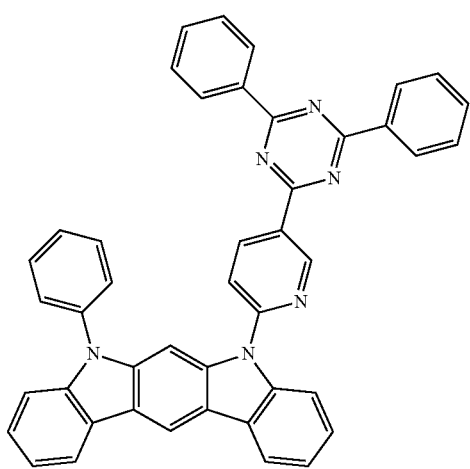
H-204
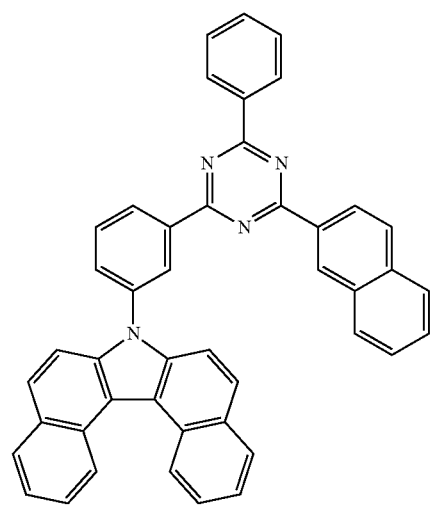
H-207
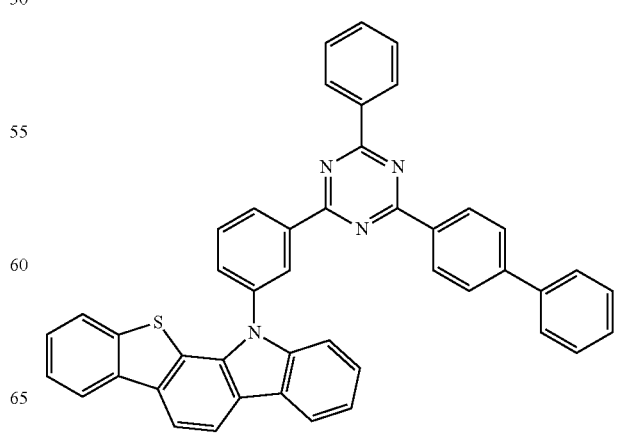

H-208

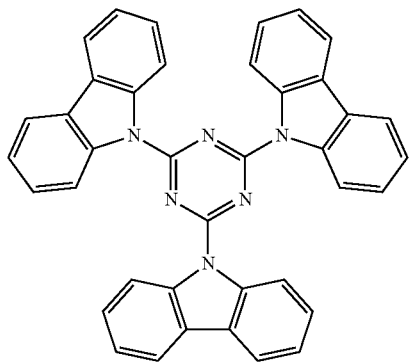

H-209

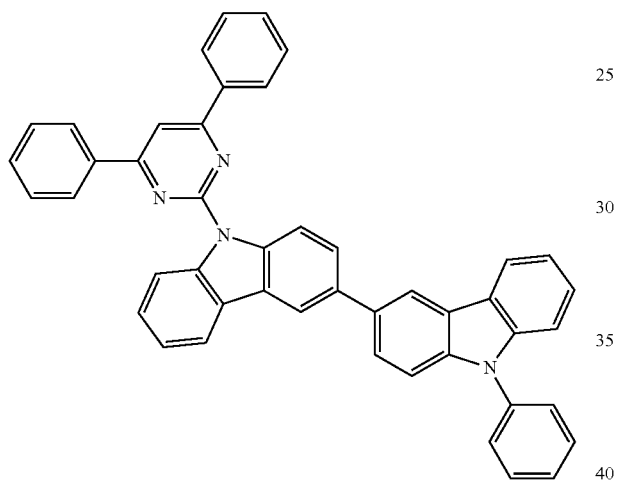

H-210

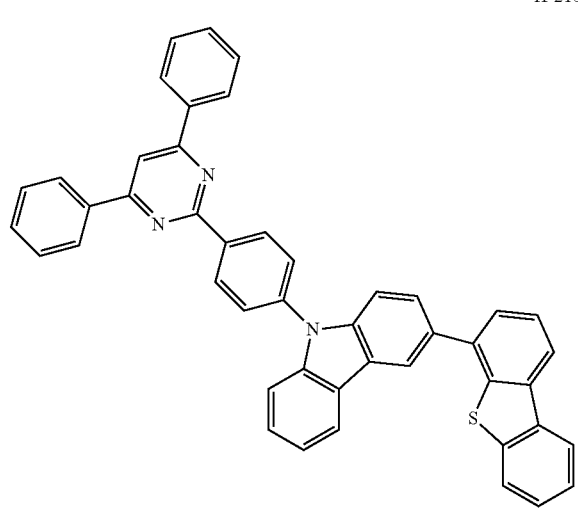

H-211

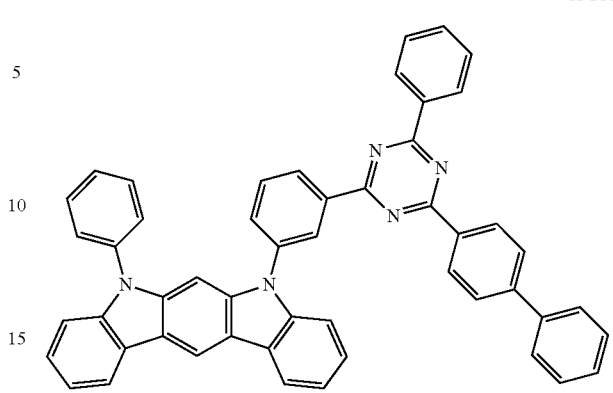

wherein TPS represents a triphenylsilyl group.

A dopant compound which can be used in combination with the compound of the present disclosure includes the compound represented by the following formula 101, but is not limited thereto:

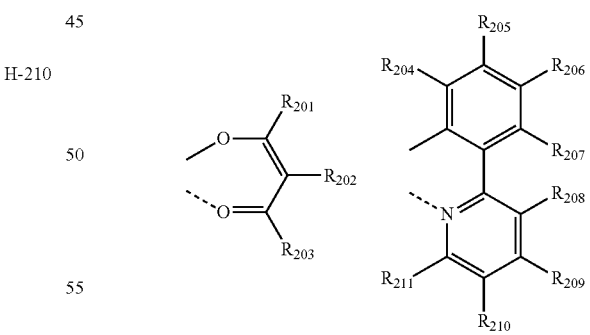

(101)

wherein
L is selected from the following structures:

$R_{100}$ to $R_{103}$ each independently represent hydrogen, deuterium, a halogen, a (C1-C30)alkyl unsubstituted or substituted with a halogen(s), a substituted or unsubstituted (C3-C30)cycloalkyl, a substituted or unsubstituted (C6-C30)aryl, a cyano, a substituted or unsubstituted 3- to 30-membered heteroaryl, or a substituted or unsubstituted (C1-C30) alkoxy; or $R_{100}$ to $R_{103}$ may be linked to adjacent $R_{100}$ to $R_{103}$ to form a substituted or unsubstituted fused ring with pyridine, e.g., a substituted or unsubstituted quinoline, a substituted or unsubstituted isoquinoline, a substituted or unsubstituted benzofuropyridine, a substituted or unsubstituted benzothienopyridine, a substituted or unsubstituted indenopyridine, a substituted or unsubstituted benzofuroquinoline, a substituted or unsubstituted benzothienoquinoline, or a substituted or unsubstituted indenoquinoline;

$R_{104}$ to $R_{107}$ each independently represent hydrogen, deuterium, a halogen, a (C1-C30)alkyl unsubstituted or substituted with a halogen(s), a substituted or unsubstituted (C3-C30)cycloalkyl, a substituted or unsubstituted (C6-C30)aryl, a substituted or unsubstituted 3- to 30-membered heteroaryl, a cyano, or a substituted or unsubstituted (C1-C30)alkoxy; or $R_{104}$ to $R_{107}$ may be linked to adjacent $R_{104}$ to $R_{107}$ to form a substituted or unsubstituted fused ring with benzene, e.g., a substituted or unsubstituted naphthalene, a substituted or unsubstituted fluorene, a substituted or unsubstituted dibenzothiopene, a substituted or unsubstituted dibenzofurane, a substituted or unsubstituted indenopyridine, a substituted or unsubstituted benzofuropyridine, or a substituted or unsubstituted benzothienopyridine;

$R_{201}$ to $R_{211}$ each independently represent hydrogen, deuterium, a halogen, a (C1-C30)alkyl unsubstituted or substituted with a halogen(s), a substituted or unsubstituted (C3-C30)cycloalkyl, or a substituted or unsubstituted (C6-C30)aryl; or $R_{201}$ to $R_{211}$ may be linked to adjacent $R_{201}$ to $R_{211}$ to form a substituted or unsubstituted fused ring; and n represents an integer of 1 to 3.

Specifically, the dopant compound includes the following compounds, but is not limited thereto:

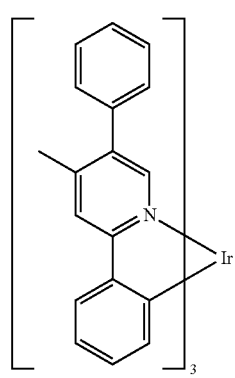

D-1

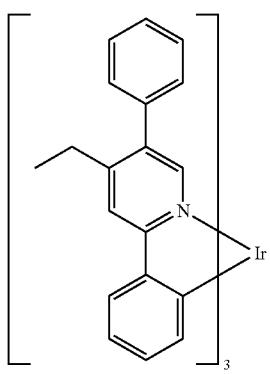

D-2

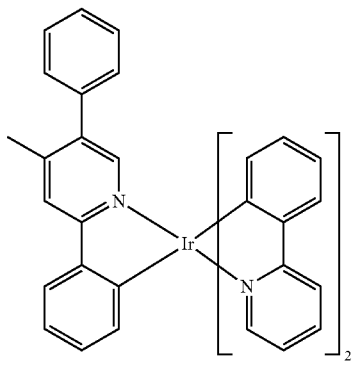

D-3

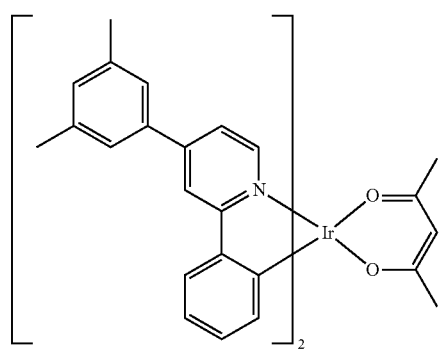

D-4

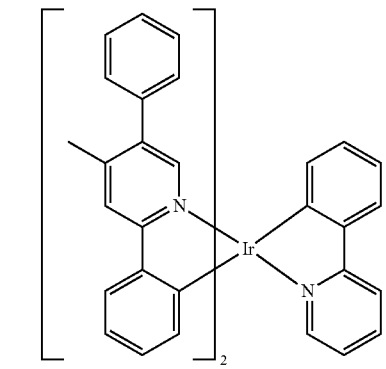

D-5

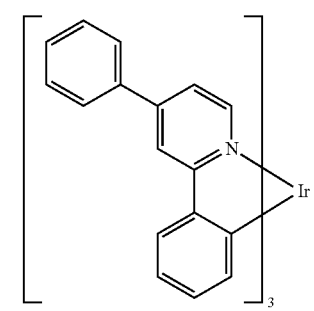

D-6

-continued
D-7
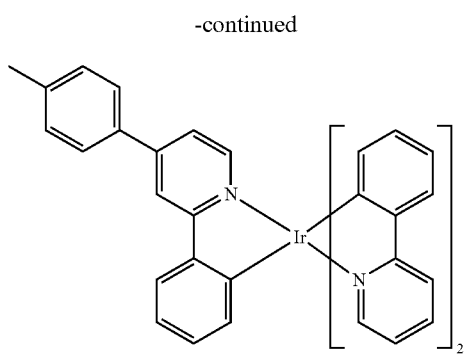
D-8
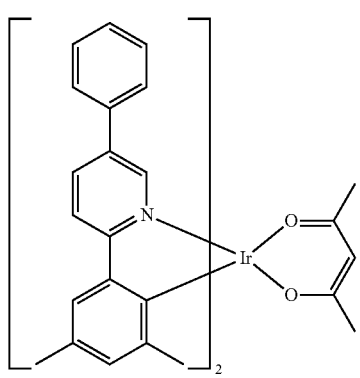
D-9
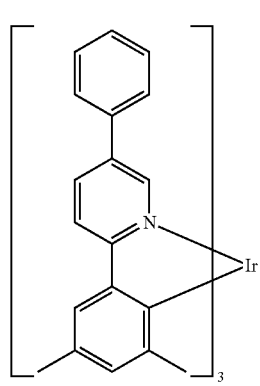
D-10
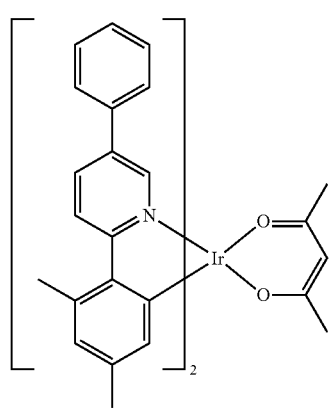
-continued
D-11
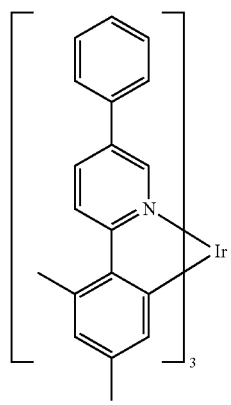
D-12
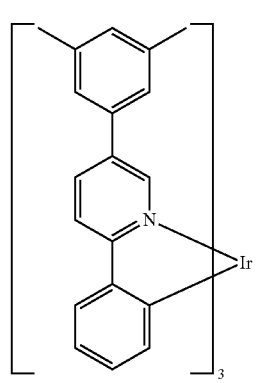
D-13
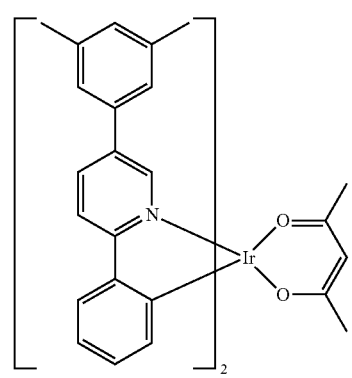
D-14
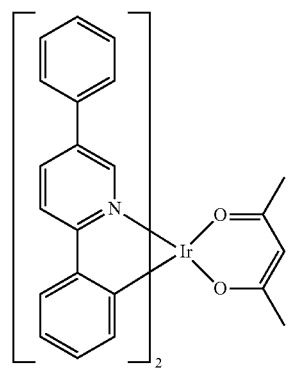

D-15 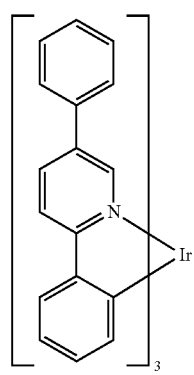
D-19 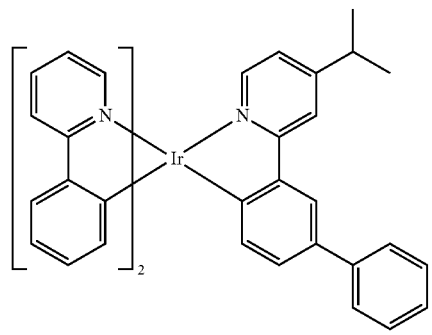
D-16 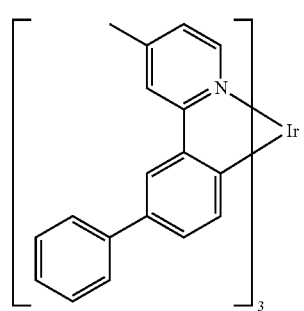
D-20 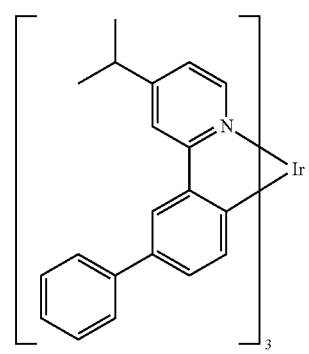
D-17 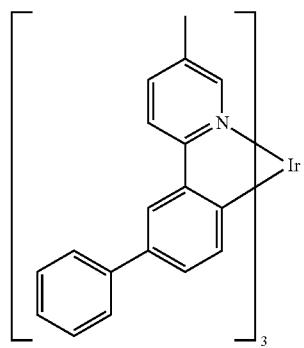
D-21 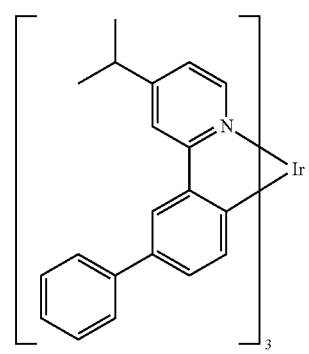
D-18
D-22 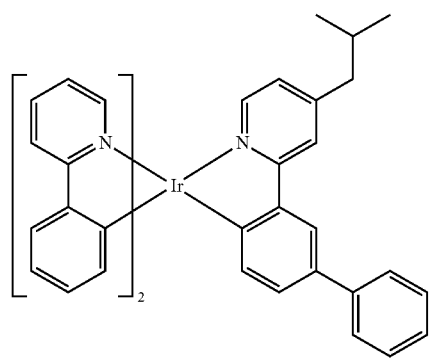

-continued
D-23
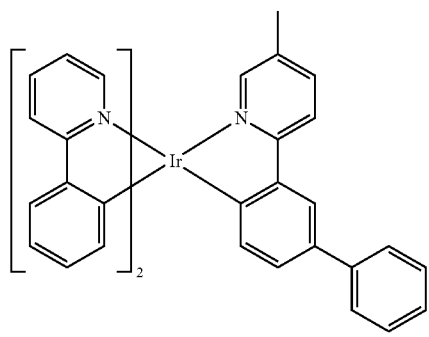
D-24
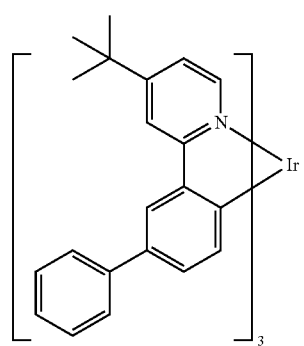
D-25
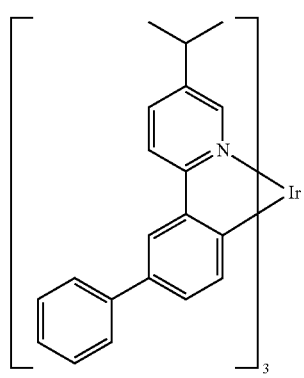
D-26
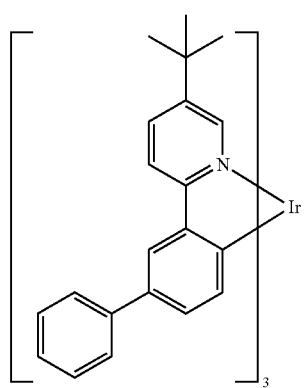
-continued
D-27
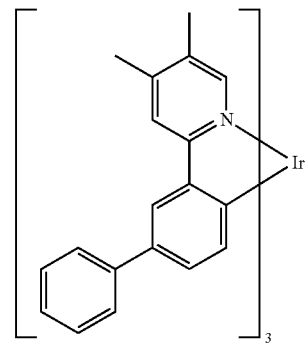
D-28
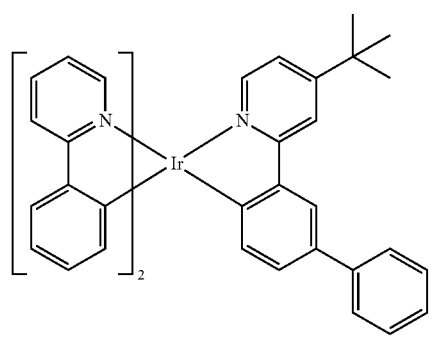
D-29
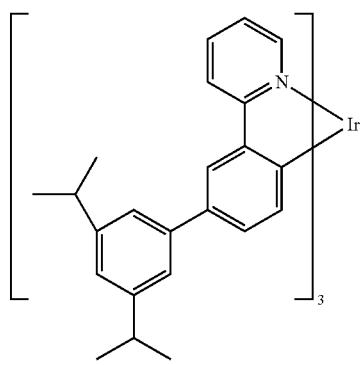
D-30
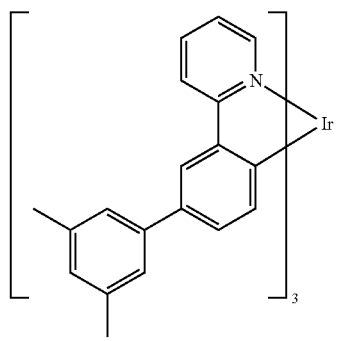

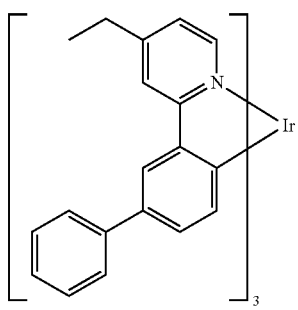
D-31
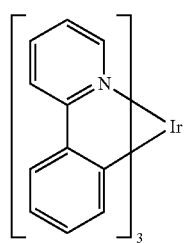
D-32
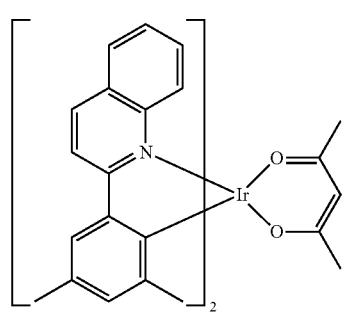
D-33
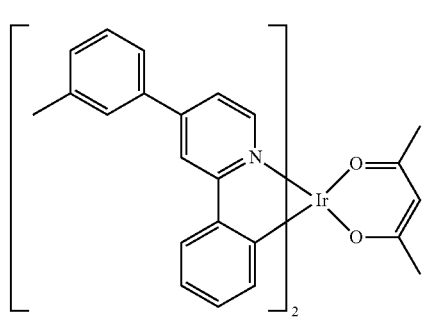
D-34
D-35
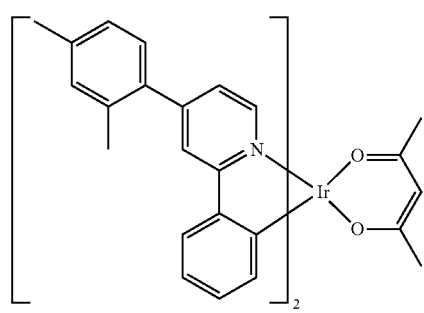
D-36
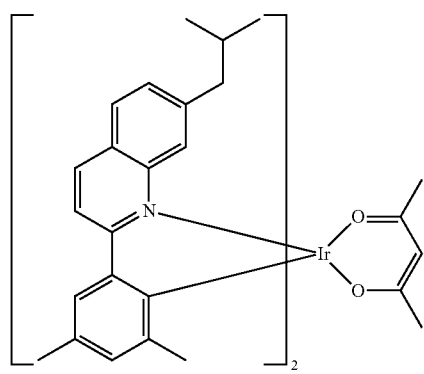
D-37
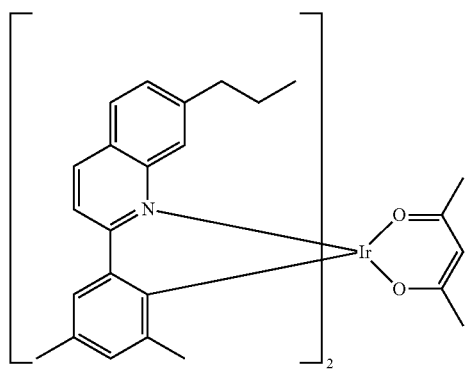
D-38
D-39
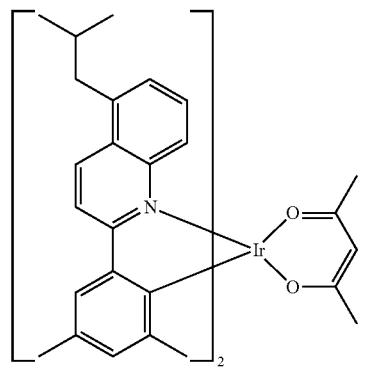

-continued
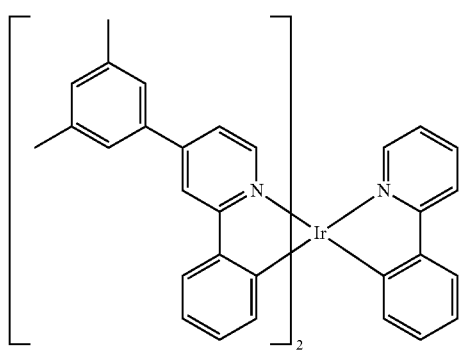 D-40
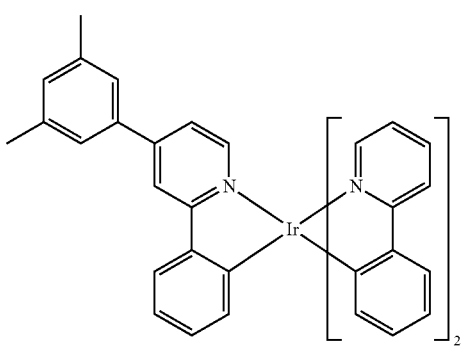 D-41
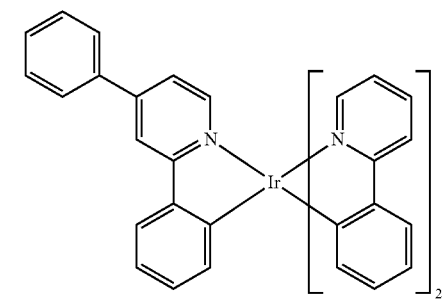 D-42
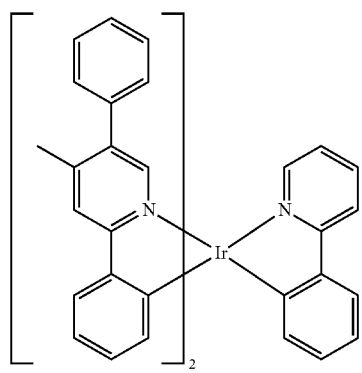 D-43
-continued
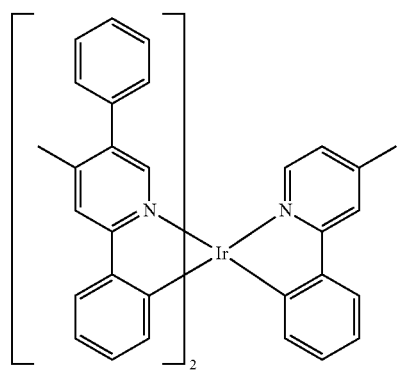 D-44
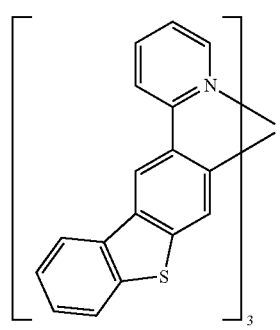 D-45
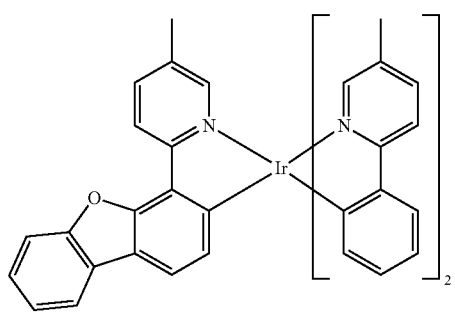 D-46
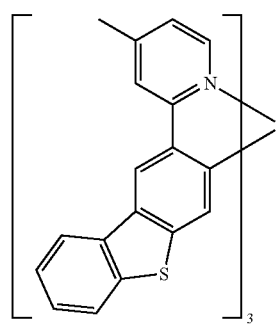 D-47
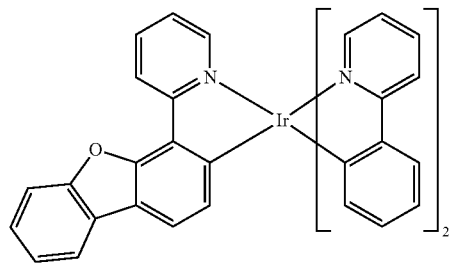 D-48

D-49 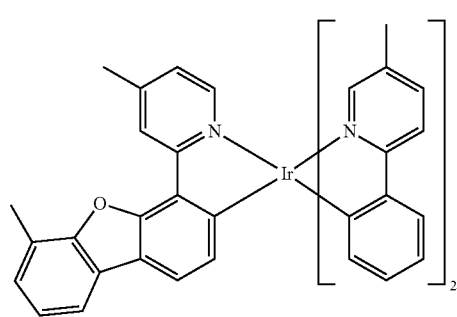
D-50 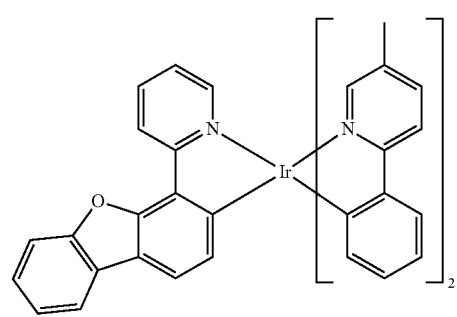
D-51 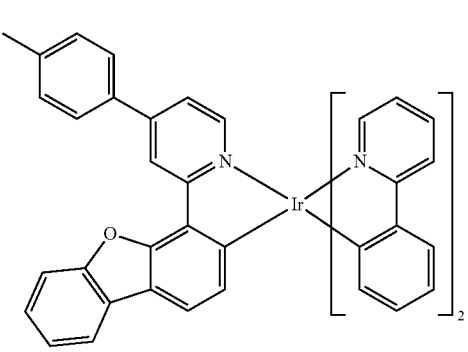
D-52 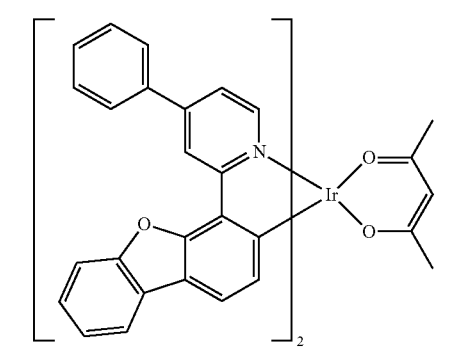
D-53 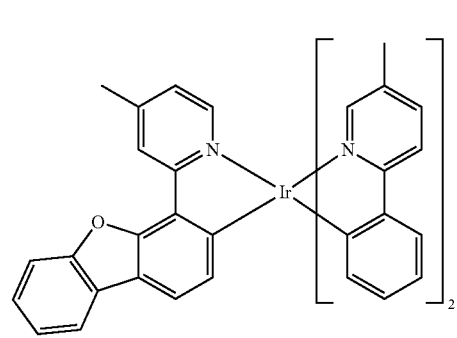
D-54 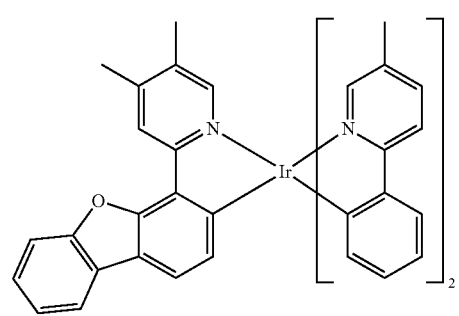
D-55 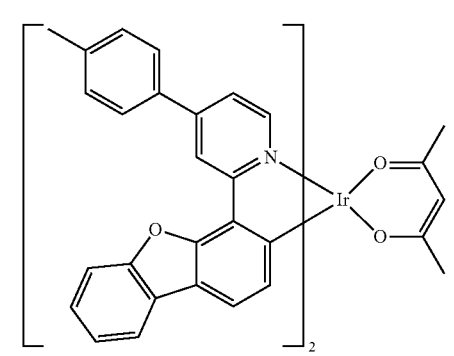
D-56 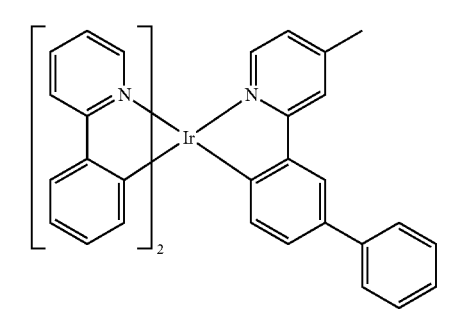
D-57 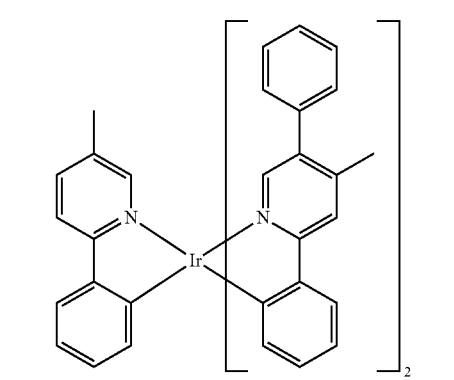

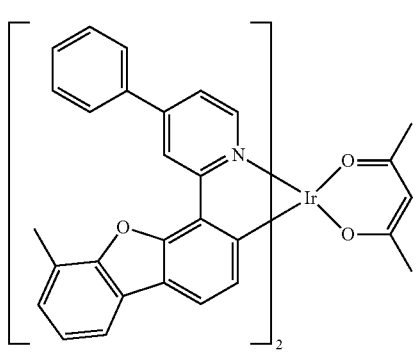
D-58
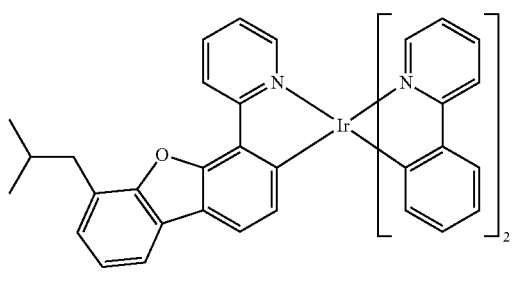
D-62
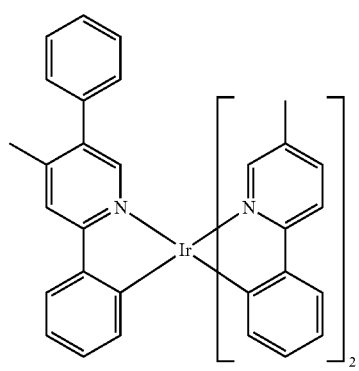
D-59
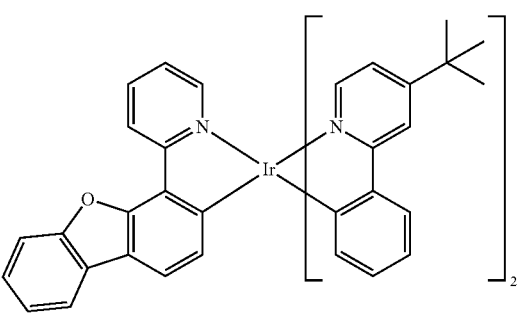
D-63
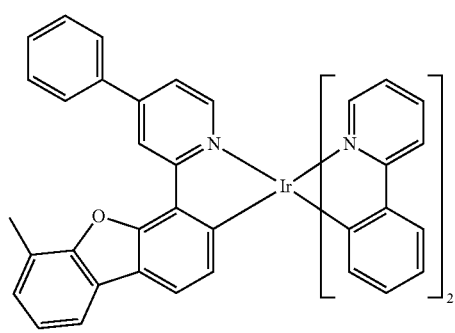
D-60
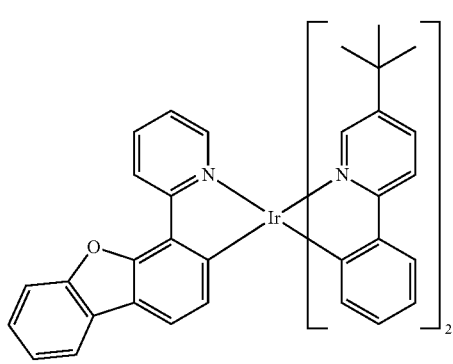
D-64
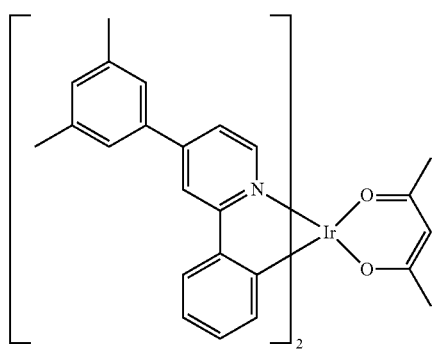
D-61
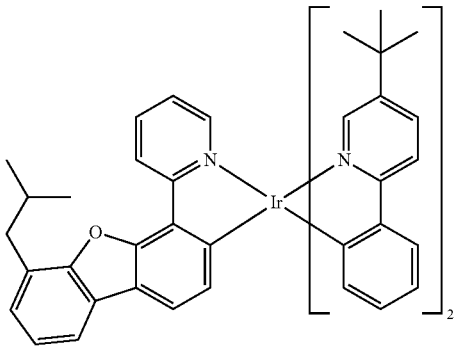
D-65

-continued
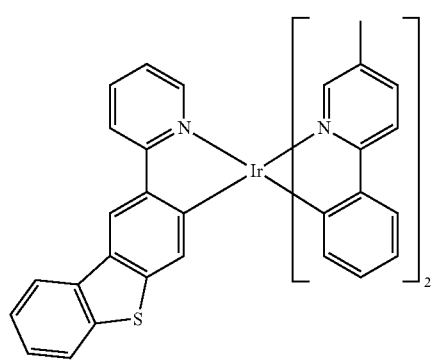
D-66
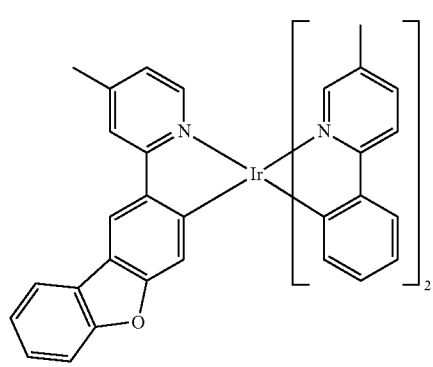
D-67
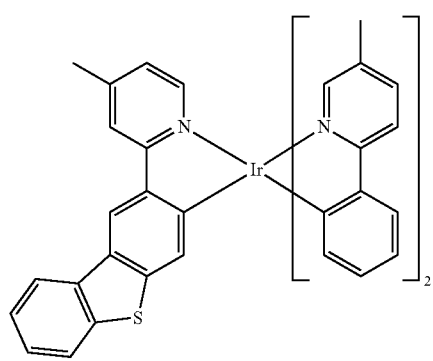
D-68
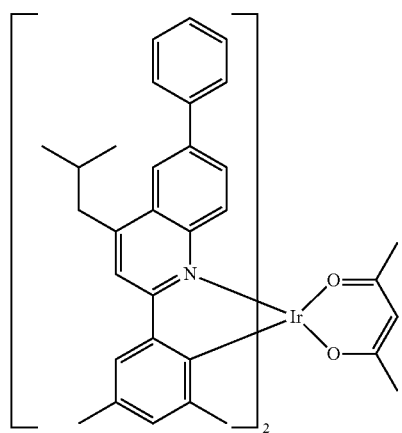
D-69
-continued
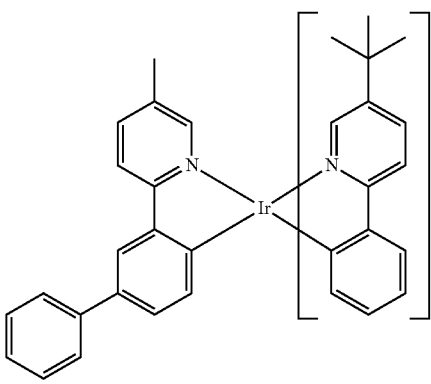
D-70
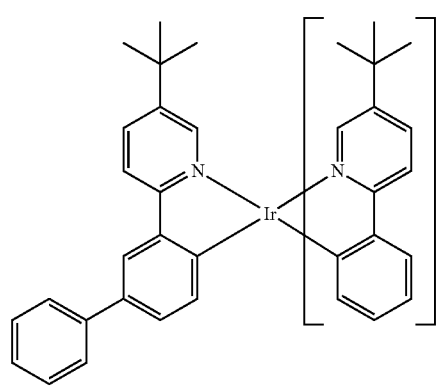
D-71
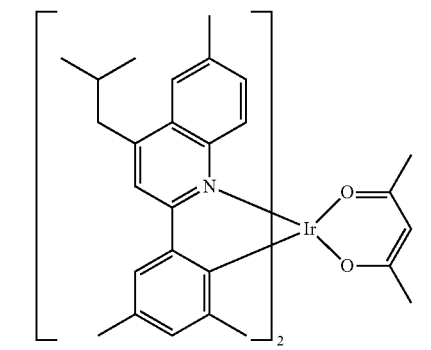
D-72
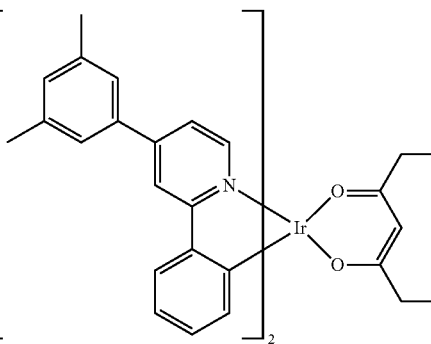
D-73

-continued
D-74
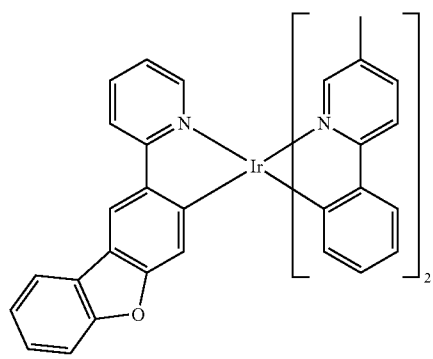
D-75
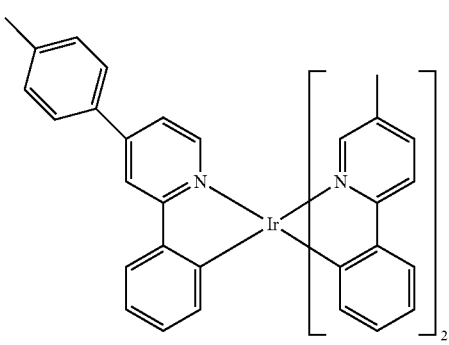
D-76
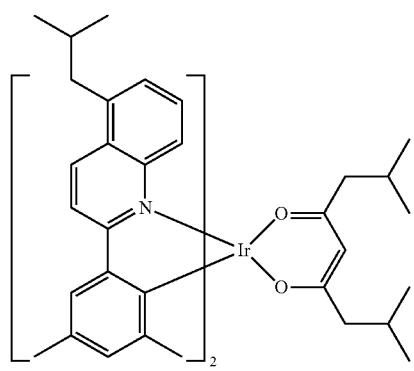
D-77
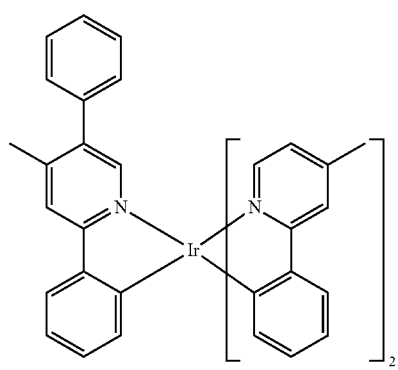
-continued
D-78
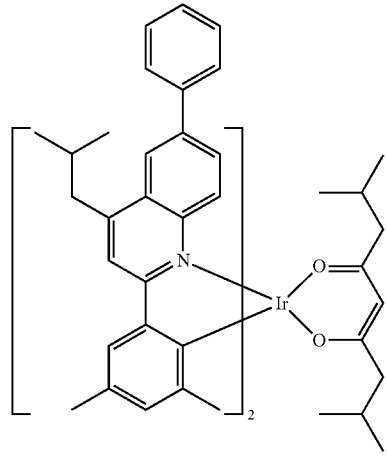
D-79
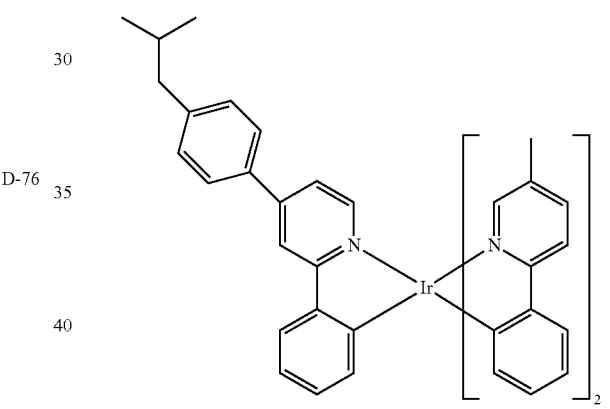
D-80
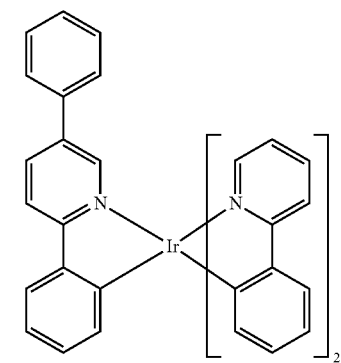

-continued
D-81
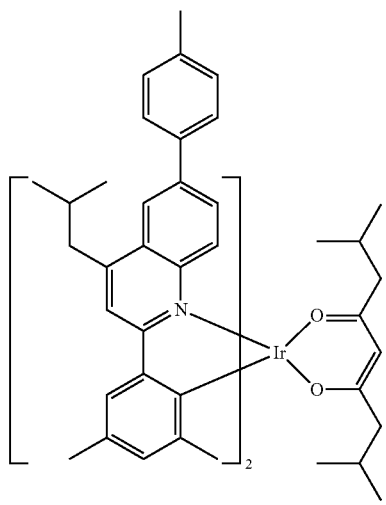
D-82
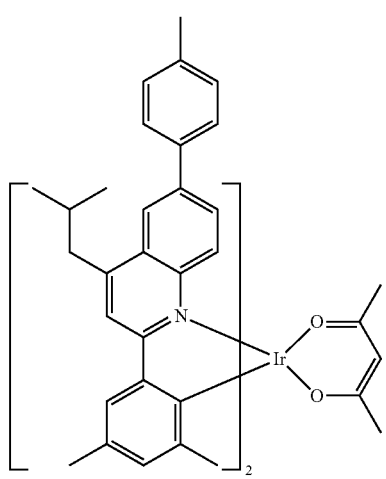
D-83
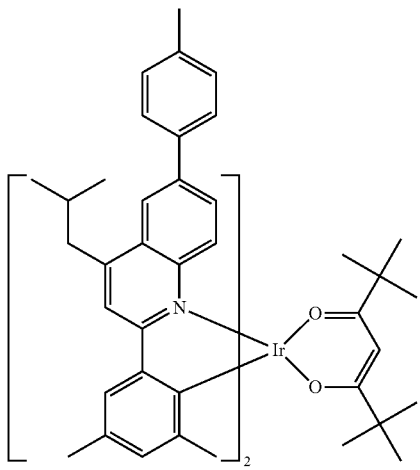
-continued
D-84
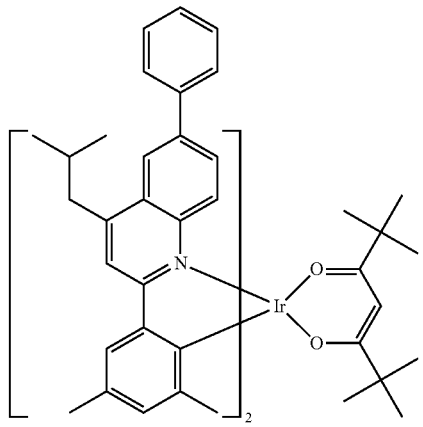
D-85
D-86
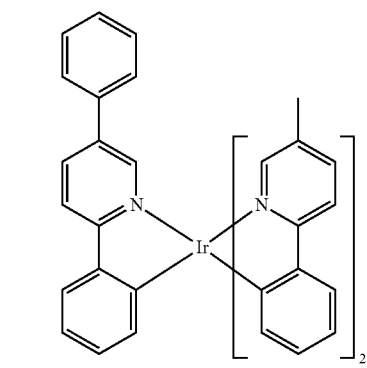
D-87

D-88
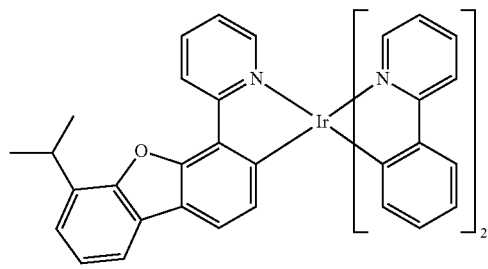
D-89
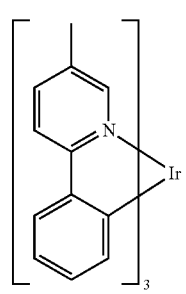
D-90
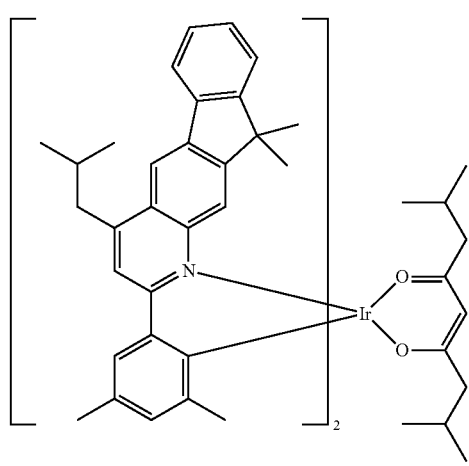
D-91
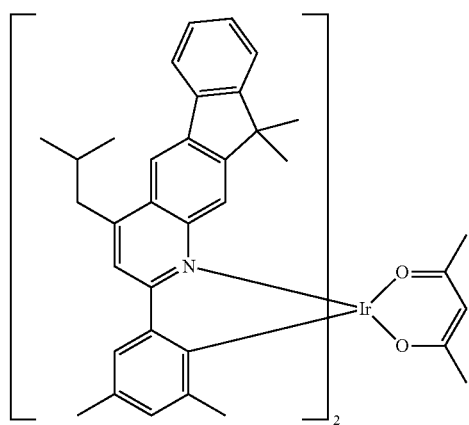
D-92
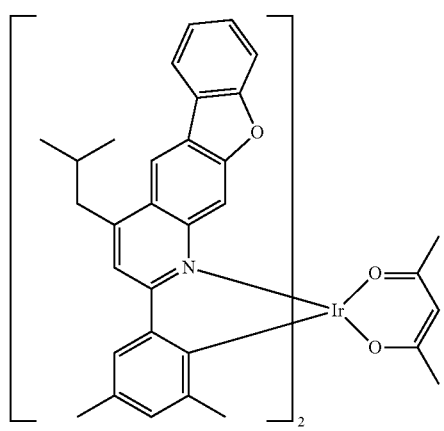
D-93
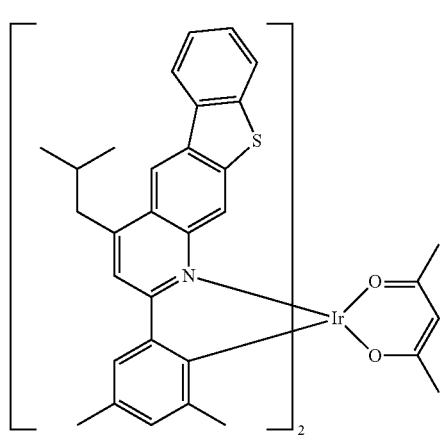
D-94
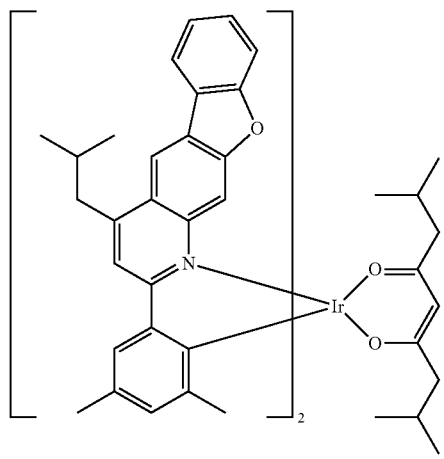

D-95
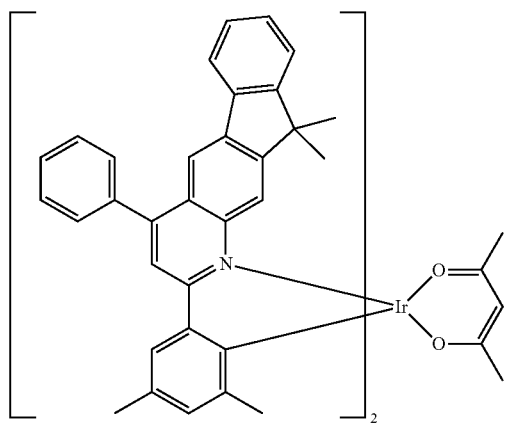
D-96
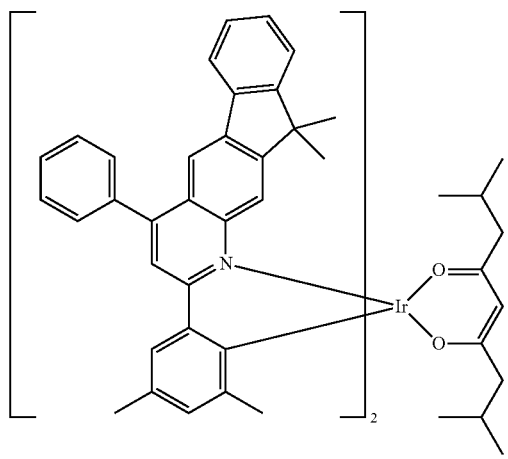
D-97
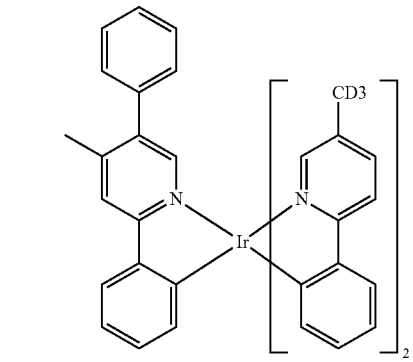
D-98
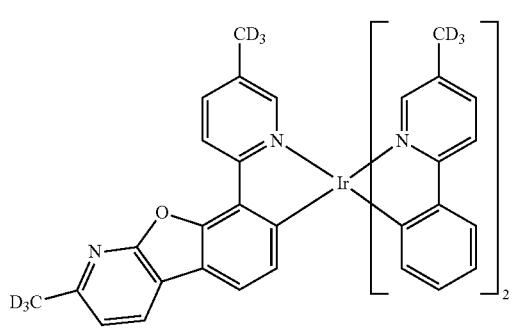
D-99
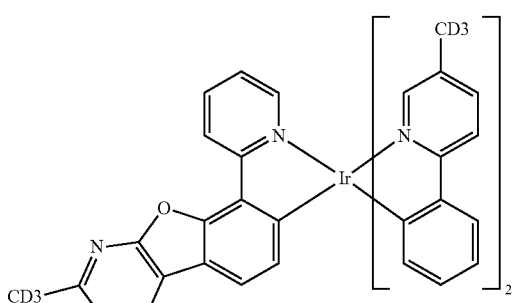
D-100
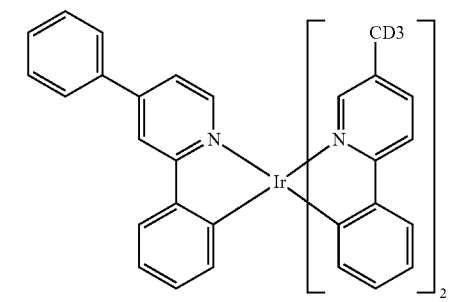
D-101
D-102

D-103
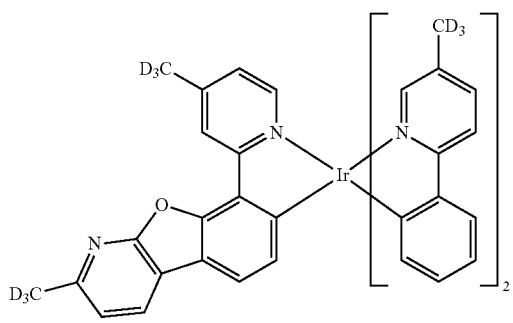
D-104
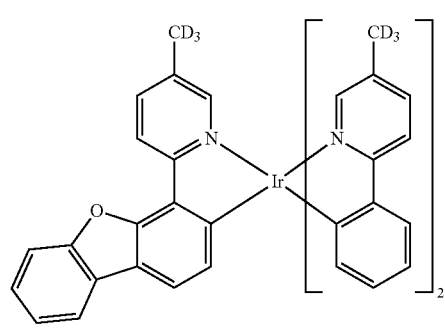
D-105
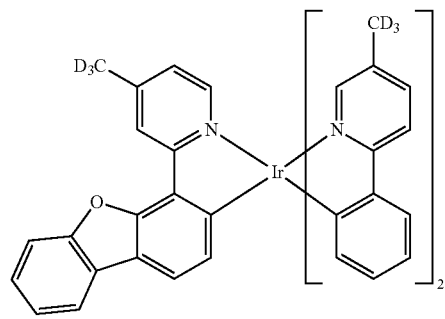
D-106
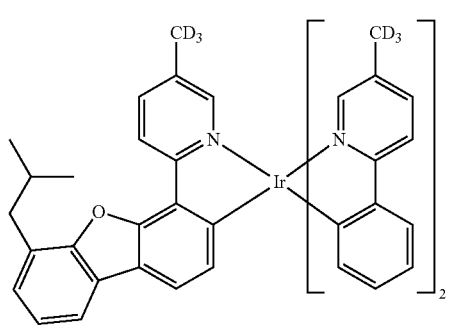
D-107
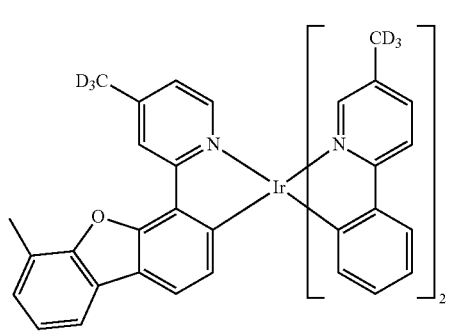
D-108
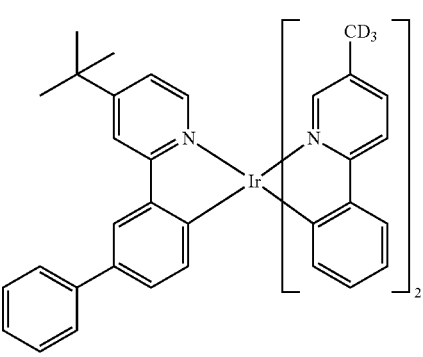
D-109
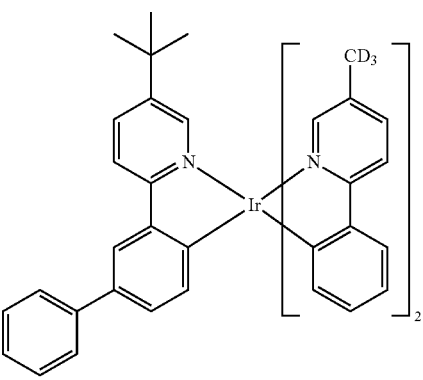
D-110
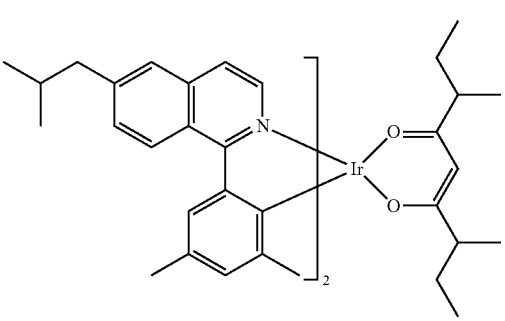
D-111
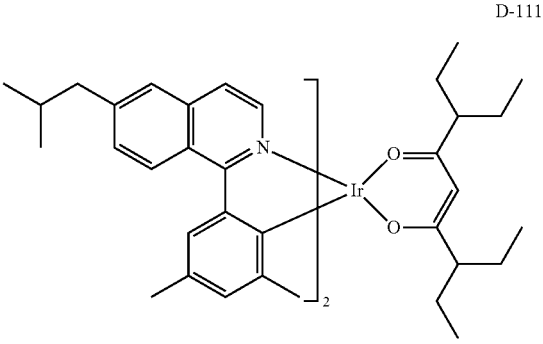

-continued

D-112
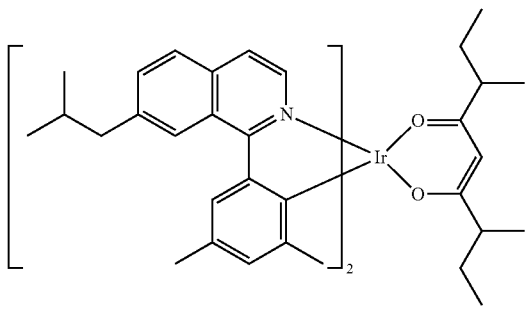

D-113
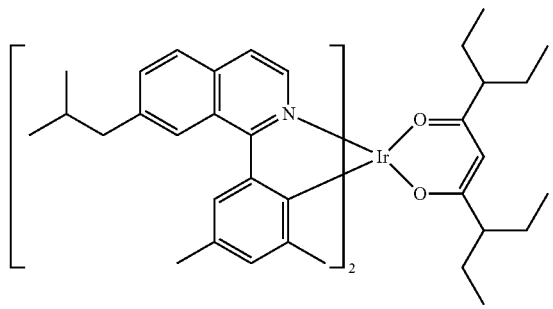

D-114
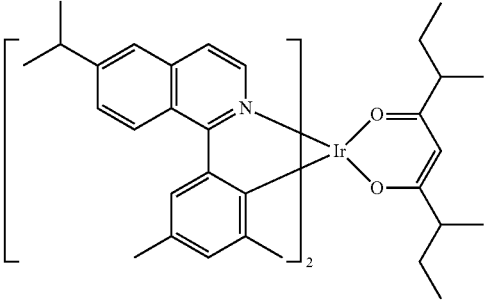

D-115
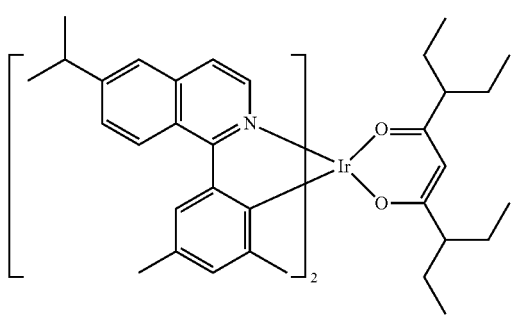

D-116
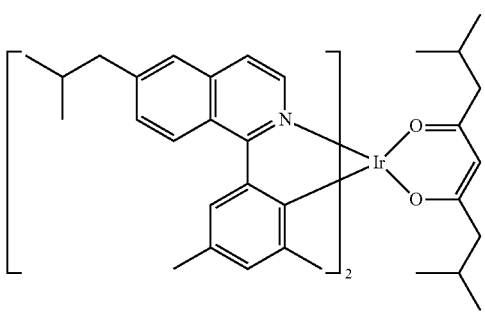

-continued

D-117
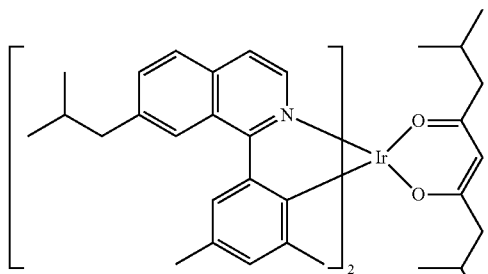

D-118
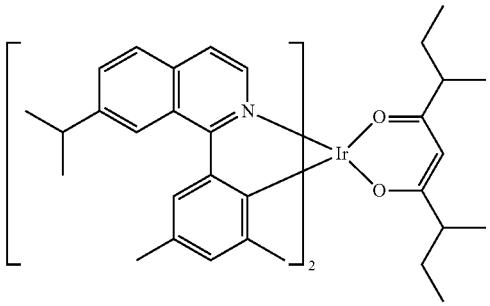

D-119
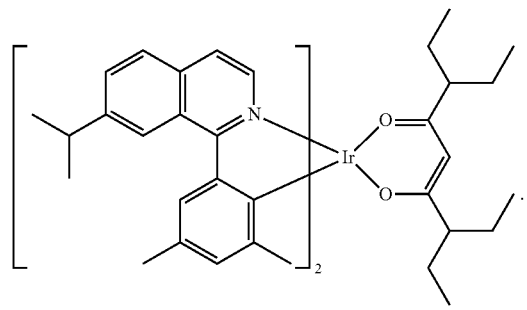

In order to form each layer constituting the organic electroluminescent device of the present disclosure, dry film-forming methods such as vacuum deposition, sputtering, plasma, ion plating methods, etc., or wet film-forming methods such as inkjet printing, nozzle printing, slot coating, spin coating, dip coating, flow coating methods, etc., can be used.

When using a wet film-forming method, a thin film is formed by dissolving or dispersing the material constituting each layer in suitable solvents, such as ethanol, chloroform, tetrahydrofuran, dioxane, etc. The solvents are not specifically limited as long as the material constituting each layer is soluble or dispersible in the solvents, which do not cause any problems in forming a layer.

The present disclosure may provide a display system comprising at least one organic electroluminescent compound represented by formula 1. That is, by using the organic electroluminescent compound of the present disclosure, a display system or a lighting system can be produced. Specifically, by using the organic electroluminescent compound of the present disclosure, a display system, for example, for smartphones, tablets, notebooks, PCs, TVs, or vehicles, or a lighting system, for example, an indoor or outdoor lighting system, can be produced.

Hereinafter, the preparation method of the organic electroluminescent compounds of the present disclosure, and the physical properties of the compounds will be explained in

Example 1: Preparation of Compound C-4

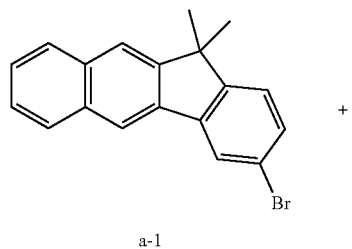

a-1

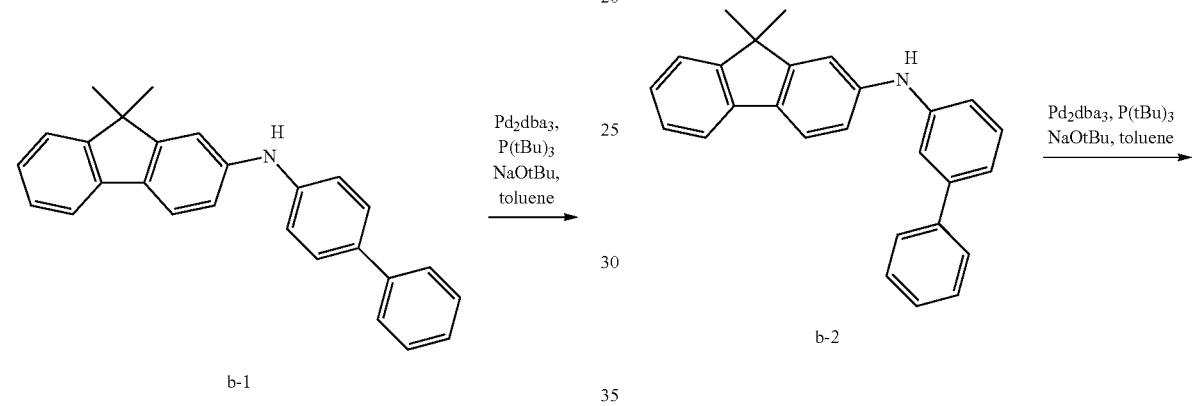

Example 2: Preparation of Compound C-5

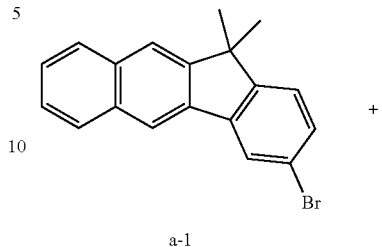

a-1

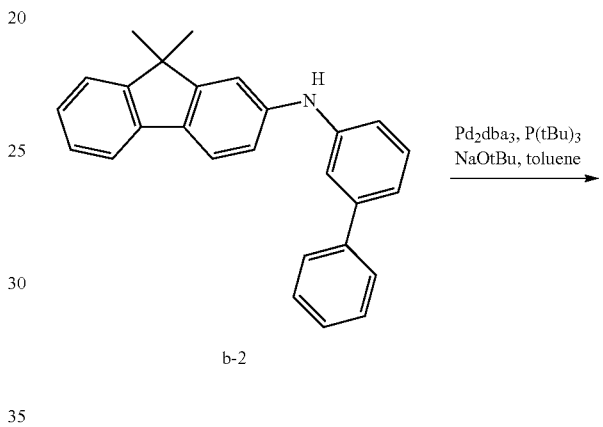

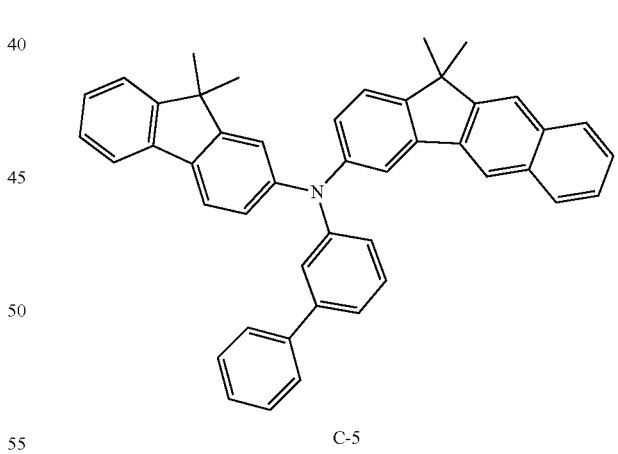

10 g of compound a-1 (31 mmol), 11.2 g of compound b-1 (31 mmol), 1.42 g of tris(dibenzylideneaceton)dipalladium (0) (1.6 mmol), 1.6 mL of tri-tert-butylphosphine (3.1 mmol, 50% toluene solution), 5.9 g of sodium tert-butoxide (62 mmol), and 154 mL of toluene were introduced into a reaction vessel, and the mixture was refluxed for 4 hours. The reaction solution was cooled to room temperature, and the solvent was then removed by a rotary evaporator. The residue was purified by column chromatography to obtain 8.3 g of compound C-4 (yield: 44%).

7.0 g of compound a-1 (22 mmol), 8.6 g of compound b-2 (24 mmol), 0.60 g of tris(dibenzylideneaceton)dipalladium (0) (0.66 mmol), 0.6 mL of tri-tert-butylphosphine (1.32 mmol, 50% toluene solution), 3.1 g of sodium tert-butoxide (32 mmol), and 110 mL of toluene were introduced into a reaction vessel, and the mixture was refluxed for 2 hours. The reaction solution was cooled to room temperature, and the solvent was then removed by a rotary evaporator. The residue was purified by column chromatography to obtain 0.9 g of compound C-5 (yield: 7%).

Example 3: Preparation of Compound C-6

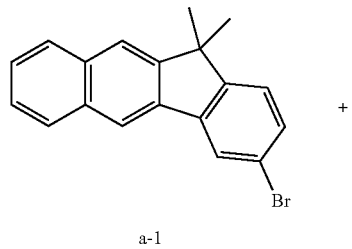

Example 4: Preparation of Compound C-7

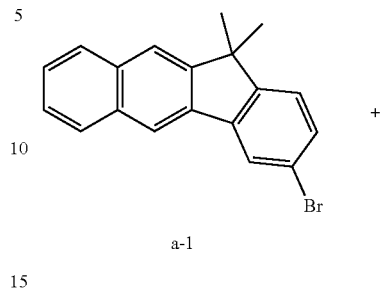

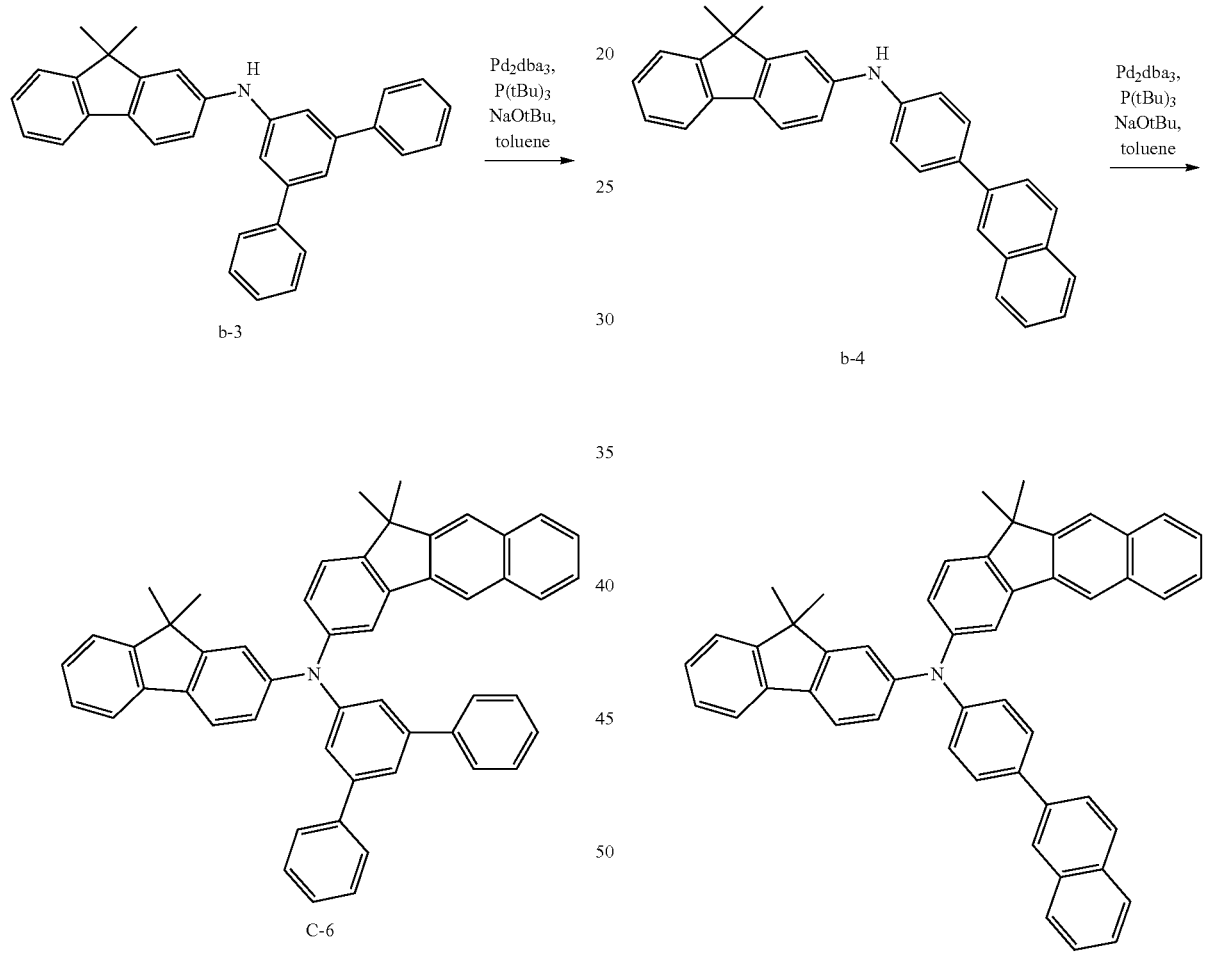

7.4 g of compound a-1 (23 mmol), 10.0 g of compound b-3 (23 mmol), 1.0 g of tris(dibenzylideneaceton)dipalladium(0) (1.2 mmol), 1.1 mL of tri-tert-butylphosphine (2.3 mmol, 50% toluene solution), 4.4 g of sodium tert-butoxide (46 mmol), and 114 mL of toluene were introduced into a reaction vessel, and the mixture was refluxed for 5 hours. The reaction solution was cooled to room temperature, and the solvent was then removed by a rotary evaporator. The residue was purified by column chromatography to obtain 4.9 g of compound C-6 (yield: 31%).

7.0 g of compound a-1 (22 mmol), 9.8 g of compound b-4 (24 mmol), 0.6 g of tris(dibenzylideneaceton)dipalladium(0) (0.66 mmol), 0.6 mL of tri-tert-butylphosphine (1.32 mmol, 50% toluene solution), 3.1 g of sodium tert-butoxide (32 mmol), and 110 mL of toluene were introduced into a reaction vessel, and the mixture was refluxed for 1 hour. The reaction solution was cooled to room temperature, and the solvent was then removed by a rotary evaporator. The residue was purified by column chromatography to obtain 2.8 g of compound C-7 (yield: 20%).

Example 5: Preparation of Compound C-8

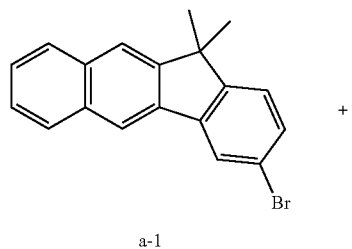

Example 6: Preparation of Compound C-24

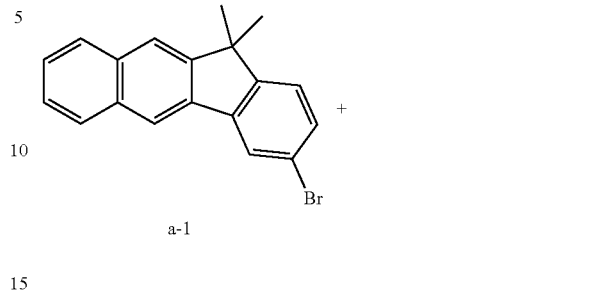

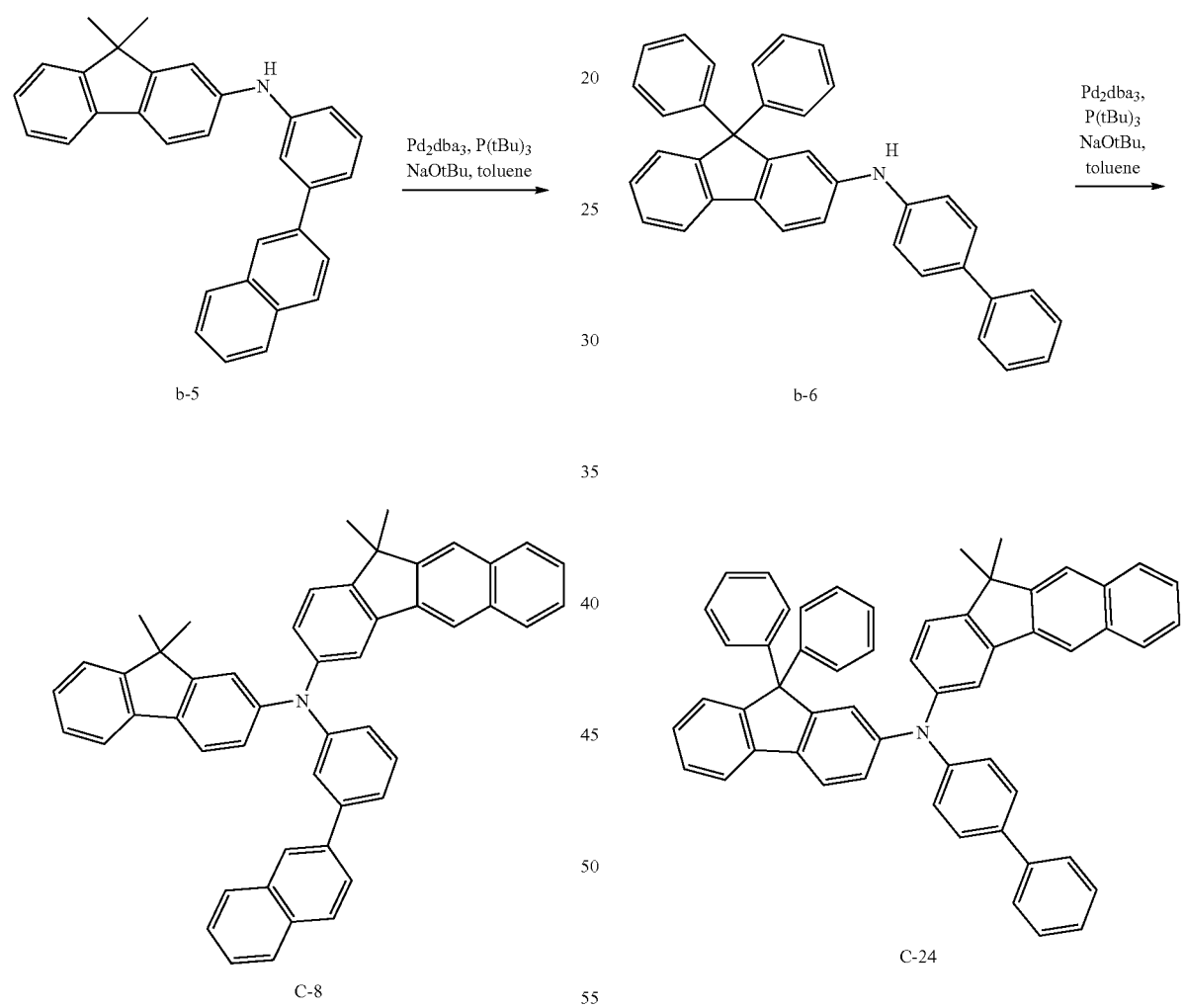

10.0 g of compound a-1 (31 mmol), 12.7 g of compound b-5 (24 mmol), 1.42 g of tris(dibenzylideneaceton)dipalladium(0) (1.6 mmol), 1.6 mL of tri-tert-butylphosphine (3.1 mmol, 50% toluene solution), 5.9 g of sodium tert-butoxide (62 mmol), and 154 mL of toluene were introduced into a reaction vessel, and the mixture was refluxed for 2 hours. The reaction solution was cooled to room temperature, and the solvent was then removed by a rotary evaporator. The residue was purified by column chromatography to obtain 2 g of compound C-8 (yield: 10%).

13 g of compound a-1 (40 mmol), 19.5 g of compound b-6 (40 mmol), 1.11 g of tris(dibenzylideneaceton)dipalladium(0) (1.2 mmol), 1.2 mL of tri-tert-butylphosphine (2.4 mmol, 50% toluene solution), 5.8 g of sodium tert-butoxide (60 mmol), and 223 mL of toluene were introduced into a reaction vessel, and the mixture was refluxed for 4 hours. The reaction solution was cooled to room temperature, and the solvent was then removed by a rotary evaporator. The residue was purified by column chromatography to obtain 15 g of compound C-24 (yield: 51%).

Example 7: Preparation of Compound C-2

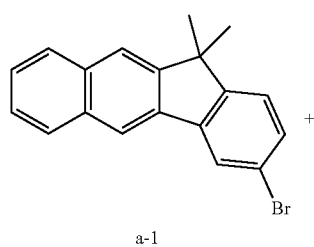

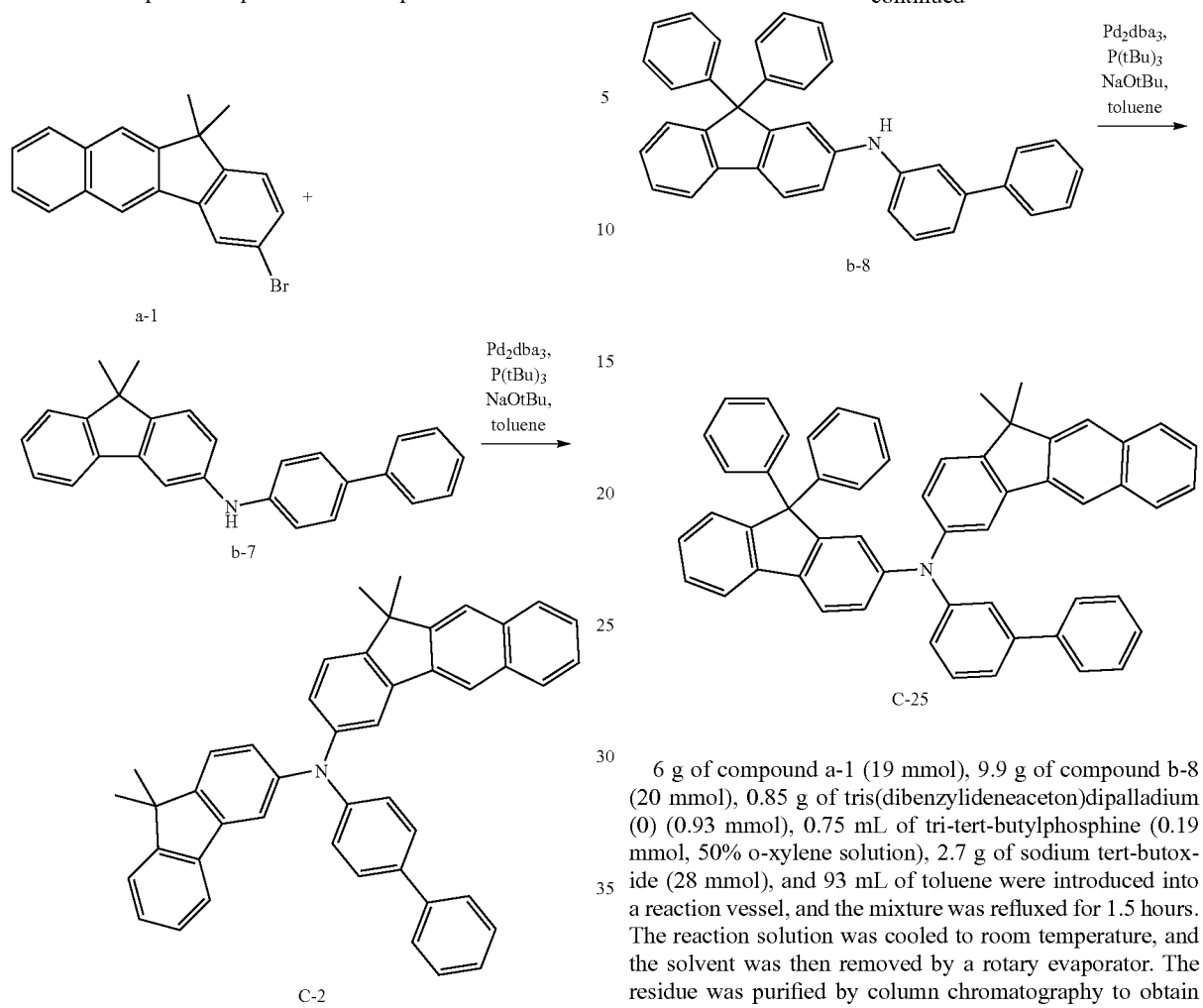

10 g of compound a-1 (31 mmol), 12.3 g of compound b-7 (34 mmol), 1.42 g of tris(dibenzylideneaceton)dipalladium (0) (1.6 mmol), 1.6 mL of tri-tert-butylphosphine (3.1 mmol, 50% toluene solution), 4.5 g of sodium tert-butoxide (46 mmol), and 160 mL of toluene were introduced into a reaction vessel, and the mixture was refluxed for 2 hours. The reaction solution was cooled to room temperature, and the solvent was then removed by a rotary evaporator. The residue was purified by column chromatography to obtain 6.3 g of compound C-2 (yield: 34%).

Example 8: Preparation of Compound C-25

6 g of compound a-1 (19 mmol), 9.9 g of compound b-8 (20 mmol), 0.85 g of tris(dibenzylideneaceton)dipalladium (0) (0.93 mmol), 0.75 mL of tri-tert-butylphosphine (0.19 mmol, 50% o-xylene solution), 2.7 g of sodium tert-butoxide (28 mmol), and 93 mL of toluene were introduced into a reaction vessel, and the mixture was refluxed for 1.5 hours. The reaction solution was cooled to room temperature, and the solvent was then removed by a rotary evaporator. The residue was purified by column chromatography to obtain 2.6 g of compound C-25 (yield: 19%).

Example 9: Preparation of Compound C-66

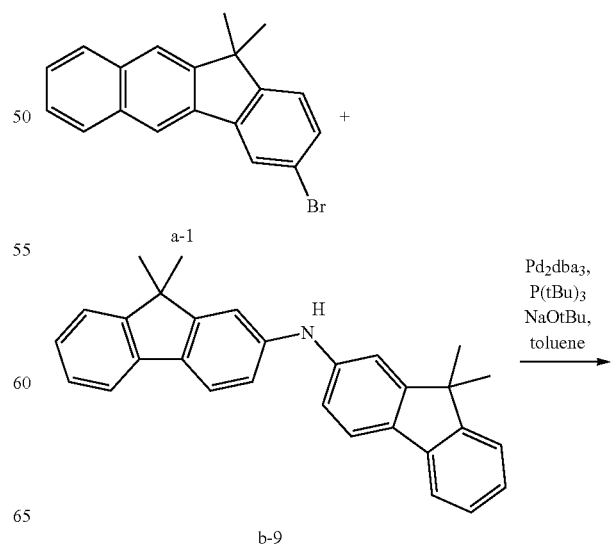

-continued

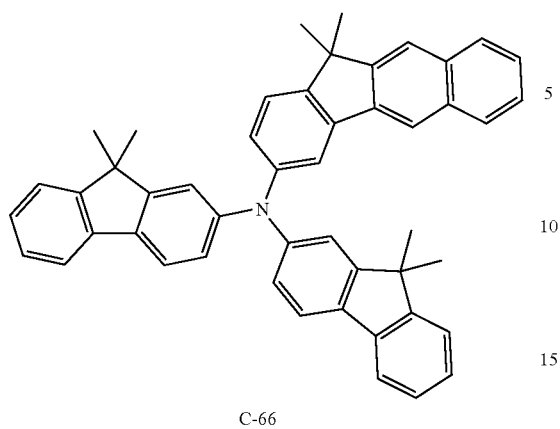

C-66

8 g of compound a-1 (25 mmol), 9.9 g of compound b-9 (25 mmol), 1.13 g of tris(dibenzylideneaceton)dipalladium (0) (1.25 mmol), 1 mL of tri-tert-butylphosphine (2.5 mmol, 50% o-xylene solution), 5.9 g of sodium tert-butoxide (62 mmol), and 125 mL of toluene were introduced into a reaction vessel, and the mixture was refluxed for 2 hours.

The reaction solution was cooled to room temperature, and the solvent was then removed by a rotary evaporator. The residue was purified by column chromatography to obtain 11 g of compound C-66 (yield: 69%).

Example 10: Preparation of Compound C-62

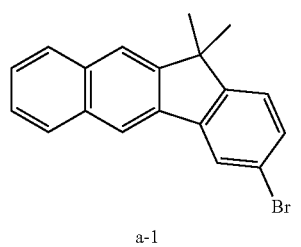

a-1

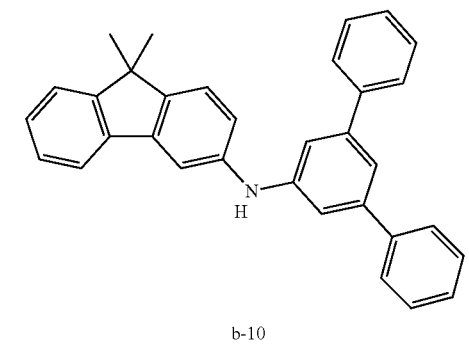

b-10

-continued

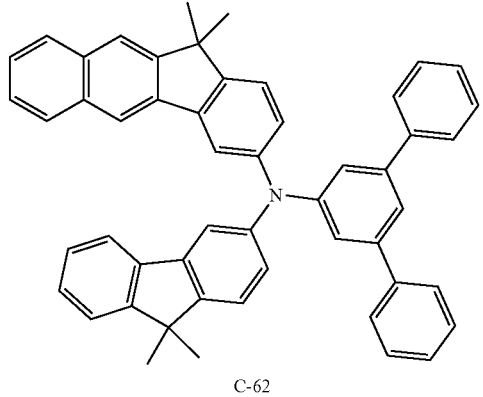

C-62

3.9 g of compound a-1 (12 mmol), 5.3 g of compound b-10 (12 mmol), 0.56 g of tris(dibenzylideneaceton)dipalladium(0) (0.6 mmol), 0.5 mL of tri-tert-butylphosphine (1.2 mmol, 50% o-xylene solution), 2.3 g of sodium tert-butoxide (24 mmol), and 61 mL of toluene were introduced into a reaction vessel, and the mixture was refluxed for 1 hour. The reaction solution was cooled to room temperature, and the solvent was then removed by a rotary evaporator. The residue was purified by column chromatography to obtain 5.3 g of compound C-62 (yield: 64%).

Example 11: Preparation of Compound C-61

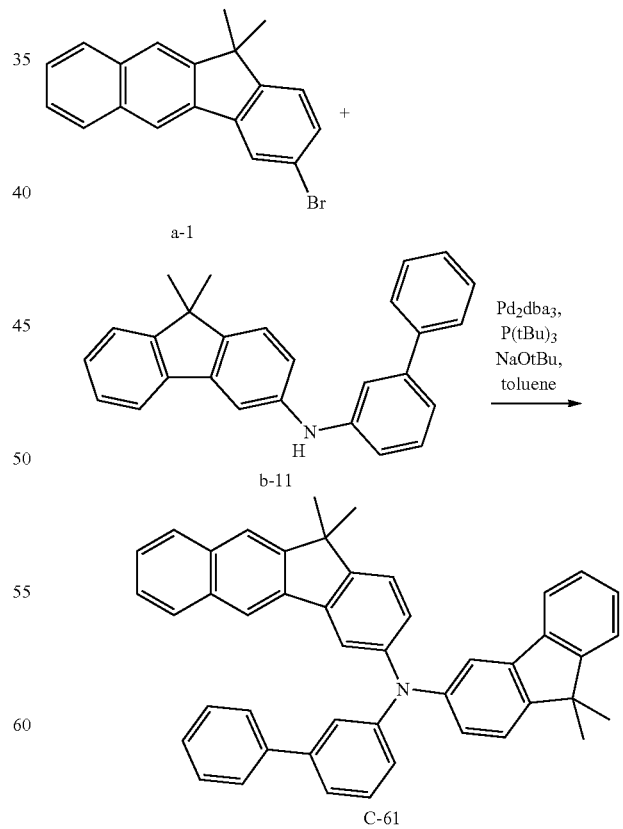

C-61

7.9 g of compound a-1 (24 mmol), 8.0 g of compound b-11 (22 mmol), 1.0 g of tris(dibenzylideneaceton)dipalladium(0) (1.1 mmol), 1 mL of tri-tert-butylphosphine (2.2 mmol, 50% o-xylene solution), 3.2 g of sodium tert-butoxide (33 mmol), and 110 mL of toluene were introduced into a reaction vessel, and the mixture was refluxed for 1 hour. The reaction solution was cooled to room temperature, and the solvent was then removed by a rotary evaporator. The residue was purified by column chromatography to obtain 8.5 g of compound C-61 (yield: 64%).

Example 12: Preparation of Compound C-63

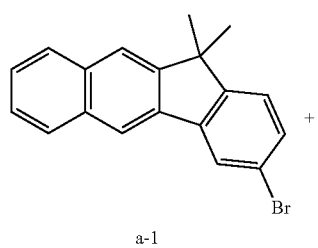

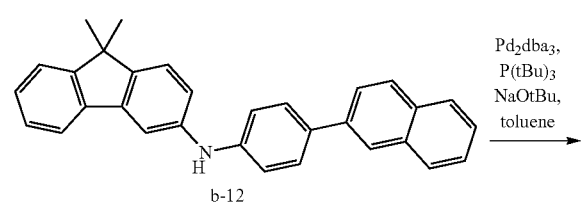

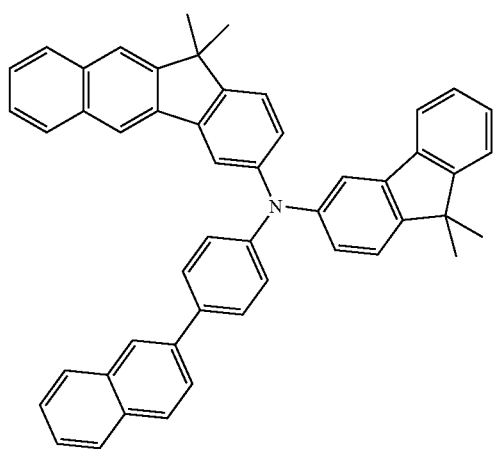

Example 13: Preparation of Compound C-67

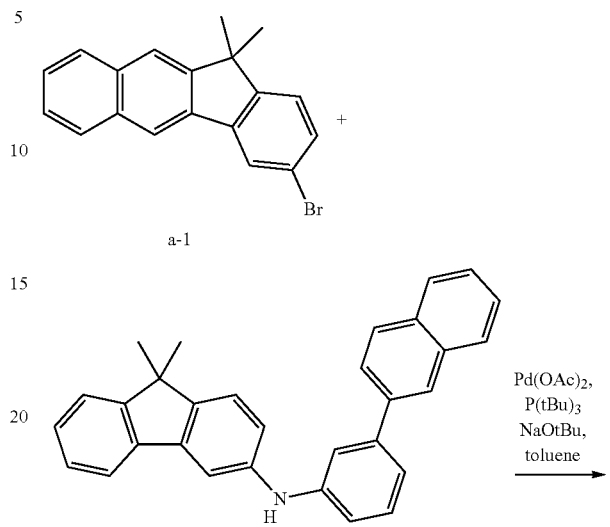

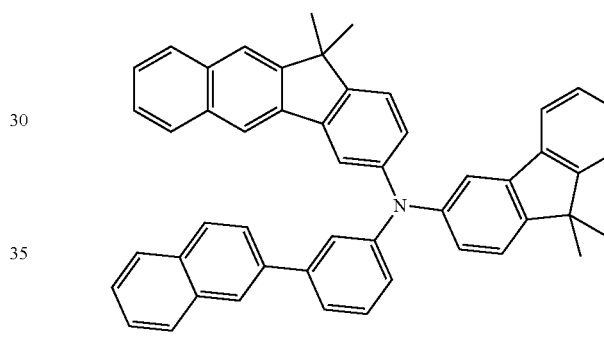

14.1 g of compound a-1 (44 mmol), 18.0 g of compound b-13 (44 mmol), 0.49 g of palladium(II)acetate (2.2 mmol), 1.8 mL of tri-tert-butylphosphine (4.4 mmol, 50% o-xylene solution), 9.2 g of sodium tert-butoxide (96 mmol), and 200 mL of toluene were introduced into a reaction vessel, and the mixture was refluxed for 1 hour. The reaction solution was cooled to room temperature, and the solvent was then removed by a rotary evaporator. The residue was purified by column chromatography to obtain 3.5 g of compound C-67 (yield: 12%).

Example 14: Preparation of Compound C-68

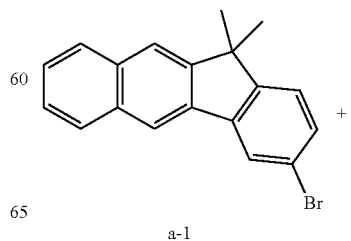

8.6 g of compound a-1 (26 mmol), 12.0 g of compound b-12 (29 mmol), 1.2 g of tris(dibenzylideneaceton)dipalladium(0) (1.3 mmol), 1.3 mL of tri-tert-butylphosphine (2.6 mmol, 50% o-xylene solution), 3.8 g of sodium tert-butoxide (40 mmol), and 133 mL of toluene were introduced into a reaction vessel, and the mixture was refluxed for 1 hour. The reaction solution was cooled to room temperature, and the solvent was then removed by a rotary evaporator. The residue was purified by column chromatography to obtain 11 g of compound C-63 (yield: 64%).

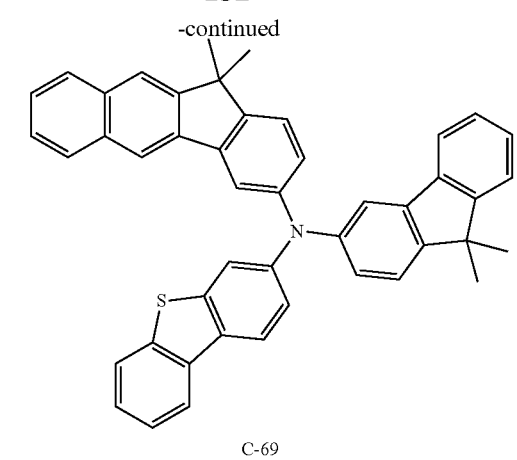

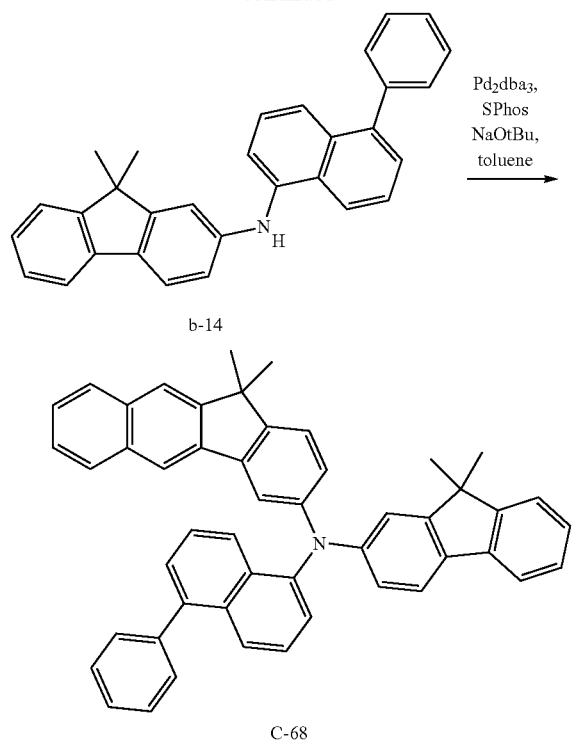

4 g of compound a-1 (12 mmol), 5.1 g of compound b-14 (12 mmol), 0.57 g of tris(dibenzylideneaceton)dipalladium (0) (0.6 mmol), 0.51 g of SPhos (1.2 mmol), 3.0 g of sodium tert-butoxide (3.1 mmol), and 60 mL of toluene were introduced into a reaction vessel, and the mixture was refluxed for 1 hour. The reaction solution was cooled to room temperature, and the solvent was then removed by a rotary evaporator. The residue was purified by column chromatography to obtain 6.1 g of compound C-68 (yield: 75%).

Example 15: Preparation of Compound C-69

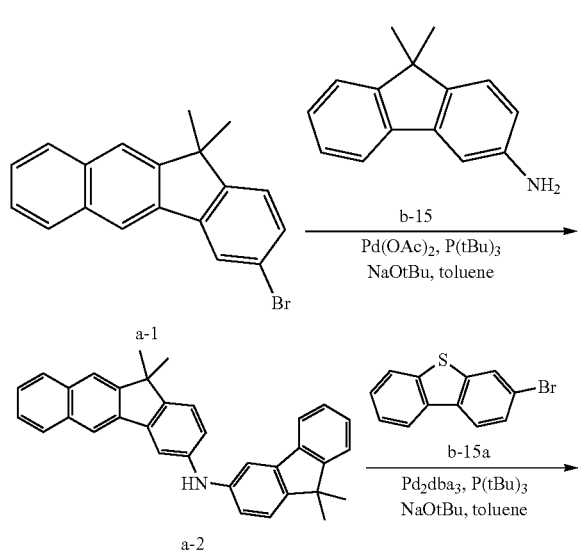

44.6 g of compound a-1 (138 mmol), 34.7 g of compound b-15 (166 mmol), 1.55 g of palladium(II)acetate (6.9 mmol), 6.8 mL of tri-tert-butylphosphine (13.8 mmol, 50% o-xylene solution), 26.5 g of sodium tert-butoxide (276 mmol), and 690 mL of toluene were introduced into a reaction vessel, and the mixture was refluxed for 8 hours. The reaction solution was cooled to room temperature, and the solvent was then removed by a rotary evaporator. The residue was purified by column chromatography to obtain 12 g of compound a-2 (yield: 19%). Thereafter, 6 g of compound a-2 (13 mmol), 4.2 g of compound b-15a (16 mmol), 0.61 g of tris(dibenzylideneaceton)dipalladium(0) (0.65 mmol), 0.66 mL of tri-tert-butylphosphine (1.3 mmol, 50% o-xylene solution), 1.9 g of sodium tert-butoxide (1.95 mmol), and 66 mL of toluene were introduced into a reaction vessel, and the mixture was refluxed for 0.5 hour. The reaction solution was cooled to room temperature, and the solvent was then removed by a rotary evaporator. The residue was purified by column chromatography to obtain 6.8 g of compound C-69 (yield: 81%).

Example 16: Preparation of Compound C-70

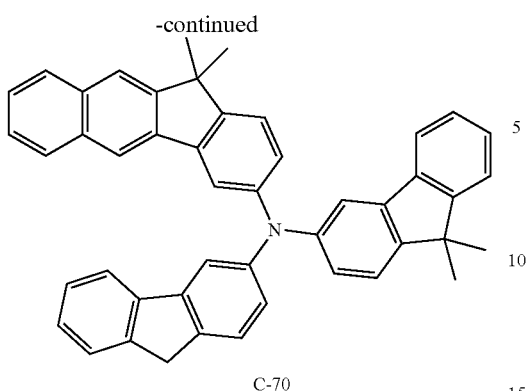

C-70

21 g of compound a-2 (46 mmol), 11.4 g of compound b-16 (46 mmol), 0.52 g of palladium(II)acetate (2.3 mmol), 1.9 mL of tri-tert-butylphosphine (4.6 mmol, 50% o-xylene solution), 9.8 g of sodium tert-butoxide (102 mmol), and 230 mL of toluene were introduced into a reaction vessel, and the mixture was refluxed for 1 hour. The reaction solution was cooled to room temperature, and the solvent was then removed by a rotary evaporator. The residue was purified by column chromatography to obtain 2.5 g of compound C-70 (yield: 8.7%).

Example 17: Preparation of Compound C-71

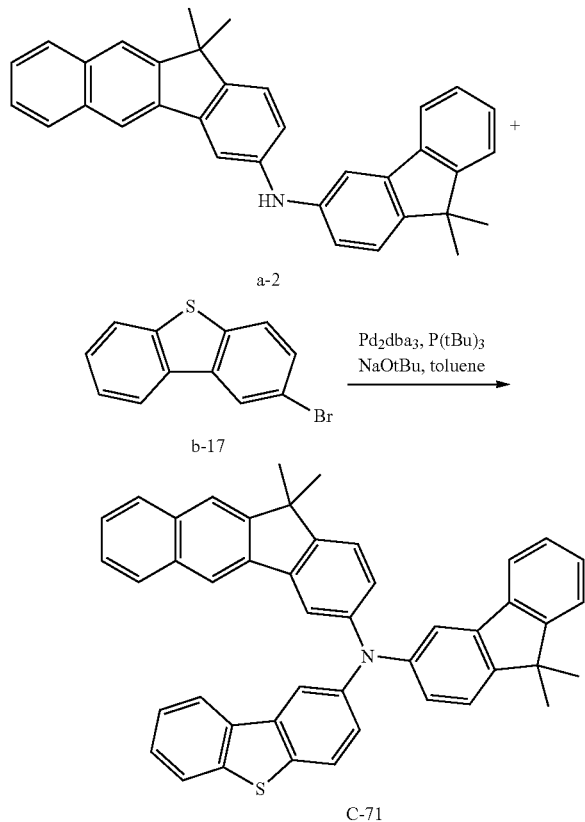

6 g of compound a-2 (13 mmol), 4.2 g of compound b-17 (16 mmol), 0.61 g of tris(dibenzylideneaceton)dipalladium (0) (0.65 mmol), 0.66 mL of tri-tert-butylphosphine (1.3 mmol, 50% o-xylene solution), 1.9 g of sodium tert-butoxide (1.95 mmol), and 66 mL of toluene were introduced into a reaction vessel, and the mixture was refluxed for 0.5 hour. The reaction solution was cooled to room temperature, and the solvent was then removed by a rotary evaporator. The residue was purified by column chromatography to obtain 4.5 g of compound C-71 (yield: 53%).

Example 18: Preparation of Compound C-10

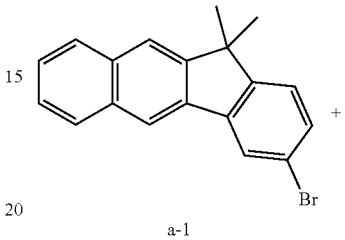

a-1

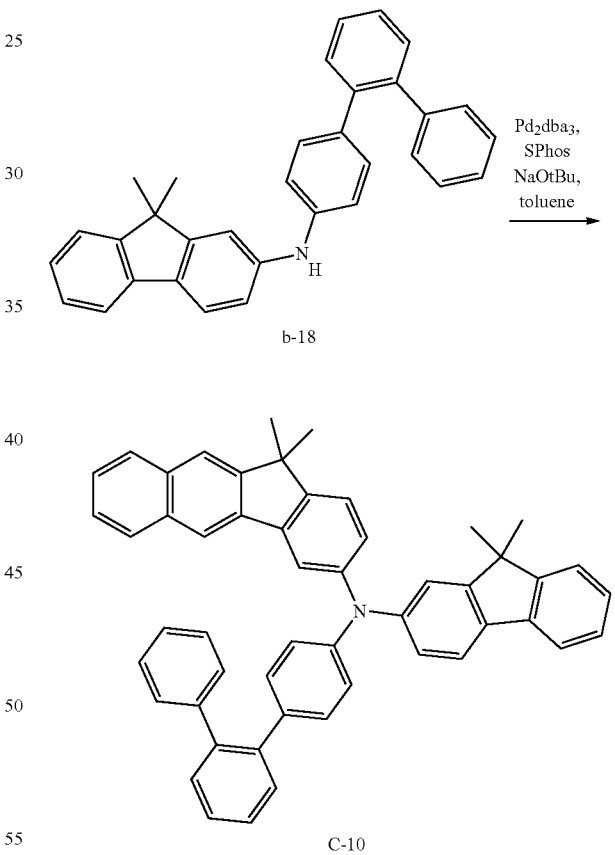

5.1 g of compound a-1 (16 mmol), 6.9 g of compound b-18 (16 mmol), 0.72 g of tris(dibenzylideneaceton)dipalladium(0) (0.80 mmol), 0.65 g of SPhos (1.6 mmol), 3.8 g of sodium tert-butoxide (3.9 mmol), and 72 mL of toluene were introduced into a reaction vessel, and the mixture was refluxed for 0.5 hour. The reaction solution was cooled to room temperature, and the solvent was then removed by a rotary evaporator. The residue was purified by column chromatography to obtain 6.9 g of compound C-10 (yield: 64%).

Example 19: Preparation of Compound C-72

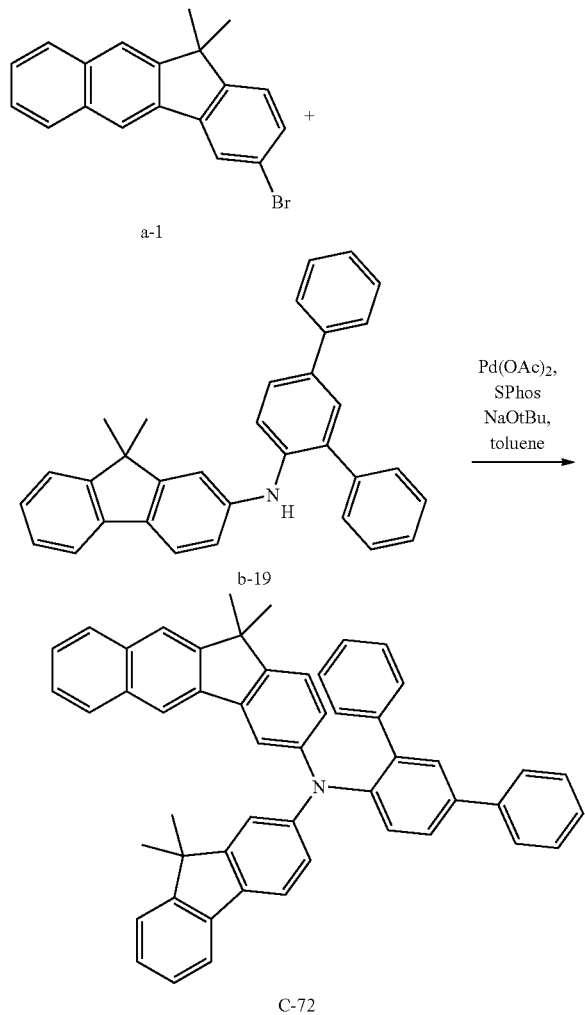

5.0 g of compound a-1 (15 mmol), 6.8 g of compound b-19 (15 mmol), 0.17 g of palladium(II)acetate (0.75 mmol), 0.64 g of SPhos (1.5 mmol), 3.7 g of sodium tert-butoxide (3.9 mmol), and 77 mL of toluene were introduced into a reaction vessel, and the mixture was refluxed for 1 hour. The reaction solution was cooled to room temperature, and the solvent was then removed by a rotary evaporator. The residue was purified by column chromatography to obtain 1.5 g of compound C-72 (yield: 14%).

The physical properties of the compounds prepared in the Examples are shown in Table 1 below.

TABLE 1

| Example | Compound | Yield (%) | UV (nm) | PL (nm) | MP (° C.) | MS/EIMS(M + H) Found | MS/EIMS(M + H) Calculated |
|---|---|---|---|---|---|---|---|
| 1 | C-4 | 44 | 394 | 457 | 155 | 604.2 | 604.3 |
| 2 | C-5 | 7 | 344 | 419 | 147 | 604.1 | 604.3 |
| 3 | C-6 | 31 | 378 | 445 | 205 | 680.2 | 680.3 |
| 4 | C-7 | 20 | 344 | 418 | 260 | 654.2 | 654.3 |
| 5 | C-8 | 10 | 396 | 449 | 139 | 654.2 | 654.3 |
| 6 | C-24 | 51 | 334 | 417 | 180 | 728.1 | 728.3 |
| 7 | C-2 | 34 | 410 | 444 | 171 | 604.2 | 604.3 |
| 8 | C-25 | 19 | 280 | 415 | 202 | 728.2 | 728.3 |
| 9 | C-66 | 69 | 346 | 425 | 260 | 644.2 | 644.3 |
| 10 | C-62 | 64 | 315 | 415 | 276 | 680.2 | 680.3 |
| 11 | C-61 | 64 | 314 | 413 | 199 | 604.2 | 604.3 |
| 12 | C-63 | 64 | 281 | 415 | 240 | 654.2 | 654.3 |
| 13 | C-67 | 12 | 306 | 414 | 198 | 654.2 | 654.3 |
| 14 | C-68 | 75 | 344 | 438 | 264 | 654.2 | 654.3 |
| 15 | C-69 | 81 | 282 | 414 | 200 | 634.2 | 634.3 |
| 16 | C-70 | 8.7 | 281 | 419 | 186 | 616.2 | 616.3 |
| 17 | C-71 | 53 | 316 | 422 | 209 | 634.2 | 634.3 |
| 18 | C-10 | 64 | 344 | 421 | 204 | 680.1 | 680.3 |
| 19 | C-72 | 14 | 349 | 420 | 178 | 680.4 | 680.3 |

Hereinafter, it is discussed whether it is possible to improve the driving voltage, luminous efficiency, and lifespan properties of an organic light-emitting diode device (OLED device) by comprising the compound represented by formula 1. However, the following Examples are intended to explain the properties of the OLED device comprising the compound according to the present disclosure, and the present disclosure is not limited thereto.

Device Examples 1 to 14: Production of an OLED Device According to the Present Disclosure An OLED device comprising the organic electroluminescent compound according to the present disclosure was produced as follows. A transparent electrode indium tin oxide (ITO) thin film (10 Ω/sq) on a glass substrate for an OLED device (Geomatec, Japan) was subjected to an ultrasonic washing with acetone and isopropanol, sequentially, and was then stored in isopropanol. Next, the ITO substrate was mounted on a substrate holder of a vacuum vapor depositing apparatus. Compound HI-1 was introduced into a cell of said vacuum vapor depositing apparatus, and then the pressure in the chamber of said apparatus was controlled to $10^{-6}$ torr. Thereafter, an electric current was applied to the cell to evaporate the above-introduced material, thereby forming a first hole injection layer having a thickness of 90 nm on the ITO substrate. Compound HI-2 was then introduced into another cell of said vacuum vapor depositing apparatus, and was evaporated by applying an electric current to the cell, thereby forming a second hole injection layer having a thickness of 5 nm on the first hole injection layer. Compound HT-1 was introduced into another cell of said vacuum vapor depositing apparatus, and was evaporated by applying an electric current to the cell, thereby forming a first hole transport layer having a thickness of 10 nm on the second hole injection layer. The second hole transport layer (auxiliary layer) compound shown in Table 2 below was introduced into another cell of said vacuum vapor depositing apparatus, and was evaporated by applying an electric current to the cell, thereby forming a second hole transport layer (auxiliary layer) having a thickness of 60 nm on the first hole transport layer. After forming the hole injection layers and the hole transport layers, a light-emitting layer was then deposited as follows. Compound H-1 was introduced into one cell of the vacuum vapor depositing apparatus as a host, and compound D-39 was introduced into another cell as a dopant. The two materials were evaporated and were deposited in a doping amount of 2 wt % (the amount of dopant) based on the total amount of the dopant and host to form a light-emitting layer having a thickness of 40 nm on the second hole transport layer. Compound ET-1 and compound EI-1 were then introduced into another two cells, evaporated at the rate of 1:1, and deposited to form an electron transport layer having a thickness of 35 nm on the light-emitting layer. Next, after compound EI-1 as an electron injection layer having a thickness of 2 nm was deposited on the electron transport layer, an Al cathode having a thickness of 80 nm was deposited by another vacuum vapor deposition apparatus on the electron injection layer. Thus, an OLED device was produced.

Comparative Examples 1 to 7: Production of an OLED Device not According to the Present Disclosure OLED devices were produced in the same manner as in Device Example 1, except for using the compounds shown in Table 2 below for the second hole transport layer.

The compounds used in Device Examples 1 to 14 and Comparative Examples 1 to 7 are as follows.

D-39

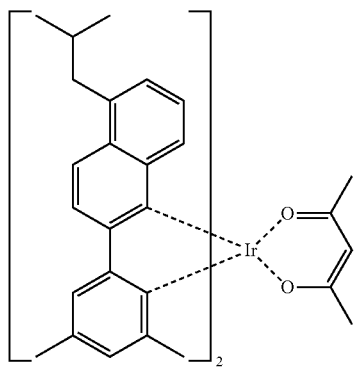

HI-1

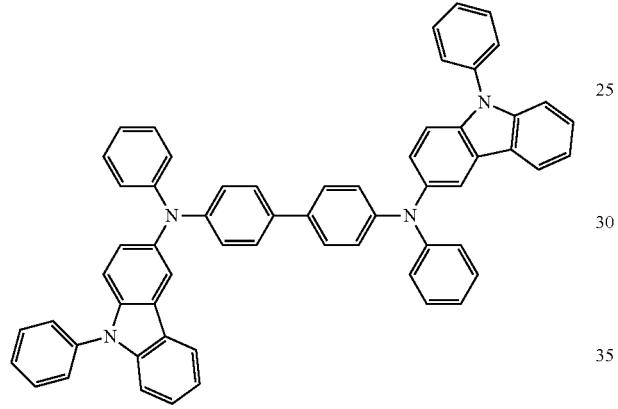

ET-1

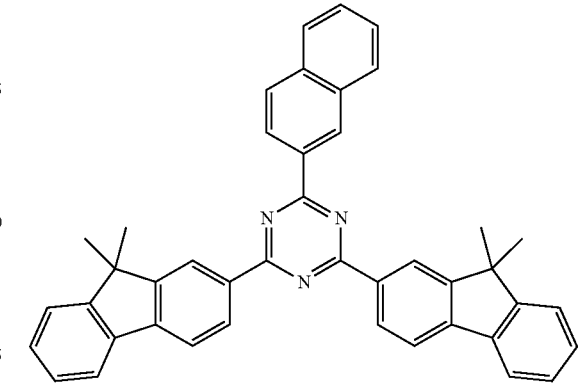

HI-2

EI-1

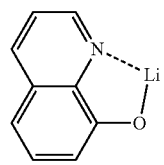

HT-1

H-1

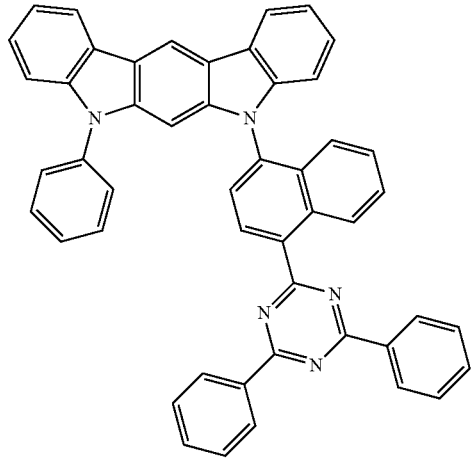

T-1
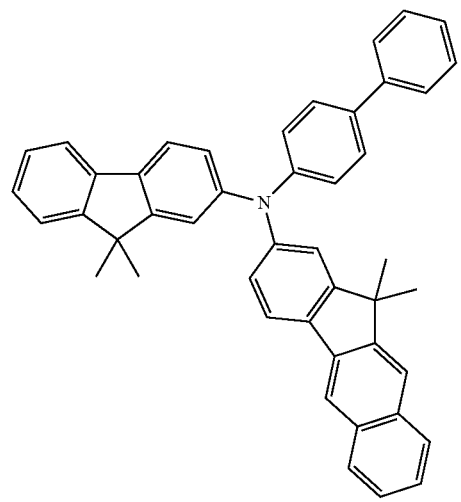
T-2
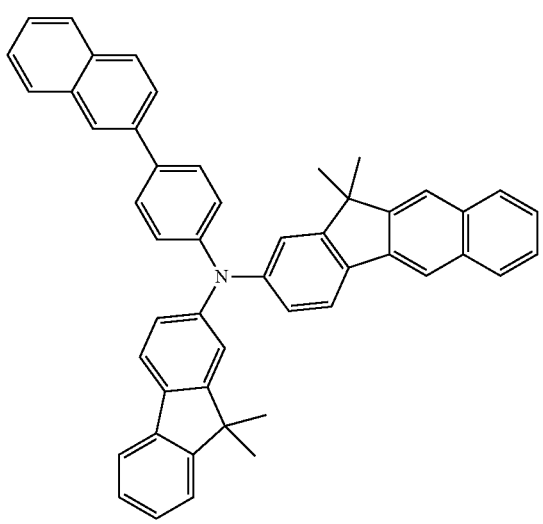
T-3
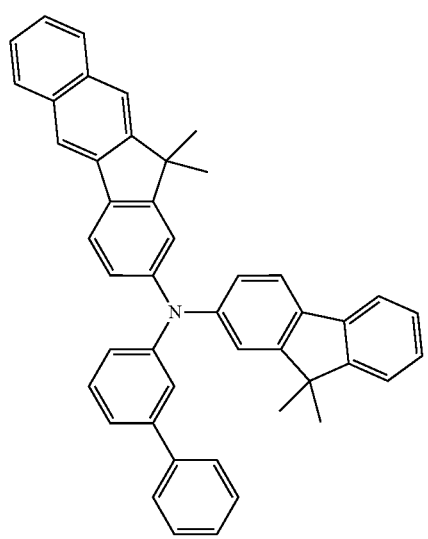
T-4
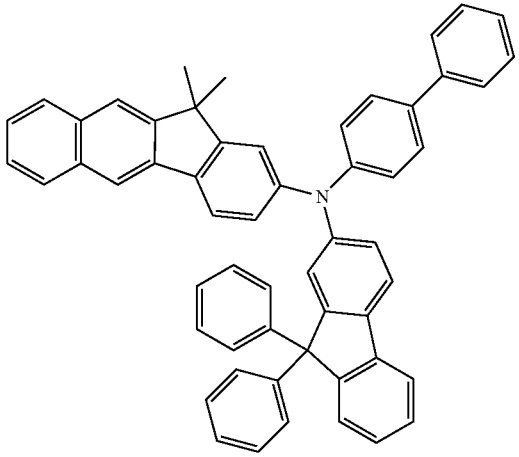
T-5
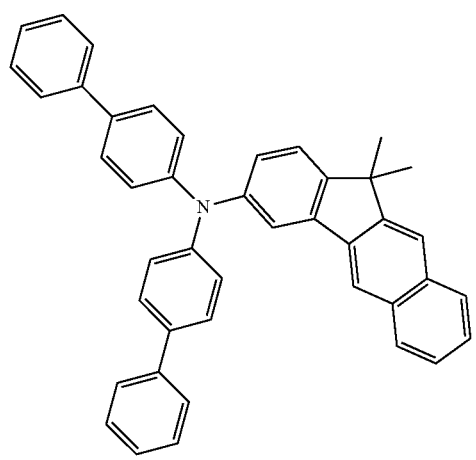
T-6
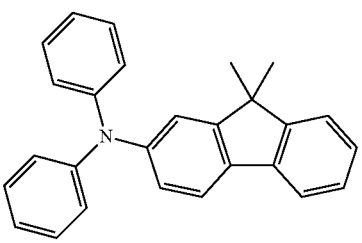
T-7
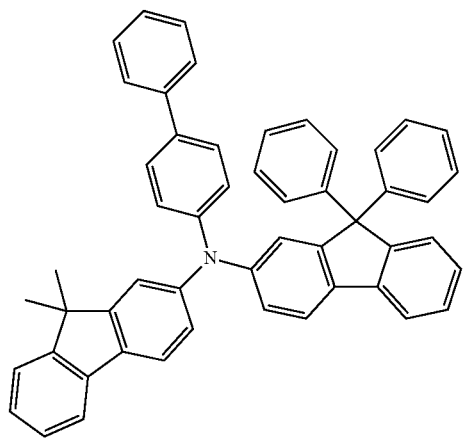

In addition, the driving voltage, luminous efficiency, and CIE color coordinates at a luminance of 1,000 nits, and the time taken for luminance to decrease from 100% to 99% at a luminance of 5,000 nits and a constant current (lifespan; T99) of the OLED devices produced in Device Examples 1 to 14 and Comparative Examples 1 to 7 are provided in Table 2 below.

TABLE 2

|  | Second Hole Transport Layer | Driving Voltage (V) | Luminous Efficiency (cd/A) | CIE x | CIE y | Lifespan (hr) |
| --- | --- | --- | --- | --- | --- | --- |
| Device Example 1 | C-7 | 2.9 | 22.5 | 0.667 | 0.333 | 37 |
| Device Example 2 | C-5 | 2.9 | 25.9 | 0.667 | 0.333 | 43 |
| Device Example 3 | C-4 | 2.9 | 22.9 | 0.666 | 0.334 | 42 |
| Device Example 4 | C-8 | 2.9 | 25.5 | 0.667 | 0.333 | 44 |
| Device Example 5 | C-6 | 2.9 | 26.5 | 0.667 | 0.333 | 51 |
| Device Example 6 | C-24 | 2.9 | 22.9 | 0.666 | 0.334 | 45 |
| Device Example 7 | C-2 | 3.0 | 25.5 | 0.669 | 0.330 | 47 |
| Device Example 8 | C-25 | 2.9 | 25.6 | 0.669 | 0.330 | 40 |
| Device Example 9 | C-62 | 3.4 | 27.3 | 0.669 | 0.331 | 34 |
| Device Example 10 | C-61 | 3.1 | 27.4 | 0.669 | 0.330 | 32 |
| Device Example 11 | C-63 | 2.9 | 25.1 | 0.669 | 0.330 | 48 |
| Device Example 12 | C-67 | 3.1 | 27.7 | 0.668 | 0.331 | 28 |
| Device Example 13 | C-69 | 2.9 | 25.4 | 0.669 | 0.331 | 43 |
| Device Example 14 | C-10 | 2.8 | 23.6 | 0.668 | 0.331 | 40 |
| Comparative Example 1 | T-1 | 3.0 | 16.0 | 0.666 | 0.334 | 25 |
| Comparative Example 2 | T-2 | 2.8 | 15.5 | 0.667 | 0.333 | 22 |
| Comparative Example 3 | T-3 | 2.8 | 19.2 | 0.667 | 0.333 | 24 |
| Comparative Example 4 | T-4 | 3.1 | 16.3 | 0.667 | 0.333 | 20 |
| Comparative Example 5 | T-5 | 3.0 | 23.8 | 0.670 | 0.330 | 20 |
| Comparative Example 6 | T-6 | 4.1 | 24.5 | 0.667 | 0.333 | 1.4 |
| Comparative Example 7 | T-7 | 2.9 | 12.2 | 0.666 | 0.334 | 21 |

LUMO, HOMO, and triplet energy values of the compound comprised in the second hole transport layer of Device Examples 1 to 14 and Comparative Examples 1 to 7 are provided in Table 3 below. The HOMO and LUMO energy values of the present disclosure were measured by using the density functional theory (DFT) in the program of Gaussian 09 of Gaussian, Inc., but is not limited thereto. The triplet energy value of the present disclosure was measured in the structure of an isomer having the lowest energy by using the time-dependent density functional theory (TD-DFT) in the program of Gaussian 09, but is not limited thereto. Specifically, the HOMO and LUMO energy values in the Device Examples and the Comparative Examples were extracted from the structure having the lowest energy among the calculated energies of the conformational isomers after structurally optimizing the structures of all of the possible conformational isomers at the level of B3LYP/6-31g*.

TABLE 3

| Compound | LUMO (eV) | HOMO (eV) | Triplet Energy (eV) |
| --- | --- | --- | --- |
| C-2 | −1.242 | −4.844 | 2.505 |
| C-4 | −1.250 | −4.790 | 2.503 |
| C-5 | −1.235 | −4.816 | 2.503 |
| C-6 | −1.238 | −4.831 | 2.504 |
| C-7 | −1.254 | −4.795 | 2.498 |
| C-8 | −1.247 | −4.830 | 2.504 |
| C-24 | −1.228 | −4.802 | 2.504 |
| C-25 | −1.230 | −4.846 | 2.504 |
| C-66 | −1.239 | −4.718 | 2.499 |
| C-62 | −1.299 | −4.891 | 2.506 |
| C-61 | −1.224 | −4.884 | 2.507 |
| C-63 | −1.252 | −4.838 | 2.499 |
| C-67 | −1.238 | −4.892 | 2.507 |
| C-68 | −1.232 | −4.823 | 2.435 |
| C-69 | −1.267 | −4.886 | 2.506 |
| C-70 | −1.213 | −4.816 | 2.503 |
| C-71 | −1.265 | −4.853 | 2.502 |
| C-10 | −1.243 | −4.764 | 2.503 |
| C-72 | −1.194 | −4.792 | 2.496 |
| T-1 | −1.242 | −4.752 | 2.377 |
| T-2 | −1.283 | −4.754 | 2.371 |
| T-3 | −1.216 | −4.770 | 2.384 |
| T-4 | −1.245 | −4.767 | 2.381 |
| T-5 | −1.268 | −4.868 | 2.505 |
| T-6 | −0.815 | −4.826 | 2.705 |
| T-7 | −1.004 | −4.744 | 2.590 |

From Device Examples 1 to 14 and Comparative Examples 1 to 4 of Tables 2 and 3, it can be seen that the compounds of the present disclosure, in which fluorenylamine bonds to the 3-position of benzofluorene, have higher triplet energy value than the compounds of Comparative Examples 1 to 4, in which fluorenylamine bonds to the 2-position of benzofluorene, and the OLED devices comprising the compounds of the present disclosure exhibit higher luminous efficiency and longer lifespan properties than the OLED devices of Comparative Examples 1 to 4. It is understood that this is because the compound of the present disclosure, in which fluorenylamine bonds to the 3-position of benzofluorene, has reduced spread of the HOMO orbital of benzofluorene compared to the compound, in which fluorenylamine bonds to the 2-position of benzofluorene, the hopping distance between molecules increases, and thereby the hole mobility decreases. That is, it is understood that the compound of the present disclosure, in which fluorenylamine bonds to the 3-position of benzofluorene, has reduced hole mobility, the charge balance in the light-emitting layer is improved, and thereby the luminous efficiency of the OLED devices comprising the compound of the present disclosure increases.

Also, from Device Examples 1 to 14 and Comparative Example 5 of Tables 2 and 3, it can be seen that the compound of the present disclosure, in which benzofluorene bonds to fluorenylamine, has higher HOMO energy value than the compound of Comparative Example 5, in which benzofluorene bonds to an amine containing no fluorene, and the OLED devices comprising the compound of the present disclosure exhibit lower driving voltage and longer lifespan properties than the OLED device of Comparative Example 5, while having similar luminous efficiency.

Further, from Device Examples 1 to 14 and Comparative Examples 6 and 7 of Tables 2 and 3, it can be seen that the compound of the present disclosure containing benzofluorenylamine has lower LUMO energy value than the compound of Comparative Examples 6 and 7 containing fluorenylamine, and the OLED devices comprising the compound of the present disclosure exhibit longer lifespan properties than the OLED devices of Comparative Examples 6 and 7, while having lower driving voltage or higher luminous efficiency.

The invention claimed is:

1. An organic electroluminescent compound represented by the following formula 1:

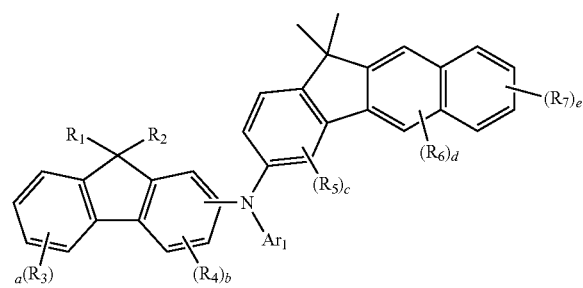

(1)

wherein

Ar$_1$ represents a substituted or unsubstituted (C1-C30)alkyl, a substituted or unsubstituted (C6-C30)aryl, or a substituted or unsubstituted 5- to 30-membered heteroaryl;

R$_1$ and R$_2$ each independently represent hydrogen, deuterium, a halogen, a substituted or unsubstituted (C1-C30)alkyl, a substituted or unsubstituted (C6-C30)aryl, or a substituted or unsubstituted (C3-C30)cycloalkyl; or adjacent R$_1$ and R$_2$ are linked to form a substituted or unsubstituted, mono- or polycyclic, 3- to 30-membered alicyclic or aromatic ring, or a combination thereof;

R$_3$ to R$_7$ each independently represent hydrogen, deuterium, a halogen, a substituted or unsubstituted (C1-C30)alkyl, a substituted or unsubstituted (C6-C30)aryl, a substituted or unsubstituted 5- to 30-membered heteroaryl, a substituted or unsubstituted (C3-C30)cycloalkyl, a substituted or unsubstituted (C6-C30)aryl(C1-C30)alkyl, —N(R$_{11}$)(R$_{12}$), —Si(R$_{13}$)(R$_{14}$)(R$_{15}$), —S(R$_{16}$), —O(R$_{17}$), a cyano, a nitro, or a hydroxyl;

R$_{11}$ to R$_{17}$ each independently represent hydrogen, deuterium, a halogen, a substituted or unsubstituted (C1-C30)alkyl, a substituted or unsubstituted (C6-C30)aryl, a substituted or unsubstituted 5- to 30-membered heteroaryl, a substituted or unsubstituted 3- to 7-membered heterocycloalkyl, or a substituted or unsubstituted (C3-C30)cycloalkyl; and a and e each independently represent an integer of 1 to 4, b and c each independently represent an integer of 1 to 3, and d represents an integer of 1 or 2, in which if each of a to e is an integer of 2 or more, each of R$_3$ to R$_7$ may be the same or different.

2. The organic electroluminescent compound according to claim 1, wherein formula 1 is represented by the following formula 2 or 3:

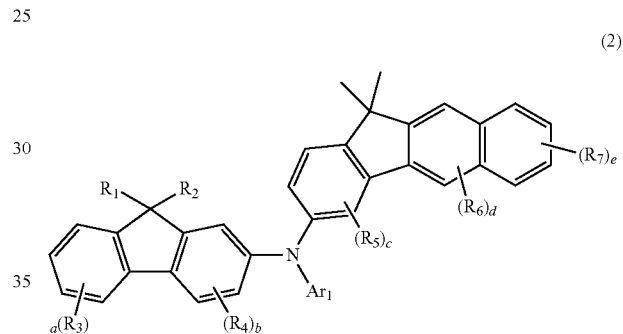

(2)

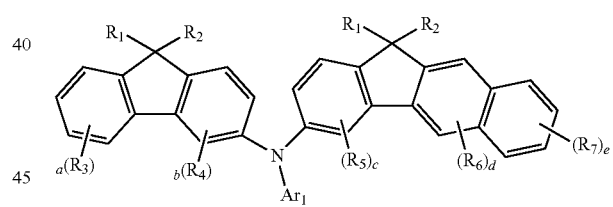

(3)

wherein Ar$_1$, R$_1$ to R$_7$, and a to e are as defined in claim 1.

3. The organic electroluminescent compound according to claim 1, wherein Ar$_1$ is selected from the following specific structures:

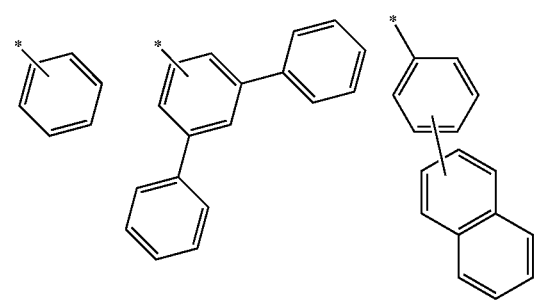

165
-continued

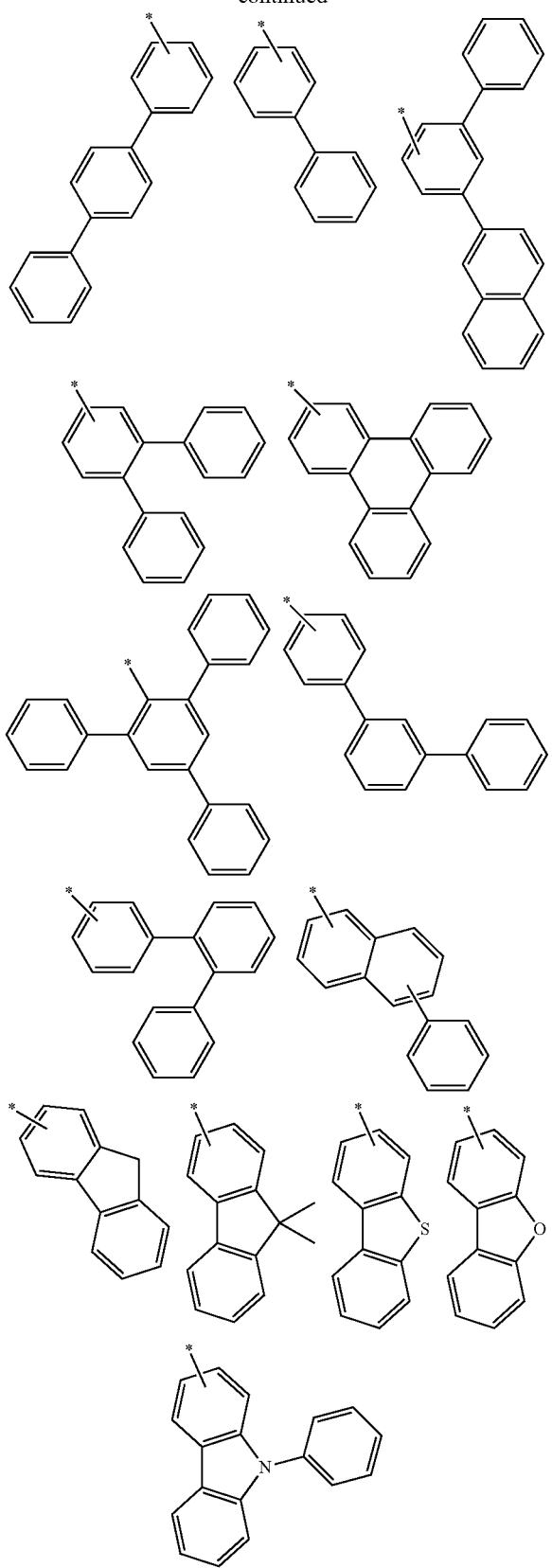

wherein * represents a bonding site with N in the amine group of general formula 1, and at least one carbon atom of the aromatic ring of the above specific structures may be replaced with a nitrogen atom.

4. The organic electroluminescent compound according to claim 1, wherein the substituents of the substituted alkyl, the substituted aryl, the substituted heteroaryl, the substituted cycloalkyl, the substituted heterocycloalkyl, the substituted arylalkyl, or the substituted mono- or polycyclic, alicyclic or aromatic ring, or a combination thereof in $Ar_1$, $R_1$ to $R_7$, and $Ru$ to $R_{17}$ each independently are at least one selected from the group consisting of deuterium, a halogen, a cyano, a carboxyl, a nitro, a hydroxyl, a (C1-C30)alkyl, a halo(C1-C30)alkyl, a (C2-C30)alkenyl, a (C2-C30)alkynyl, a (C1-C30)alkoxy, a (C1-C30)alkylthio, a (C3-C30)cycloalkyl, a (C3-C30)cycloalkenyl, a 3- to 7-membered heterocycloalkyl, a (C6-C30)aryloxy, a (C6-C30)arylthio, a 5- to 30-membered heteroaryl unsubstituted or substituted with a (C6-C30)aryl, a (C6-C30)aryl unsubstituted or substituted with a 5- to 30-membered heteroaryl, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di- (C1-C30)alkylamino, a mono- or di- (C6-C30)arylamino, a (C1-C30)alkyl(C6-C30)arylamino, a (C1-C30)alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30)alkyl, and a (C1-C30)alkyl(C6-C30)aryl.

5. The organic electroluminescent compound according to claim 1, wherein the compound represented by formula 1 is selected from the group consisting of:

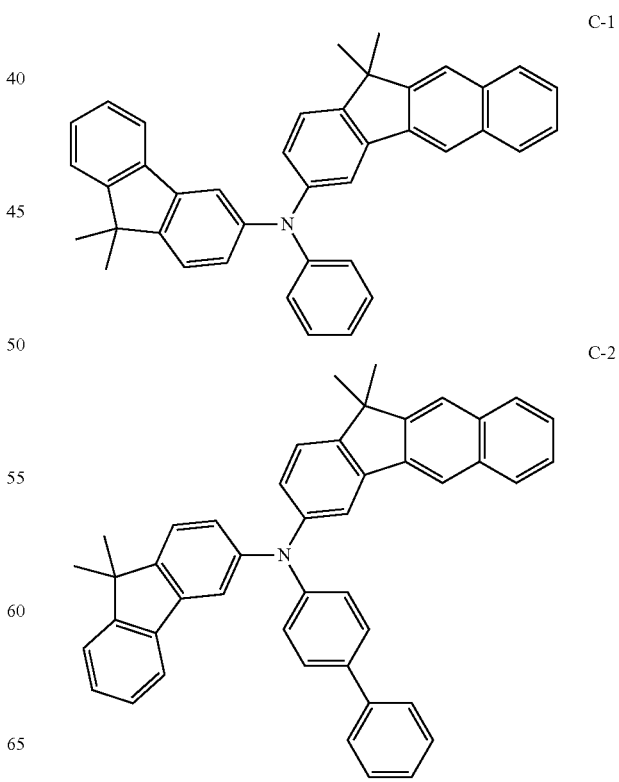

C-1

C-2

C-3
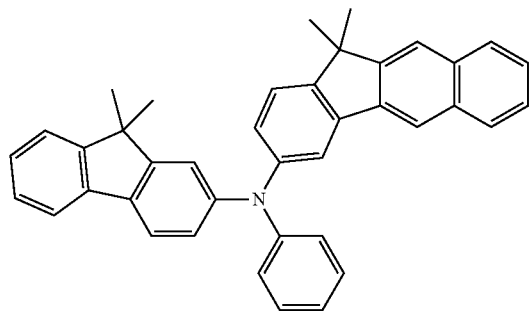
C-4
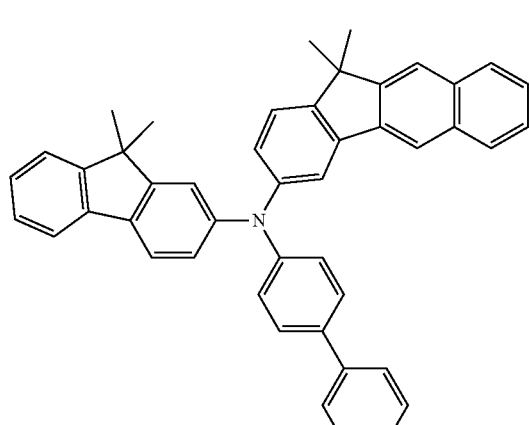
C-5
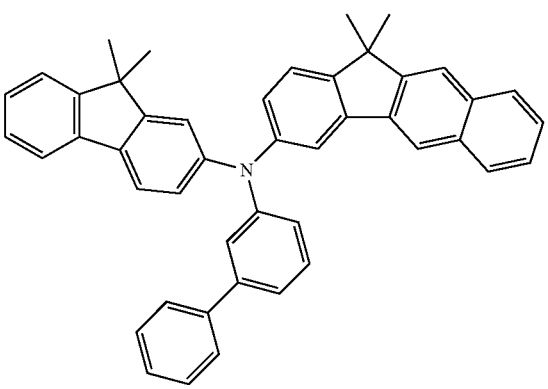
C-6
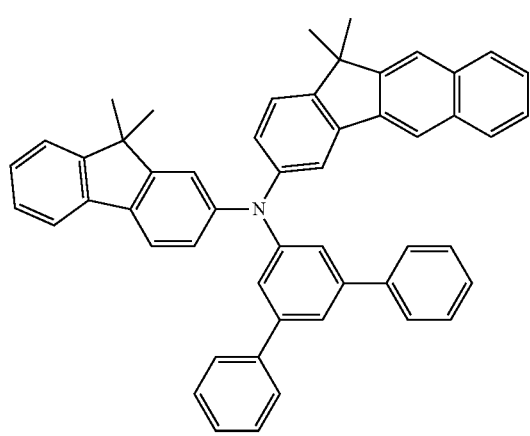
C-7
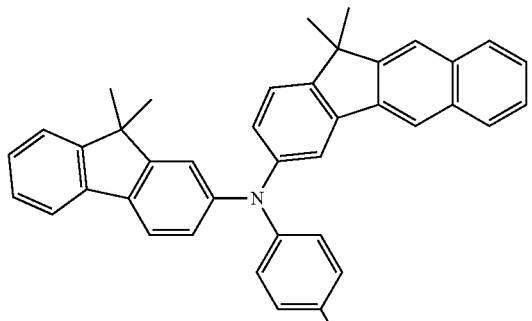
C-8
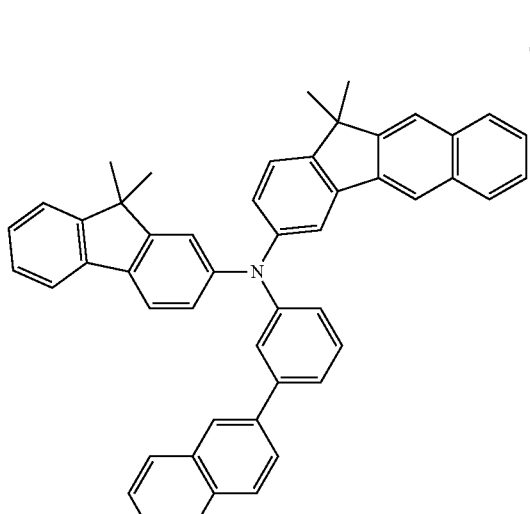
C-9
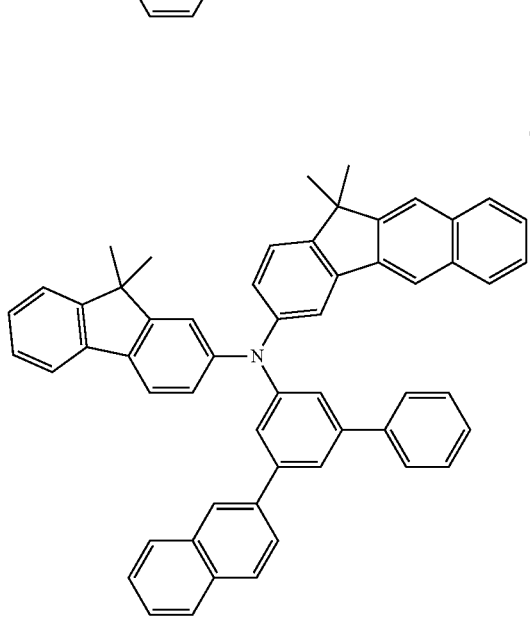

C-10
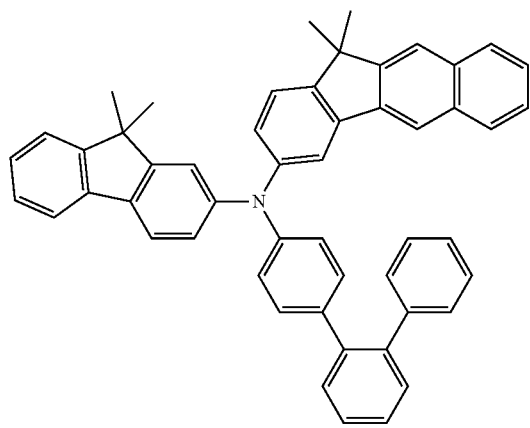
C-13
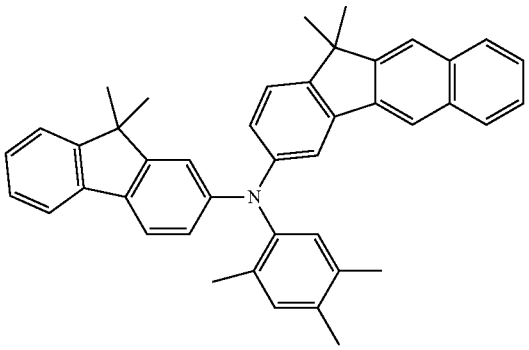
C-11
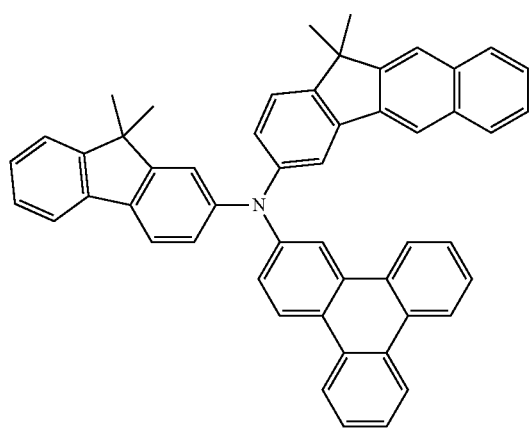
C-14
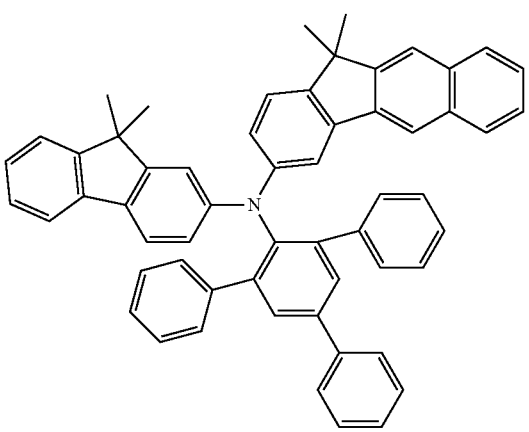
C-12
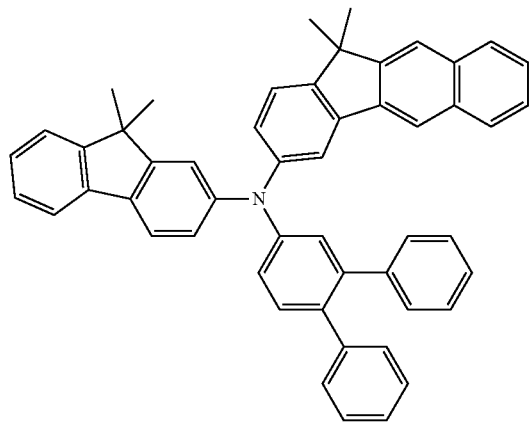
C-15
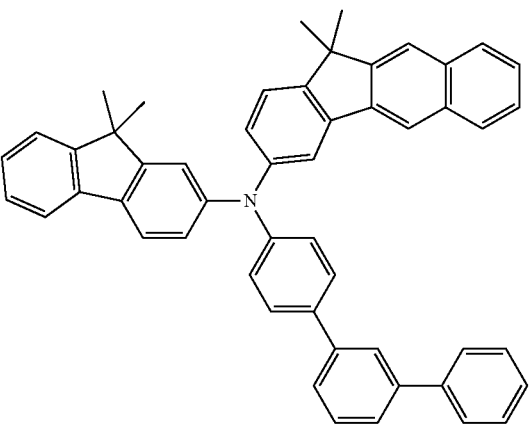

-continued
C-16
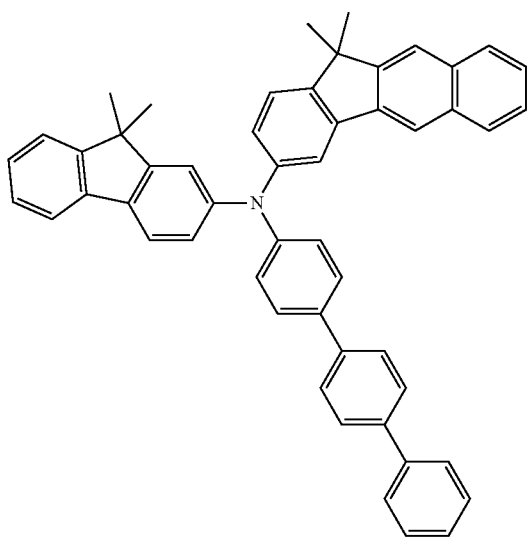
C-17
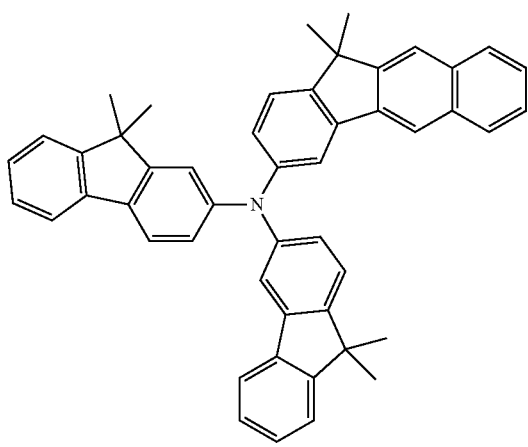
C-18
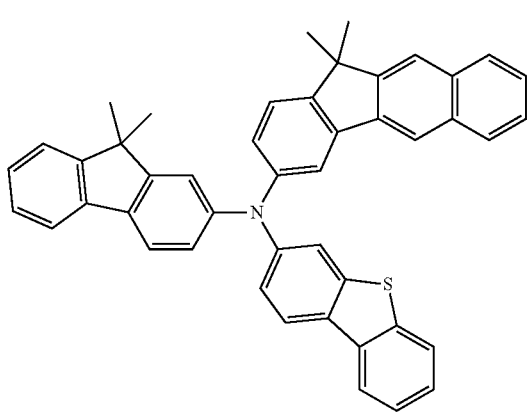
-continued
C-19
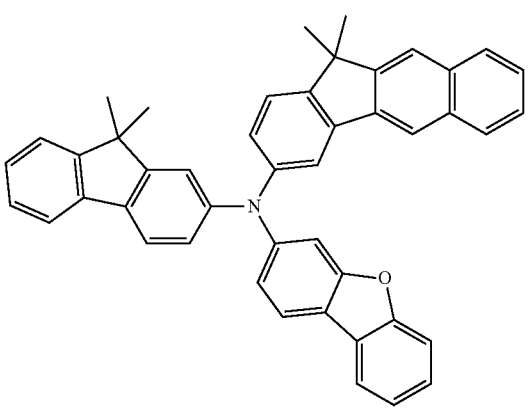
C-20
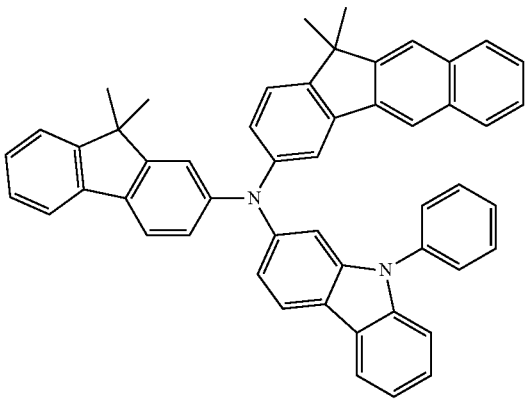
C-21
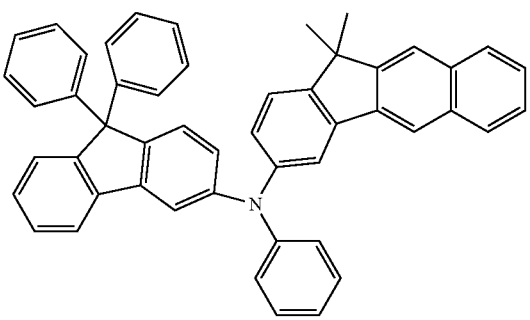

C-22
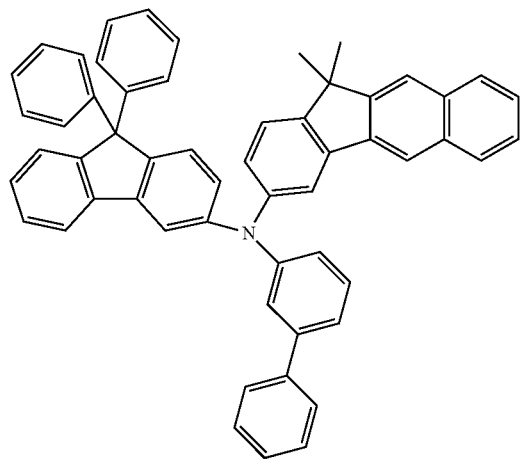
C-25
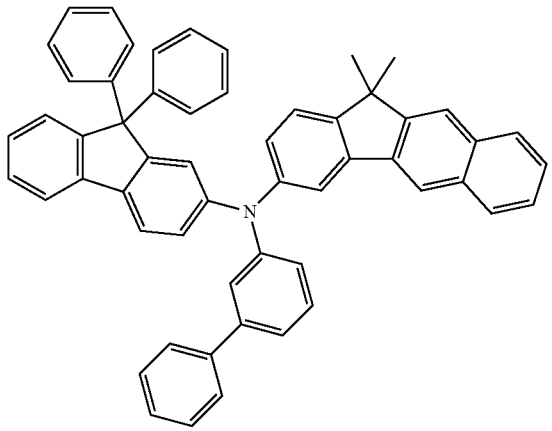
C-23
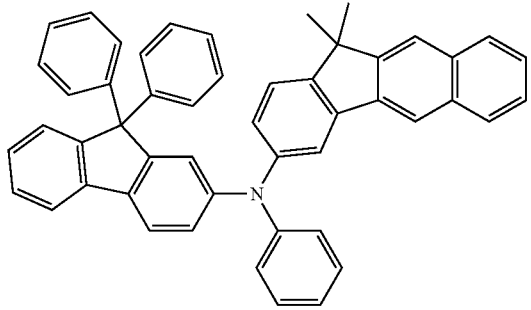
C-26
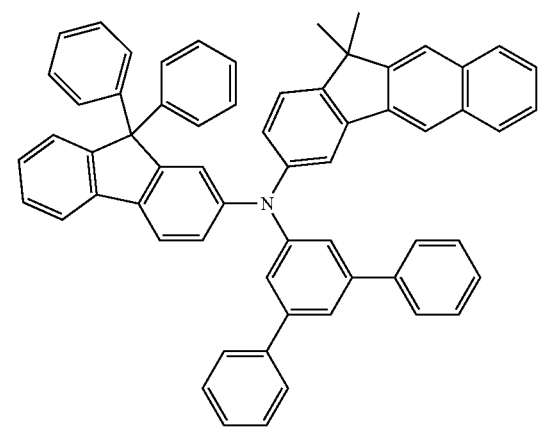
C-24
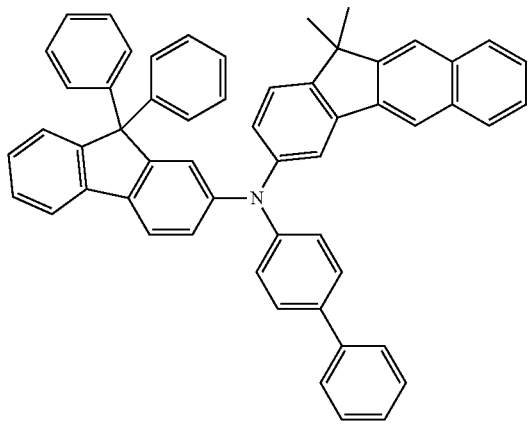
C-27
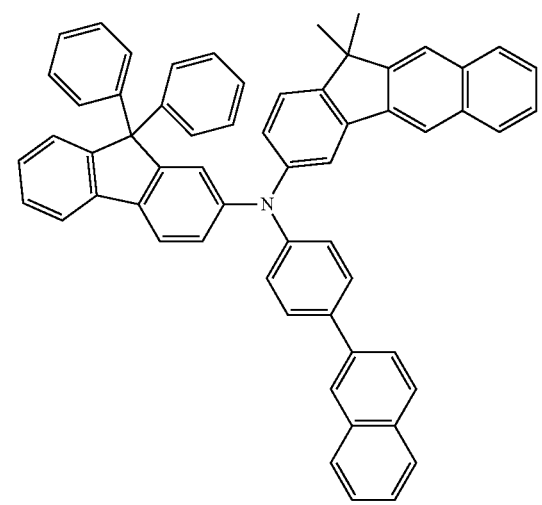

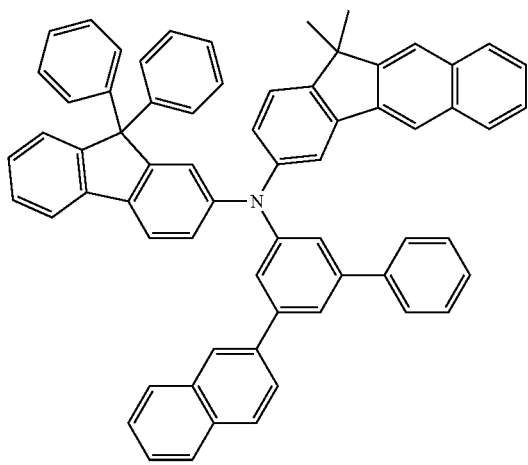
C-28
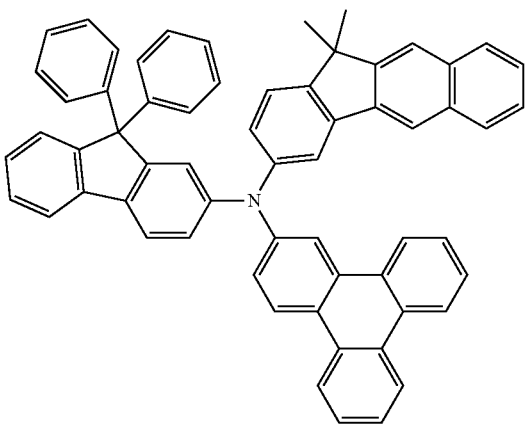
C-31
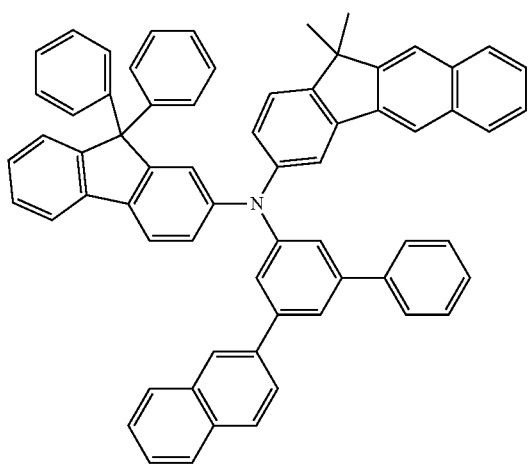
C-29
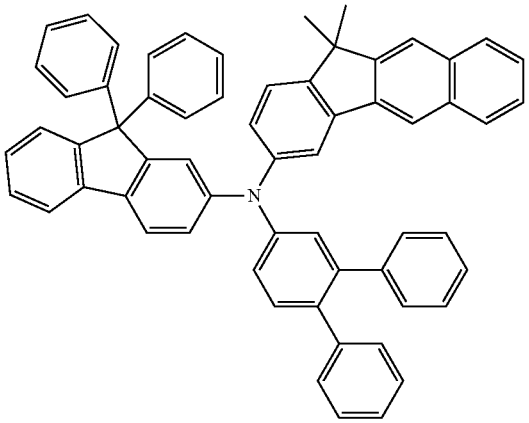
C-32
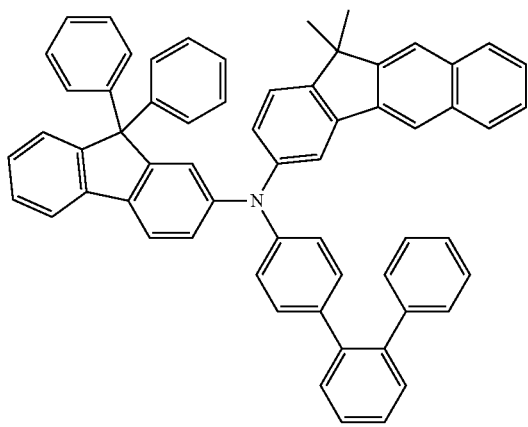
C-30
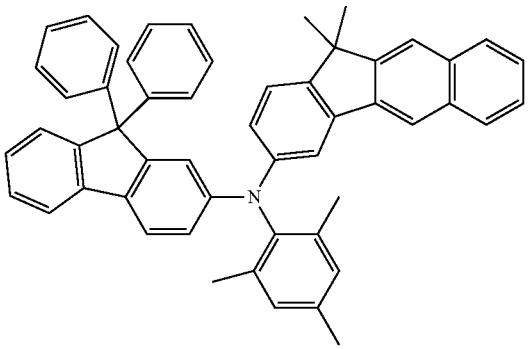
C-33

C-34
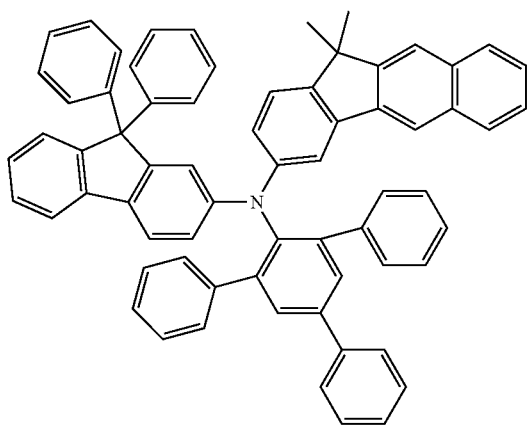
C-37
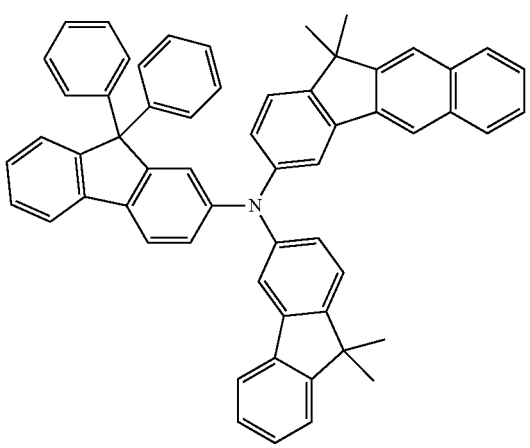
C-35
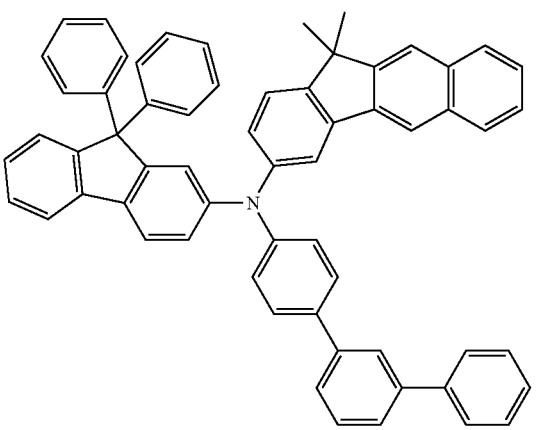
C-38
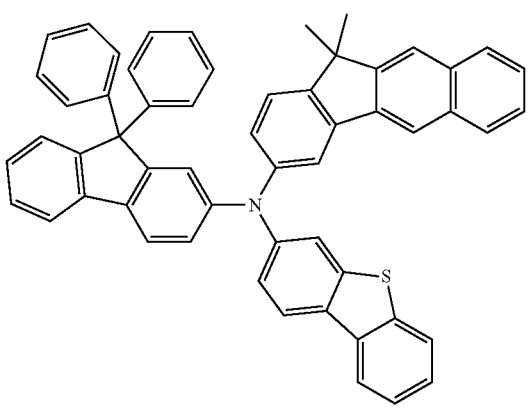
C-36
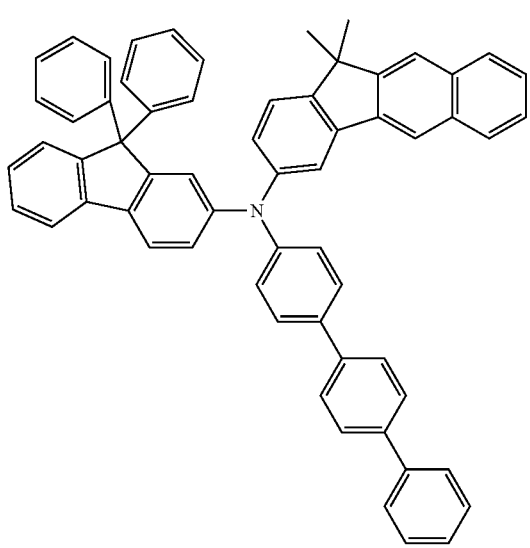
C-39
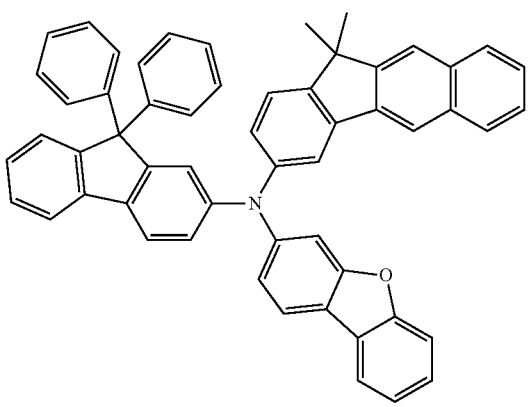

C-40
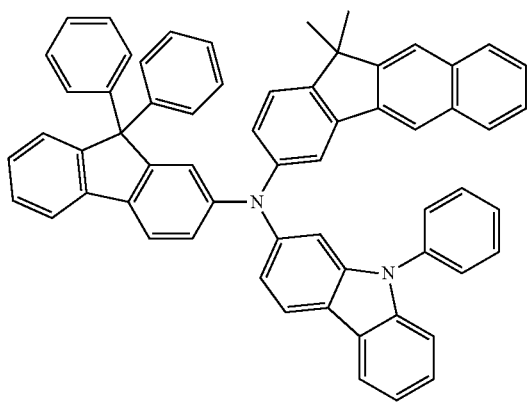
C-41
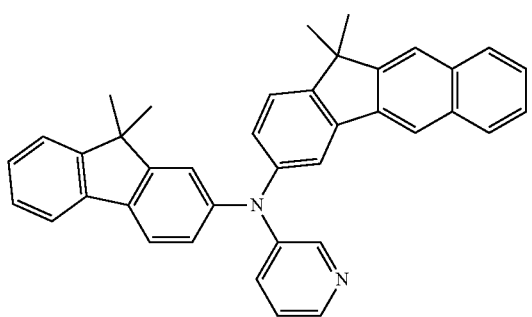
C-42
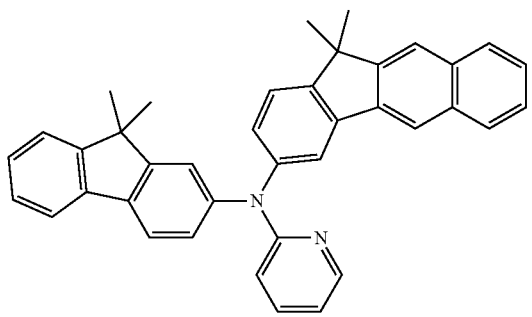
C-43
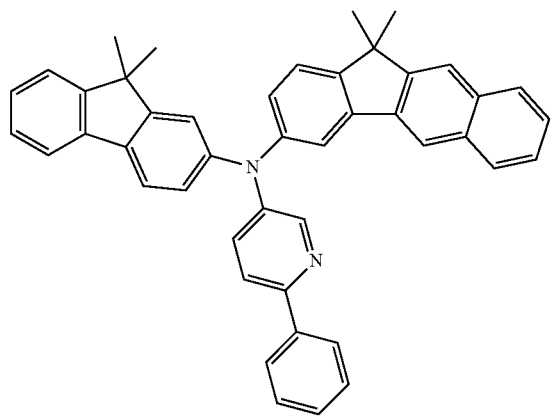
C-44
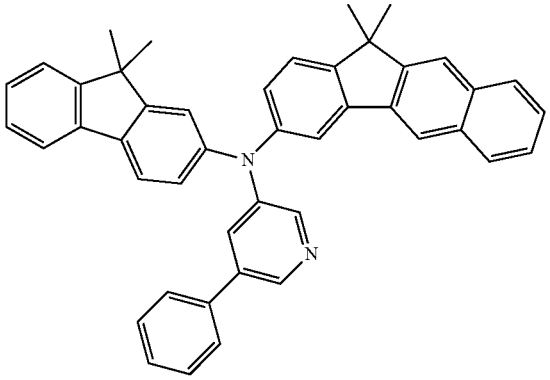
C-45
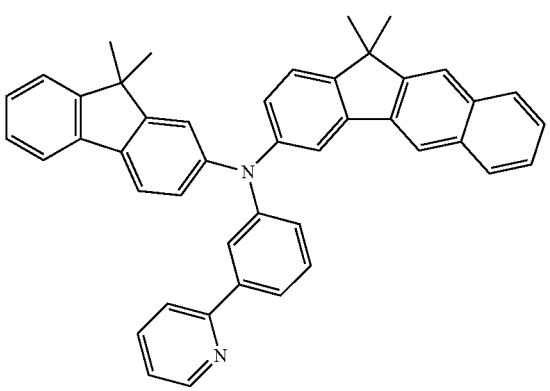
C-46
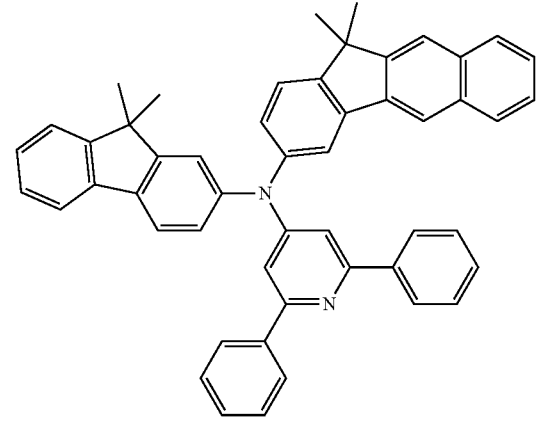

C-47
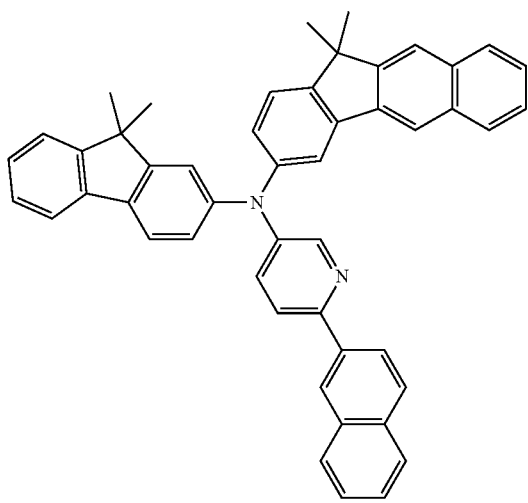
C-48
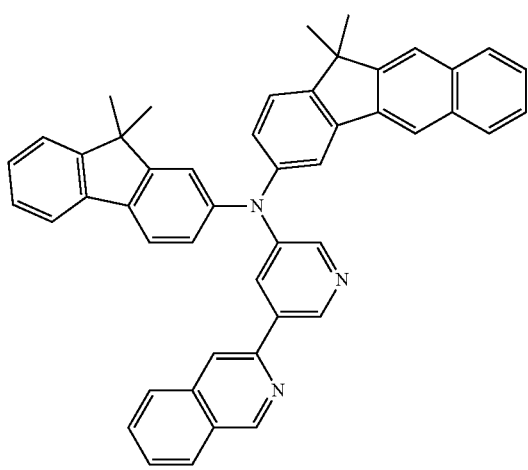
C-49
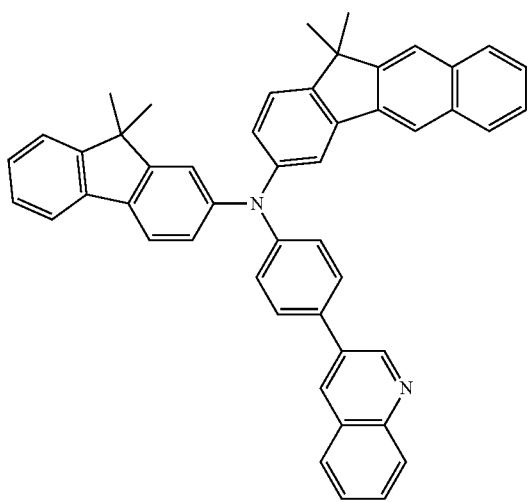
C-50
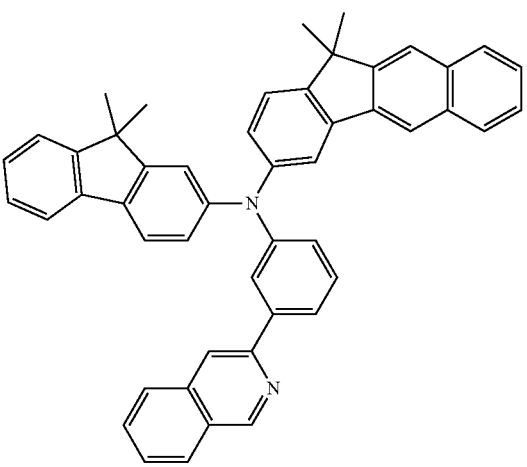
C-51
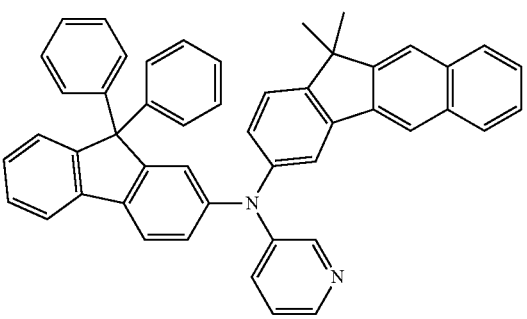
C-52
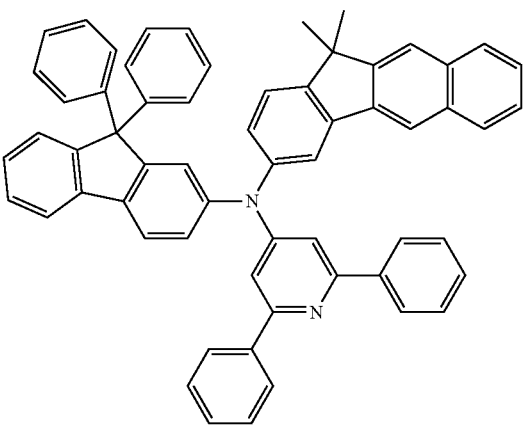

C-53
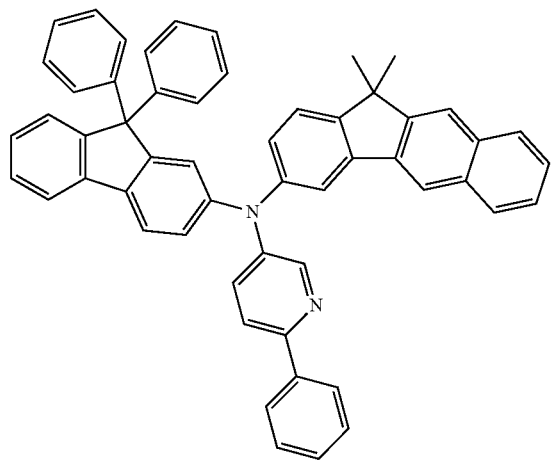
C-56
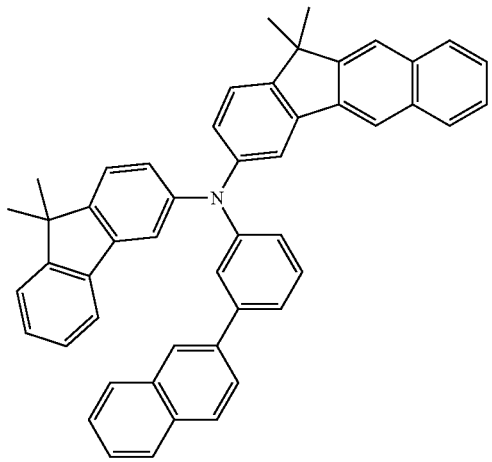
C-54
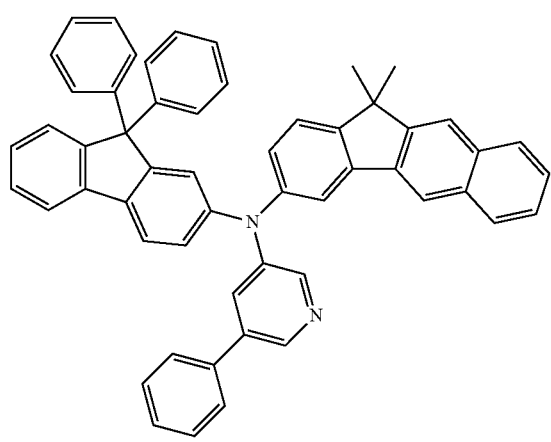
C-57
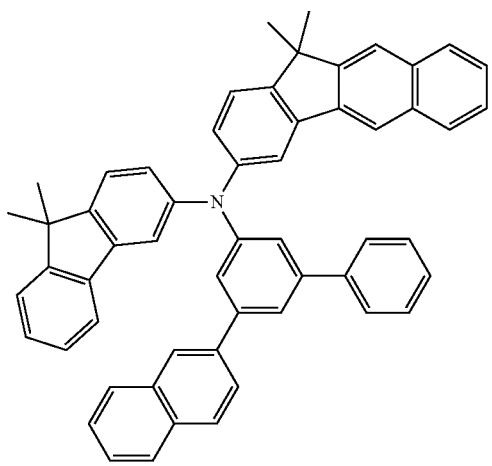
C-55
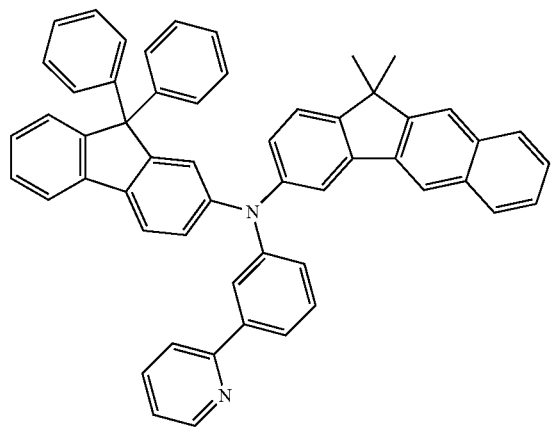
C-58
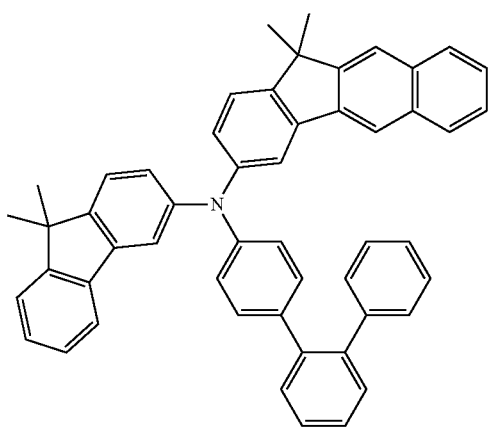

C-59
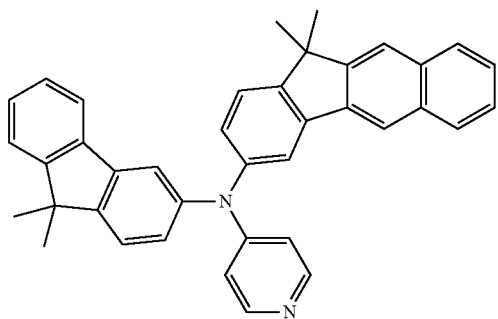
C-60
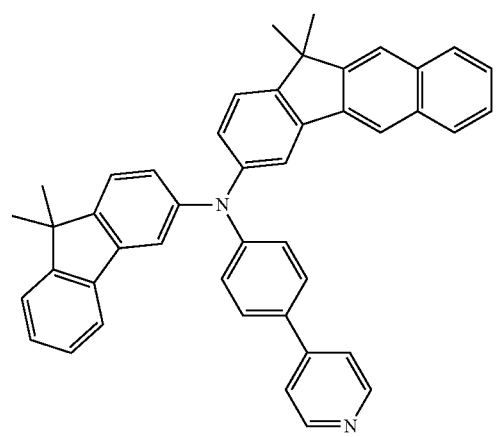
C-61
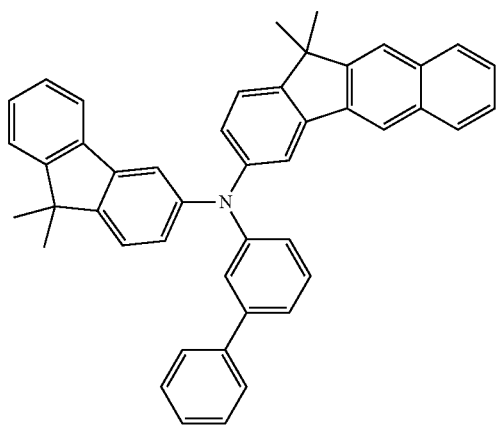
C-62
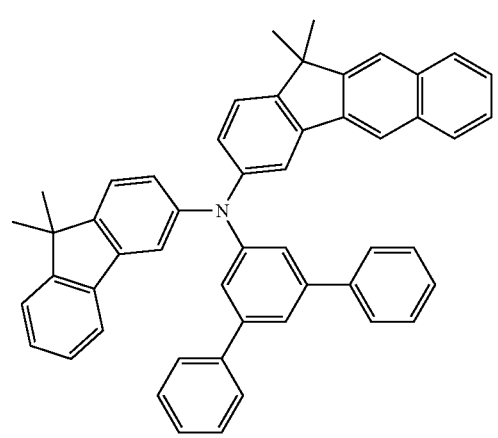
C-63
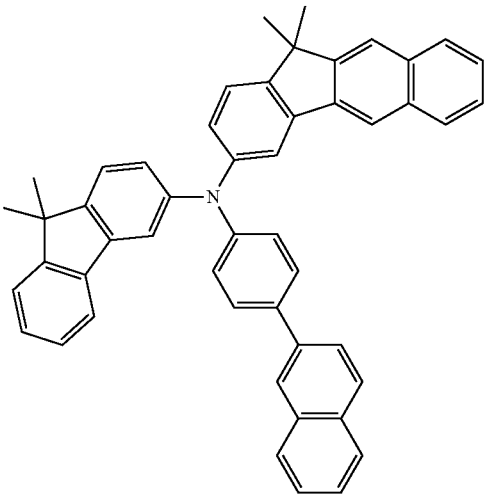
C-64
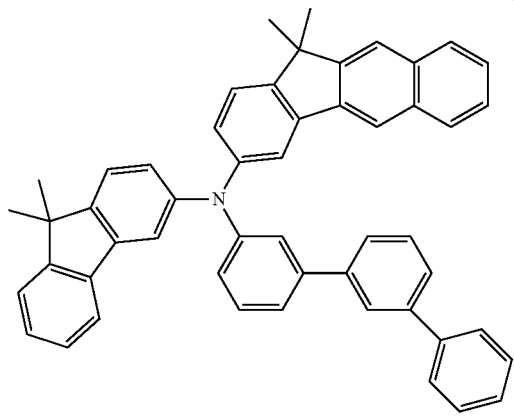
C-65
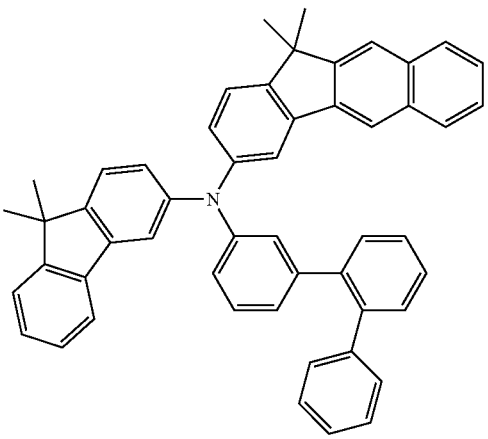

-continued

C-66
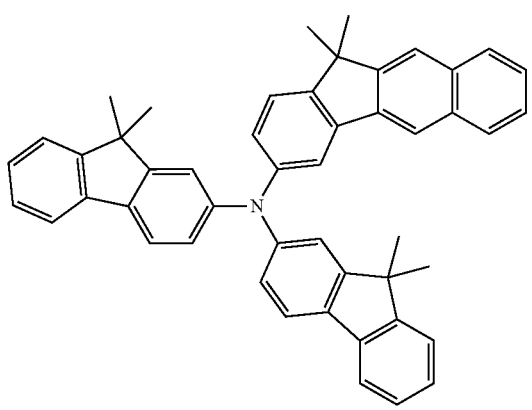

C-67
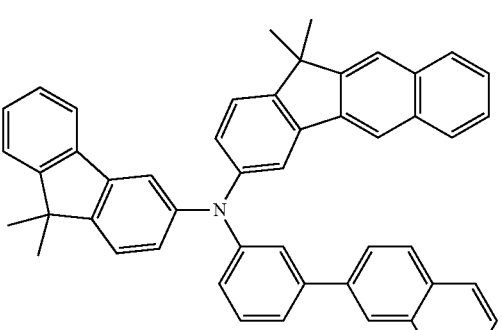

C-68
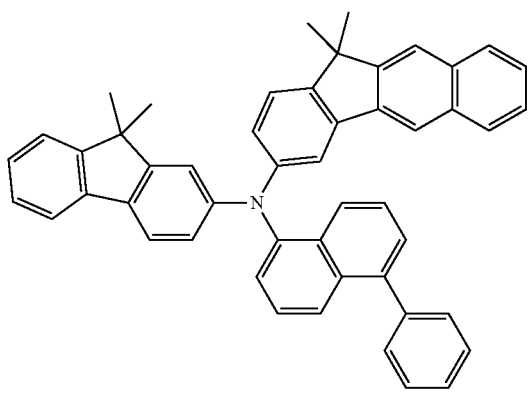

C-69
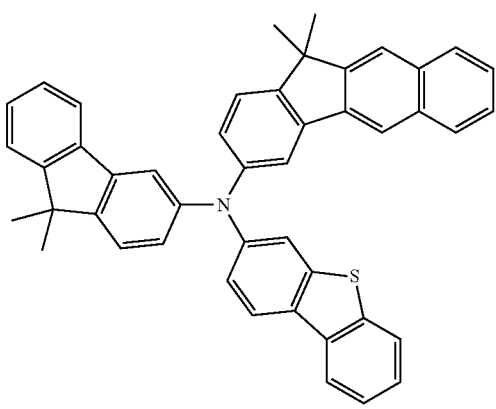

-continued

C-70
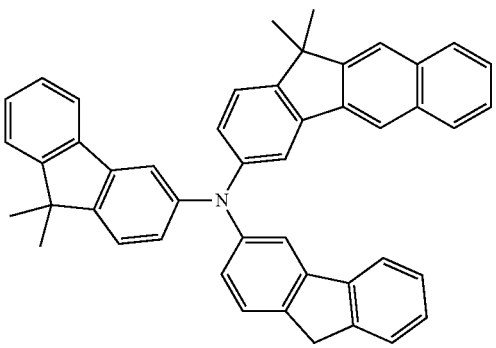

C-71
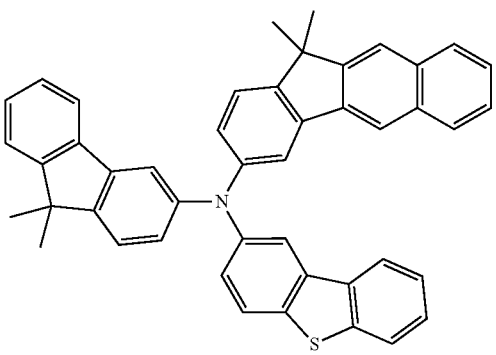

C-72
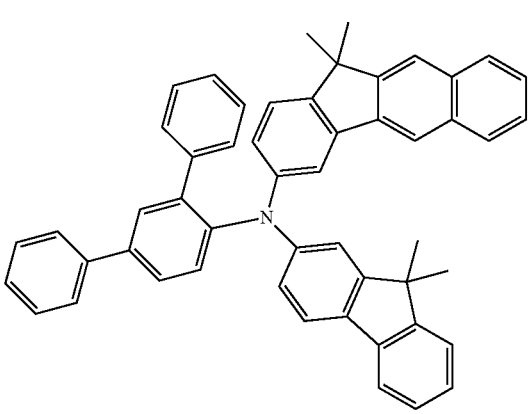

6. An organic electroluminescent material comprising the organic electroluminescent compound according to claim 1.

7. An organic electroluminescent device comprising the organic electroluminescent compound according to claim 1.

8. The organic electroluminescent device according to claim 7, wherein the organic electroluminescent compound is comprised in a hole transport zone.

* * * * *